US012805533B2

(12) United States Patent
Martino et al.

(10) Patent No.: US 12,805,533 B2
(45) Date of Patent: Nov. 24, 2026

(54) MICROBIAL COMPOSITIONS AND METHODS FOR FERMENTED FOODS

(71) Applicant: Leaven Foods, Inc., San Diego, CA (US)

(72) Inventors: Cameron Martino, San Diego, CA (US); James Gaffney, Encinitas, CA (US)

(73) Assignee: Leaven Foods, Inc., San Diego, CA (US)

( * ) Notice: Subject to any disclaimer, the term of this patent is extended or adjusted under 35 U.S.C. 154(b) by 0 days.

(21) Appl. No.: 19/413,504

(22) Filed: Dec. 9, 2025

(65) Prior Publication Data

US 2026/0096563 A1 Apr. 9, 2026

Related U.S. Application Data

(63) Continuation of application No. PCT/US2024/045648, filed on Sep. 6, 2024.

(Continued)

(51) Int. Cl.

| | |
|---|---|
| ***C12N 1/205*** | (2026.01) |
| ***A21D 8/04*** | (2006.01) |
| ***C12N 1/18*** | (2026.01) |
| ***C12N 1/185*** | (2026.01) |
| *C12R 1/01* | (2006.01) |
| *C12R 1/645* | (2006.01) |
| *C12R 1/865* | (2006.01) |

(52) U.S. Cl.

CPC ............ *A21D 8/045* (2013.01); *A21D 8/047* (2013.01); *C12N 1/18* (2013.01); *C12N 1/185* (2021.05); *C12N 1/205* (2021.05); *A23V 2400/121* (2023.08); *A23V 2400/183* (2023.08); *C12R 2001/01* (2021.05); *C12R 2001/645* (2021.05); *C12R 2001/865* (2021.05)

(58) Field of Classification Search

CPC ........ A21D 8/045; A21D 8/047; C12N 1/205; C12N 1/185; C12N 1/18; C12R 2001/01; C12R 2001/645; C12R 2001/865; A23V 2400/121; A23V 2400/183

See application file for complete search history.

(56) References Cited

U.S. PATENT DOCUMENTS

2003/0134311 A1* 7/2003 Potter .................. C12Q 1/6895 800/278

2015/0306158 A1 10/2015 Kim et al.

(Continued)

OTHER PUBLICATIONS

Adler-Nissen, "Determination of the degree of hydrolysis of food protein hydrolysates by trinitrobenzenesulfonic acid", Journal of Agricultural and Food Chemistry, vol. 27, Issue 6, (Nov. 1, 1979), pp. 1256-1262. doi:10.1021/jf60226a042.

(Continued)

*Primary Examiner* — Erik Kashnikow
*Assistant Examiner* — Karla Isobel Diviesti
(74) *Attorney, Agent, or Firm* — Cooley LLP

(57) ABSTRACT

The present invention relates to compositions comprising a purified population of one or more microorganisms for producing a dough or baked food product. Said compositions may improve fermentation of the dough or baked food product by enhancing rheological properties, improving nutritional quality, and/or increasing shelf-life of the dough or baked food product.

30 Claims, 11 Drawing Sheets

Specification includes a Sequence Listing.

Related U.S. Application Data

(60) Provisional application No. 63/581,394, filed on Sep. 8, 2023.

(56) References Cited

U.S. PATENT DOCUMENTS

| | | | | |
|---|---|---|---|---|
| 2019/0030097 | A1* | 1/2019 | Kim | A23L 33/135 |
| 2020/0063089 | A1 | 2/2020 | Kim et al. | |
| 2022/0039402 | A1 | 2/2022 | Farmer et al. | |
| 2022/0053770 | A1* | 2/2022 | Fuenzalida | A01N 63/20 |
| 2022/0151253 | A1 | 5/2022 | Choi et al. | |

OTHER PUBLICATIONS

Albagli et al., "How dried sourdough starter can enable and spread the use of sourdough bread", LWT—Food Science and Technology (149) (Jun. 11, 2021), 7 pages. DOI:10.1016/j.lwt.2021.111888.

Arora et al., "Thirty years of knowledge on sourdough fermentation: A systematic review", Trends in Food Science & Technology, vol. 108, (Feb. 2021), pp. 71-83.

Aslankoohi et al., "Non-Conventional Yeast Strains Increase the Aroma Complexity of Bread", PloS One 11(10), (Oct. 24, 2016), 18 pages. doi:10.1371/journal.pone.0165126.

Carbonetto et al., "Interactions between *Kazachstania humilis* Yeast Species and Lactic Acid Bacteria in Sourdough", Microorganisms 8(2), (Feb. 11, 2020), 20 pages. doi.org/10.3390/microorganisms8020240.

Cavallo et al., "Microbial Cell-Free Extracts Affect the Biochemical Characteristics and Sensorial Quality of Sourdough Bread", Food Chemistry, vol. 237, (Dec 15, 2017), pp. 159-168. doi: 10.1016/j.foodchem.2017.05.089.

Chavan et al., "Sourdough Technology—A Traditional Way for Wholesome Foods: A Review", Comprehensive Reviews in Food Science and Food Safety, vol. 10, Issue 3, (Apr. 6, 2011), pp. 169-182. https://doi.org/10.1111/j.1541-4337.2011.00148.x.

Cizeikiene et al., "Phytase Activity of Lactic Acid Bacteria and Their Impact on the Solubility of Minerals from Wholemeal Wheat Bread", International Journal of Food Sciences and Nutrition, 66 (7), (Sep. 23, 2015), pp. 736-742. doi: 10.3109/09637486.2015.1088939.

Cizeikiene et al., "Thermophilic lactic acid bacteria affect the characteristics of sourdough and whole-grain wheat bread", Food Bioscience, (Dec. 1, 2020), 38, 10 pages. DOI:10.1016/j.fbio.2020.100791.

Coda et al., "Antifungal Activity of Wickerhamomyces Anomalus and Lactobacillus Plantarum during Sourdough Fermentation: Identification of Novel Compounds and Long-Term Effect during Storage of Wheat Bread", Applied and Environmental Microbiology, vol. 77, No. 10, (May 2011), pp. 3484-3492. doi:10.1128/AEM.02669-10.

Coda et al., "Selected lactic acid bacteria synthesize antioxidant peptides during sourdough fermentation of cereal flours", Applied and Environmental Microbiology, vol. 78, No. 4, (Feb. 2012), pp. 1087-1096. doi:10.1128/AEM.06837-11.

Corsetti et al., "Combined Effect of Sourdough Lactic Acid Bacteria and Additives on Bread Firmness and Staling", Journal of Agricultural and Food Chemistry, 48 (7), (Jun. 27, 2000), pp. 3044-3051. doi: 10.1021/jf990853e.

De Man et al., "A Medium for the Cultivation of Lactobacilli", Journal of Applied Bacteriology, 23 (1), (Apr. 1960), pp. 130-135. https://doi.org/10.1111/j.1365-2672.1960.tb00188.

Di Cagno et al., "Use of Selected Sourdough Strains of Lactobacillus for Removing Gluten and Enhancing the Nutritional Properties of Gluten-Free Bread", Journal of Food Protection, 71 (7), (Jul. 2008), pp. 1491-1495. doi: 10.4315/0362-028x-71.7.1491.

Diana et al., "Free Amino Acids, Acrylamide and Biogenic Amines in Gamma-Aminobutyric Acid Enriched Sourdough and Commercial Breads", Journal of Cereal Science, 60 (3), (Nov. 2014), pp. 639-644. DOI:10.1016/j.jcs.2014.06.009.

Doyle et al., "Limitations of Thioglycolate Broth as a Sterility Test Medium for Materials Exposed to Gaseous Ethylene Oxide", Applied Microbiology, 16 (11), (Nov. 1968), pp. 1742-1744. doi: 10.1128/am.16.11.1742-1744.1968.

Eddleman, "Making Bacteria Media from Potato", [online archive], Jan. 1998, Accessed Sep. 4, 2023, [Captured from Internet Archive Wayback Machine on Mar. 24, 2026 at URL: https://web.archive.org/web/20110716090823/http://www.disknet.com/indiana_biolab/b029.html], 5 pages.

Garcia-Vaquero et al., "Sourdough Innovations: Novel Uses of Metabolites, Enzymes, and Microbiota from Sourdough Processing", CRC Press, (Aug. 2023), 13 pages. DOI:10.1201/9781003141143.

Gherna et al., "Culture Preservation", In Methods for General and Molecular Microbiology, (Apr. 2014), pp. 1019-1033. DOI:10.1128/9781555817497.ch47.

Karaman et al., "Use of phytase active yeasts and lactic acid bacteria isolated from sourdough in the production of whole wheat bread", LWT: Food Science and Technology 91 (May 2018), pp. 557-567. DOI:10.1016/j.lwt.2018.01.055.

Landis et al., "The Diversity and Function of Sourdough Starter Microbiomes." eLife, (Jan. 26, 2021), 24 pages. https://doi.org/10.7554/eLife.61644.

Lin et al., "Analysis of Compositions of Microbiomes with Bias Correction", Nature Communications, 11 (1), (Jul. 4, 2020), 14 pages. doi:10.1038/s41467-020-17041-7.

Lopez et al., "Strains of Lactic Acid Bacteria Isolated from Sour Doughs Degrade Phytic Acid and Improve Calcium and Magnesium Solubility from Whole Wheat Flour", Journal of Agricultural and Food Chemistry, 48 (6), (Jun. 2000), pp. 2281-2285. doi: 10.1021/jf000061g.

Loponen et al., "Use of Sourdough in Low FODMAP Baking", Foods, 7 (7), (Jun. 22, 2018), 12 pages. https://doi.org/10.3390/foods7070096.

Lozupone et al., "UniFrac: A New Phylogenetic Method for Comparing Microbial Communities", Applied and Environmental Microbiology, 71 (12), (Dec. 2005), pp. 8228-8235. doi: 10.1128/AEM.71.12.8228-8235.2005.

Martino et al., "A Novel Sparse Compositional Technique Reveals Microbial Perturbations", mSystems, 4 (1), (Feb. 12, 2019), 13 pages. doi:10.1128/mSystems.00016-19.

Martino et al., "Context-Aware Dimensionality Reduction Deconvolutes Gut Microbial Community Dynamics", Nature Biotechnology, 39 (2), (Feb. 2021), pp. 165-168; 12 pages. doi:10.1038/s41587-020-0660-7.

Meng et al., "Dimension Reduction Techniques for the Integrative Analysis of Multi-Omics Data", Briefings in Bioinformatics, 17 (4), (Jul. 2016), pp. 628-641. doi:10.1093/bib/bbv108.

Montemurro et al., "Investigation of the Nutritional, Functional and Technological Effects of the Sourdough Fermentation of Sprouted Flours", International Journal of Food Microbiology, 302 (Aug. 2, 2019), pp. 47-58. doi:10.1016/j.ijfoodmicro.2018.08.005.

PCT Application No. PCT/US2024/045648, International Preliminary Report on Patentability mailed Mar. 19, 2026, Applicant Leaven Foods Inc.; 11 pages.

PCT Application No. PCT/US2024/045648, International Search Report and Written Opinion mailed Dec. 12, 2024, Applicant Leaven Foods, Inc., 16 pages.

PCT Application No. PCT/US2024/045648, Invitation to Pay Additional fees mailed Oct. 17, 2024, Applicant Leaven Foods, Inc., 3 pages.

Rahman et al., "BIRDMan: A Bayesian Differential Abundance Framework That Enables Robust Inference of Host-Microbe Associations", bioRxiv : The Preprint Server for Biology, (Feb. 2, 2023), 28 pages. doi:10.1101/2023.01.30.526328.

Rizzello et al., "Highly Efficient Gluten Degradation by Lactobacilli and Fungal Proteases during Food Processing: New Perspectives for Celiac Disease", Applied and Environmental Microbiology, 73 (14), (Jul. 2007), pp. 4499-4507. doi:10.1128/AEM.00260-07.

Rizzello et al., "Sourdough Fermented Breads Are More Digestible than Those Started with Baker's Yeast Alone: An In Vivo Challenge Dissecting Distinct Gastrointestinal Responses", Nutrients, 11 (12), (Dec. 4, 2019), 21 pages. doi:10.3390/nu11122954.

(56) References Cited

OTHER PUBLICATIONS

Rizzello et al., "Use of Fungal Proteases and Selected Sourdough Lactic Acid Bacteria for Making Wheat Bread with an Intermediate Content of Gluten", Food Microbiology, vol. 37, (Feb. 2014), pp. 59-68. doi:10.1016/j.fm.2013.06.017.
Rohart et al., "mixOmics: An R Package for Omics Feature Selection and Multiple Data Integration", PLOS Computational Biology, 13 (11), (Nov. 3, 2017), 19 pages. doi:10.1371/journal.pcbi.1005752.
Siepmann et al., "Overview of Sourdough Technology: From Production to Marketing", Food and Bioprocess Technology, 11(1), (Feb. 2018), pp. 242-270. DOI:10.1007/s11947-017-1968-2.
Timmermans et al., "Study of the Fermentation Characteristics of Non-Conventional Yeast Strains in Sweet Dough", Foods, 12 (4), (Feb. 15, 2023), 16 pages. doi:10.3390/foods12040830.
Tucker et al., "A Guide to Phylogenetic Metrics for Conservation, Community Ecology and Macroecology", Biological Reviews of the Cambridge Philosophical Society 92 (2), (May 2017), pp. 698-715. doi:10.1111/brv.12252.
Vermeulen et al., "Glutamine Deamidation by Cereal associated Lactic Acid Bacteria", Journal of Applied Microbiology, 103 (4), (Oct. 2007), pp. 1197-1205. doi:10.1111/j.1365-2672.2007.03333.x.
Weiss et al., "Electrophoretic Characterization of Wheat Grain Allergens from Different Cultivars Involved in Bakers' Asthma", Electrophoresis, 14 (8), (Aug. 1993), pp. 805-816. doi:10.1002/elps.11501401126.
Zotta et al., "Proteolysis in Model Sourdough Fermentations", Journal of Agricultural and Food Chemistry, 54 (7), (Mar. 3, 2006), pp. 2567-2574. doi:10.1021/jf052504s.

* cited by examiner

MICROBIAL COMPOSITIONS AND METHODS FOR FERMENTED FOODS

CROSS-REFERENCE TO RELATED APPLICATIONS

This application is a continuation of International Application No. PCT/US2024/045648, filed Sep. 6, 2024, which claims the benefit of priority to U.S. Provisional Application No. 63/581,394 filed on Sep. 8, 2023, the disclosure of each of which is incorporated by reference in its entirety.

FIELD OF THE DISCLOSURE

The present disclosure relates to compositions comprising a purified population of one or more microorganisms for producing a dough or baked food product. Said compositions improve fermentation of the dough or baked food product by enhancing rheological properties, improving nutritional quality, and/or increasing shelf-life of the dough or baked food product.

REFERENCE TO AN ELECTRONIC SEQUENCE LISTING

The contents of the electronic sequence listing (LEFO_001_01US_SeqList_ST26.xml; Size: 279,364 bytes; and Date of Creation: Nov. 14, 2025) are herein incorporated by reference in its entirety.

BACKGROUND

Traditionally sourdough is formed by mixing cereals and water into a dough, which is spontaneously fermented from an endogenous symbiotic community of fungi and bacteria that forms over a period of hours or days and is refreshed with additional substrates over time (Hammes and Ganzle 1998). The requirement of refreshing the sourdough by adding additional flour and water, referred to as propagation or backslopping, makes sourdough costly and time-consuming. Moreover, the spontaneous nature of the fermentation and lack of direct control of the microorganisms being used makes it difficult to safely implement, especially at scale (Novotni, Gänzle, and Rocha 2021). For these reasons and others, traditional sourdough has largely been replaced with baker's yeast (*Saccharomyces cerevisiae*) in most applications (Coda et al. 2012).

Recently there has been a resurgence in interest in sourdough, accompanied by a realization of the many benefits of sourdough over the use of *Saccharomyces cerevisiae* alone. First, sourdough can improve the organoleptic properties of the dough through the sourdough microbial community adding additional flavor compounds and improving the texture and aroma (Vermeulen, Ganzle, and Vogel 2007; Cavallo et al. 2017; Landis et al. 2021; Timmermans et al. 2023; Crowley 2004; Garcia-Vaquero and Rocha 2023). Second, the sourdough microbial community can positively impact the health benefits of dough and resulting baked goods. Namely, these communities of microorganisms can reduce the glycemic index (Carlo Giuseppe Rizzello et al. 2019; Garcia-Vaquero and Rocha 2023), reduce or remove immunogenic gluten epitopes (Carlo G. Rizzello et al. 2007; Carlo Giuseppe Rizzello et al. 2014; Di Cagno et al. 2008), pre-ferment phytic acids (Lopez et al. 2000; Garcia-Vaquero and Rocha 2023; Karaman et al. 2018; Cizeikiene et alt 2020), digest increased amounts of fermentable oligosaccharides, disaccharides, monosaccharides, and polyols (Garcia-Vaquero and Rocha 2023; Loponen and Gänzle 2018), and boost the mineral/vitamin content (Garcia-Vaquero and Rocha 2023; Montemurro et al. 2019; Rodriguez-Ramiro et al. 2017) of the dough compared to *Saccharomyces cerevisiae* alone. Finally, sourdough can improve the sustainability of baked goods, for example, by naturally increasing the shelf-life (Corsetti et al. 2000; Coda et al. 2011; Arora et al. 2021).

Simply adding in the by-products of fermentation, such as lactic acid, or reducing the microbial community down to a single strain like *Saccharomyces cerevisiae* does not produce these effects (Aslankoohi et al. 2016; Garcia-Vaquero and Rocha 2023; Siepmann et al. 2018). Moreover, producing sourdough at the scale needed to feed the population is not practical (Albagli et al. 2021). Thus, simply scaling the current methods for baked goods production is not feasible.

Consequently, there is a need in the art to identify compositions and methods for replicating both the organoleptic and health benefits observed with sourdough microbial communities in a safe, affordable, and consistent way at scale to satisfy the needs of our expanding population.

SUMMARY

The present disclosure provides a composition comprising a purified population of one or more microorganisms comprising a nucleic acid sequence that shares at least 97% sequence identity with a nucleic acid sequence selected from SEQ ID NOs: 1-272; and a food-grade carrier or excipient. In some embodiments, the purified population of one or more microorganisms comprises a nucleic acid sequence that shares at least 98% sequence identity with a nucleic acid sequence selected from SEQ ID NOs: 1-272. In some embodiments, the purified population of one or more microorganisms comprises a nucleic acid sequence that shares at least 99% sequence identity with a nucleic acid sequence selected from SEQ ID NOs: 1-272. In some embodiments, the purified population of one or more microorganisms comprises a nucleic acid sequence selected from SEQ ID NOs: 1-272.

In some embodiments, the purified population of one or more microorganisms comprises a yeast with an ITS nucleic acid sequence sharing at least 97%, at least 98%, or at least 99% sequence identity with SEQ ID NO: 207 or SEQ ID NO: 267. In some embodiments, the purified population of one or more microorganisms comprises a yeast with an ITS nucleic acid sequence comprising SEQ ID NO: 207 or SEQ ID NO: 267. In some embodiments, the purified population of one or more microorganisms comprises a *Saccharomyces cerevisiae* as deposited as PTA-127804.

In some embodiments, the purified population of one or more microorganisms comprises a yeast with an ITS nucleic acid sequence sharing at least 97%, at least 98%, or at least 99% sequence identity with SEQ ID NO: 159, SEQ ID NO: 268, or SEQ ID NO: 269. In some embodiments, the purified population of one or more microorganisms comprises a yeast with an ITS nucleic acid sequence comprising SEQ ID NO: 159, SEQ ID NO: 268, or SEQ ID NO: 269. In some embodiments, the purified population of one or more microorganisms comprises a *Kazachstania humilis* as deposited as PTA-127805.

In some embodiments, the purified population of one or more microorganisms comprises a bacterium with a 16S nucleic acid sequence sharing at least 97%, at least 98%, or at least 99% sequence identity with SEQ ID NO: 4 or SEQ ID NO: 270. In some embodiments, the purified population of one or more microorganisms comprises a bacterium with a 16S nucleic acid sequence comprising SEQ ID NO: 4 or SEQ ID NO: 270. In some embodiments, the purified population of one or more microorganisms comprises a *Fructilactobacillus sanfranciscensis* as deposited as PTA-127806.

In some embodiments, the purified population of one or more microorganisms comprises a bacterium with a 16S nucleic acid sequence sharing at least 97%, at least 98%, or at least 99% sequence identity with SEQ ID NO: 10 or SEQ ID NO: 271. In some embodiments, the purified population of one or more microorganisms comprises a bacterium with a 16S nucleic acid sequence comprising SEQ ID NO: 10 or SEQ ID NO: 271. In some embodiments, the purified population of one or more microorganisms comprises a *Pediococcus pentosaceus* as deposited as PTA-127807.

In some embodiments, the purified population of one or more microorganisms comprises a bacterium with a 16S nucleic acid sequence sharing at least 97%, at least 98%, or at least 99% sequence identity with SEQ ID NO: 8 or SEQ ID NO: 272. In some embodiments, the purified population of one or more microorganisms comprises a bacterium with a 16S nucleic acid sequence comprising SEQ ID NO: 8 or SEQ ID NO: 272. In some embodiments, the purified population of one or more microorganisms comprises a *Levilactobacillus brevis* as deposited as PTA-127808.

In some embodiments, the purified population of one or more microorganisms comprises: (a) a yeast with an ITS nucleic acid sequence sharing at least 97%, at least 98%, at least 99%, or 100% sequence identity to SEQ ID NO: 207 or SEQ ID NO: 267; (b) a yeast with an ITS nucleic acid sequence sharing at least 97%, at least 98%, at least 99%, or 100% sequence identity to SEQ ID NO: 159, SEQ ID NO: 268, or SEQ ID NO: 269; (c) a bacterium with a 16S nucleic acid sequence sharing at least 97%, at least 98%, at least 99%, or 100% sequence identity to SEQ ID NO: 4 or SEQ ID NO: 270; (d) a bacterium with a 16S nucleic acid sequence sharing at least 97%, at least 98%, at least 99%, or 100% sequence identity to SEQ ID NO: 10 or SEQ ID NO: 271; and/or (e) a bacterium with a 16S nucleic acid sequence sharing at least 97%, at least 98%, at least 99%, or 100% sequence identity to SEQ ID NO: 8 or SEQ ID NO: 272.

In some embodiments, the purified population of one or more microorganisms comprises: (a) a yeast with an ITS nucleic acid sequence sharing at least 97%, at least 98%, at least 99%, or 100% sequence identity to SEQ ID NO: 207 or SEQ ID NO: 267; and/or (b) a bacterium with a 16S nucleic acid sequence sharing at least 97%, at least 98%, at least 99%, or 100% sequence identity to SEQ ID NO: 4 or SEQ ID NO: 270. In some embodiments, the purified population of one or more microorganisms comprises: (a) a yeast with an ITS nucleic acid sequence sharing at least 97%, at least 98%, at least 99%, or 100% sequence identity to SEQ ID NO: 207 or SEQ ID NO: 267; and (b) a bacterium with a 16S nucleic acid sequence sharing at least 97%, at least 98%, at least 99%, or 100% sequence identity to SEQ ID NO: 4 or SEQ ID NO: 270.

In some embodiments, the purified population of one or more microorganisms comprises: (a) a *Saccharomyces cerevisiae* as deposited as PTA-127804; (b) a *Kazachstania humilis* as deposited as PTA-127805; (c) a *Fructilactobacillus sanfranciscensis* as deposited as PTA-127806; (d) a *Pediococcus pentosaceus* as deposited as PTA-127807; and/or (e) a *Levilactobacillus brevis* as deposited as PTA-127808.

In some embodiments, the purified population of one or more microorganisms comprises: (a) a *Saccharomyces cerevisiae* as deposited as PTA-127804; and/or (b) a *Fructilactobacillus sanfranciscensis* as deposited as PTA-127806. In some embodiments, the purified population of one or more microorganisms comprises: (a) a *Saccharomyces cerevisiae* as deposited as PTA-127804; and (b) a *Fructilactobacillus sanfranciscensis* as deposited as PTA-127806.

In some embodiments, the one or more microorganisms is lyophilized. In some embodiments, the one or more microorganisms is encapsulated.

In some embodiments, the one or more microorganisms is present in the composition at about $10^2$ CFU/g or more. In some embodiments, the one or more microorganisms is present in the composition at about $10^9$ CFU/g, about $10^{10}$ CFU/g, about $10^{11}$ CFU/g, about $10^{12}$ CFU/g, about $10^{13}$ CFU/g, or about $10^{14}$ CFU/g.

In some embodiments, the composition comprises one or more additional preservatives. In some embodiments, the composition comprises one or more additional flavoring agents. In some embodiments, the composition comprises one or more additional leavening agents.

In some embodiments, the composition is formulated as a dry powder, food ingredient, food preparation, food supplement, water additive, moisture-stabilized additive, consumable, solid, gel, liquid, or dough.

In some embodiments, the composition is a food. In some embodiments, the composition is a dough. In some embodiments, the composition is a starter culture for bakery good production.

In some embodiments, the composition is a baked good. In some embodiments, the baked good is a bread. In some embodiments, the baked good is a sourdough bread.

In some embodiments, the present disclosure provides a method for improving the fermentation of a food product, the method comprising admixing an effective amount of the composition described herein to the food product.

In some embodiments, the present disclosure provides a method of producing a dough, the method comprising admixing an effective amount of the composition described herein to the dough.

In some embodiments, the present disclosure provides a method of increasing the shelf-life of a dough or baked good, the method comprising admixing an effective amount of the composition described herein to the dough or baked good.

In some embodiments, the present disclosure provides a method of lowering the pH of a dough, the method comprising admixing an effective amount of the composition described herein to the dough.

In some embodiments, the present disclosure provides a method of increasing organic acids in a dough, the method comprising admixing an effective amount of the composition described herein to the dough.

In some embodiments, the present disclosure provides a method of enhancing rheological properties of a dough, the method comprising admixing an effective amount of the composition described herein to the dough.

In some embodiments, the present disclosure provides a method of increasing protein degradation in a dough, the method comprising admixing an effective amount of the composition described herein to the dough.

In some embodiments, the present disclosure provides a method of increasing peptide or protein production in a dough, the method comprising admixing an effective amount of the composition described herein to the dough.

In some embodiments, the present disclosure provides a method of increasing degradation of complex and/or simple carbohydrates in a dough, the method comprising admixing an effective amount of the composition described herein to the dough.

In some embodiments, the present disclosure provides a method of increasing degradation of chemical compounds or chemical precursors in a dough, the method comprising admixing an effective amount of the composition described herein to the dough.

In some embodiments, the present disclosure provides a method of increasing the flavor or aroma of a dough, the method comprising admixing an effective amount of the composition described herein to the dough.

In some embodiments, the present disclosure provides a method of increasing leavening ability of a dough, the method comprising admixing an effective amount of the composition described herein to the dough.

In some embodiments, the present disclosure provides a method of increasing nutritional quality of a dough, the method comprising admixing an effective amount of the composition described herein to the dough. In some embodiments, the method reduces the glycemic index of the dough or a baked food product of the dough. In some embodiments, the method reduces glutens in the dough or a baked food product of the dough.

In some embodiments, the present disclosure provides a method of modulating activity of one or more microorganisms in a dough, the method comprising admixing an effective amount of the composition described herein to the dough.

In some embodiments, the present disclosure provides a method for improving fermentation of a dough, comprising: admixing an effective amount of a composition comprising a purified population of one or more microorganisms comprising a nucleic acid sequence that shares at least 97% sequence identity with a nucleic acid sequence selected from SEQ ID NOs: 1-272 to the dough.

In some embodiments, the present disclosure provides a method for increasing the shelf-life of a dough, comprising: admixing an effective amount of a composition comprising a purified population of one or more microorganisms comprising a nucleic acid sequence that shares at least 97% sequence identity with a nucleic acid sequence selected from SEQ ID NOs: 1-272 to the dough.

In some embodiments, the present disclosure provides a method of enhancing rheological properties of a dough, the method comprising: admixing an effective amount of a composition comprising a purified population of one or more microorganisms comprising a nucleic acid sequence that shares at least 97% sequence identity with a nucleic acid sequence selected from SEQ ID NOs: 1-272 to the dough.

In some embodiments, the present disclosure provides a method for increasing the shelf-life of a baked food product, comprising: admixing an effective amount of a composition comprising a purified population of one or more microorganisms comprising a nucleic acid sequence that shares at least 97% sequence identity with a nucleic acid sequence selected from SEQ ID NOs: 1-272 to a dough, wherein the admixture results in the baked food product with an increased shelf-life.

In some embodiments, the method comprises incubating the admixture for a period of time. In some embodiments, the admixture is incubated for at least 15 minutes, at least 30 minutes, at least 1 hour, at least 2 hours, at least 6 hours, at least 12 hours, at least 24 hours, at least 36 hours, at least 48 hours, at least 60 hours, at least 72 hours, at least 84 hours, at least 96 hours, at least 108 hours, or at least 120 hours.

BRIEF DESCRIPTION OF THE FIGURES

The accompanying figures, which are incorporated herein and form a part of the specification, illustrate some, but not the only or exclusive, example embodiments and/or features of the present invention. It is intended that the embodiments and figures disclosed herein are to be considered illustrative rather than limiting.

DETAILED DESCRIPTION

Figure 1A:
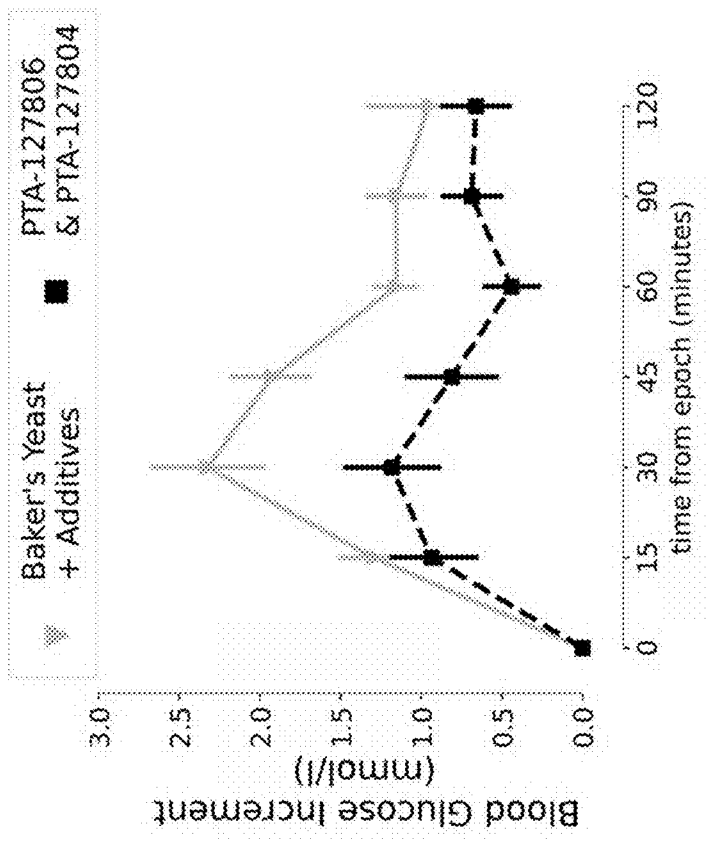
FIG. 1A shows the blood glucose level across time from consuming bread produced from using baker's yeast plus additives or a two strain inoculant comprising *Fructilactobacillus sanfranciscensis* (PTA-127806) and *Saccharomyces cerevisiae* (PTA-127804).

The present disclosure provides isolated microorganisms, including novel strains of the microorganisms, microbial consortia, and compositions comprising the same, which can replicate both the organoleptic and health benefits observed with sourdough microbial communities in a safe, affordable, and consistent way at scale.

These microorganisms can be used in methods that include, inter alia, the improved fermentation of dough resulting in improved sensory evaluation, health, and shelf-life of the fermented food product. In some embodiments, the disclosure provides methods of improving the digestion, glycemic index, immunogenic gluten content, texture, aroma, flavor, and shelf-life of fermented foods through improved dough fermentation.

DEFINITIONS

Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa unless the content clearly dictates otherwise. In the event that any description of a term set forth conflicts with any document incorporated herein by reference, the description of the term set forth below shall control.

The terms "a", "an", and "the", as used herein, include plural references unless the context clearly dictates otherwise. As such, the terms "a," "an," "one or more," and "at least one" are used interchangeably herein. In addition, reference to "an element" by the indefinite article "a" or "an" does not exclude the possibility that more than one of the elements is present, unless the context clearly requires that there is one and only one of the elements.

Throughout this application, the term "about" is used to indicate that a value includes the inherent variation of error for the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated.

As used in this application, the terms "about" and "approximately" are used as equivalents.

The term "and/or", as used herein, refers to and encompasses any and all possible combinations of one or more of the associated listed items, as well as the lack of combinations when interpreted in the alternative ("or").

The term "between", as used in a phrase as such "between A and B" or "between A-B" refers to a range including both A and B.

The terms "comprise" and its grammatical equivalents, as used herein, specify the presence of stated features, integers, steps, operations, elements, and/or components, but do not preclude the presence or addition of one or more other features, integers, steps, operations, elements, components, and/or groups thereof.

The terms "including", "includes", "included", and other forms, as used herein, are not limiting.

As used herein, the term "sequence identity" refers to the extent to which two optimally aligned polynucleotides or polypeptide sequences are invariant throughout a window of alignment of residues, e.g., nucleotides or amino acids. An "identity fraction" for aligned segments of a test sequence and a reference sequence is the number of identical residues which are shared by the two aligned sequences divided by the total number of residues in the reference sequence segment, i.e., the entire reference sequence or a smaller defined part of the reference sequence. "Percent identity" is the identity fraction times 100. Comparison of sequences to determine percent identity can be accomplished by a number of well-known methods, including for example by using mathematical algorithms, such as, for example, those in the BLAST suite of sequence analysis programs. Unless noted otherwise, the term "sequence identity" in the claims refers to sequence identity as calculated by Clustal Omega® using default parameters.

The term "composition" relates to a composition comprising one or more of the microorganisms described herein and optionally one or more acceptable carriers. In some embodiments, the composition is a non-naturally occurring composition. In some embodiments, the composition is a food-grade composition. In some embodiments, the composition comprises additional components, such as stabilizers, bread improvers, and preservatives. In some embodiments, the composition is a starter culture, a dough, or a food product (such as a baked good).

The term "starter culture" refers to a preparation of living microorganisms that are added to foods to help start fermentation. The starter culture can comprise a single type of microorganism or a mixture of two or more microorganisms. The microorganisms can be bacteria, yeasts, or molds. Starter cultures are used to produce fermented foods by accelerating the fermentation process and changing the chemical composition and sensory properties of the substrate to create a more homogeneous product.

The term "food product" refers to each and every product for human or animal food consumption. In some embodiments, the food product is food for human consumption. In some embodiments, the food product is a fermented food product, such as a dough or baked good. In some embodiments, the food product is a fermented dairy product.

The term "baked good" includes any and all goods made from a dough or batter and cooked by baking, frying, or deep frying, preferably by baking. In some embodiments, the baked product is produced with an acidic dough. In some embodiments, the baked good is a bread, including flatbreads, bagels, bread rolls, and the like; a cracker; a pastry product; a tart or pie; or a viennoiserie. In some embodiments, the baked product is made from a leavened dough, such as loaf bread such as toast, baguette, and the like; leavened flatbread; or viennoiserie. In some embodiments, the baked good is sourdough bread.

The term "flour" is generally known to the skilled person. In some embodiments, the flour is cereal flour, such as a wheat, rye, barley, oat, corn, rice, spelt, sorghum millet, emmer, einkorn, kamut, or buckwheat flour. In some embodiments, the flour is pastry flour, all-purpose flour, or bread flour. In some embodiments, the flour is a powder generated by grinding grains, roots, beans, nuts, or other fruits of edible plants or parts thereof.

The term "dough" is used herein in a broad sense relating to any and all mixtures comprising the components described herein. In some embodiments, the dough is a liquid dough such as a batter or a semisolid or solid dough. In some embodiments, the dough comprises at least one type of flour. In some embodiments, the dough comprises different types of flour such as a mixed wheat flour/rye flour dough. In some embodiments, the dough comprises at least 10% (w/w) flour, at least 20% (w/w) flour, at least 30% (w/w) flour, at least 40% (w/w) flour, or at least 50% (w/w) flour. In some embodiments, the dough comprises one or more of the microorganisms described herein. In some embodiments, the dough comprises glucose and/or sucrose. In some embodiments, the dough comprises one or more microorganisms described herein, flour, and water.

The term "admixing" refers to mixing a component(s) with another component(s) to homogeneity. In some embodiments, admixing comprises kneading the components. In some embodiments, admixing comprises stirring the components.

The term "shelf-life" refers to the time that the fermented dough or baked good can be stored while maintaining properties including, but not limited to, organoleptic properties, nutritional value, and safety. The safety of the fermented dough or baked goods includes, but is not limited to, competitively excluding microbial pathogens, molds, or other organisms that lead to food spoilage.

The "autolyse stage" referred to herein is defined as the resting period between the initial mixing and addition of the salt and/or leaving agent.

The "bulk stage" referred to herein is defined as first primary fermentation after the salt and leaving agent have been added.

The "portion stage" referred to herein is the dividing of the dough into individual pieces and shaping them into the final form for secondary fermentation or baking.

The term "food grade carrier or excipient" means a non-toxic, inert solid, semisolid or liquid filler, diluent, encapsulating material or formulation of any type.

Microorganisms of the Disclosure

In some embodiments, the present disclosure provides isolated microorganisms, including novel strains of microorganisms, presented in Table 1. In some embodiments, the present disclosure provides isolated whole microbial cultures of the microorganisms identified in Table 1.

In some embodiments, the present disclosure provides utilizing one or more microorganisms selected from Table 1 to produce a dough or food product (e.g. a baked good).

In some embodiments, the present disclosure provides microbial consortia comprising a combination of at least two microorganisms selected from the microorganisms identified in Table 1. In some embodiments, the consortia comprises two microorganisms, three microorganisms, four microorganisms, five microorganisms, six microorganisms, seven microorganisms, eight microorganisms, nine microorganisms, ten microorganisms, or more. In some embodiments, the microbial consortia are different microbial species or different strains of a microbial species.

The microorganisms of Table 1 were matched to their nearest taxonomic groups by utilizing classification tools such the Ribosomal Database Project (RDP) for 16S rRNA sequences and the User-friendly Nordic ITS Ectomycorrhiza (UNITE) database for ITS rRNA sequences. The 16S or 18S rRNA sequences or ITS sequences are often used for making distinctions between species and strains, in that if one of the aforementioned sequences share less than a specified percent sequence identity from a reference sequence, then the two organisms from which the sequences were obtained are said to be of different species or strains. It is known in the art that 16S rRNA contains hypervariable regions that can provide species/strain-specific signature sequences useful for bacterial identification, and that ITS sequences can also provide species/strain-specific signature sequences useful for fungal identification. In some embodiments, the microorganisms of the present disclosure are interpreted as belonging to the same species if one or more of the sequenced genes shares at least 97% sequence identity to the reference sequence.

In some embodiments, the microbial strains of the present disclosure include those that comprise a nucleic acid sequence that shares at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-272.

The isolation, identification, and culturing of microorganisms of the present disclosure can be performed using standard microbiological techniques known in the art.

In some embodiments, isolation of the microorganisms described herein is performed by streaking the specimen on a solid medium (e.g., nutrient agar plates) to obtain a single colony, which is then characterized by phenotypic traits (e.g., Gram positive/negative, cellular morphology, metabolic secretions, and the like). In some embodiments, pure isolates are obtained through repeated subculture of biological samples, each subculture followed by streaking onto solid media to obtain individual colonies or colony forming units.

In some embodiments, the microorganisms of the present disclosure are propagated through the use of a liquid growth medium under aerobic or anaerobic conditions. A medium for growing bacteria or fungi includes carbon, nitrogen, salts, minerals, vitamins, pH buffer, and other energy sources or selective agents such as those provided in (Ronald M. Atlas 2004). Suitable mediums for bacteria include, but are not limited to, MRS (De MAN, Rogosa, and Sharpe 1960) or TSB (Doyle, Mehrhof, and Ernst 1968) and suitable mediums for fungi include, but are not limited to, YPD ("YPD Media" 2010) or PDB (Eddleman n.d.).

In some embodiments, the microorganisms of the present disclosure are further preserved using common techniques in microbiology. These techniques include, but are not limited to, freeze-drying, desiccation, freeze-drying with cryoprotectants, fluid-bed drying, extrusion, spray drying, matrix encapsulation, vacuum drying, and protective packaging. In freeze-drying, also referred to as lyophilization, the microbial culture is frozen and then subjected to a vacuum to remove water by sublimation. In some embodiments, microorganisms of the present disclosure are protected by the addition of cryoprotectants including, but not limited to, glycerol, sucrose, or trehalose. In some embodiments, the microorganisms of the present disclosure are preserved through desiccation or by spray drying the microorganisms in a fine droplet followed by rapid drying by hot air or nitrogen gas. The dried microorganisms can then be stored in a protective matrix including, but not limited to, alginate or wax encapsulate beads, which can be further protected by packaging to prevent the reabsorption of moisture.

In some embodiments, the microorganisms described herein maintain viability across a broad range of environmental conditions. In some embodiments, the microorganisms described herein maintain viability in environmental conditions including, but not limited to, hypersaline, high sugar, low temperature, high temperature, and dry environments. In some embodiments, the microorganisms described herein maintain viability during a microbial preservation process such as cryopreservation, centrifugation, spray drying, or lyophilization.

In some embodiments, the microorganisms of the present disclosure, i.e., the microorganisms listed in Table 1, were obtained from sourdough starters, environments that contribute to the formation of a sourdough starter (e.g., human skin, human saliva, water, air or insects), grain-based fermentations, or grains before fermentation.

In some embodiments, a biological sample is collected from an environment or from an environment across time. In some embodiments, these environments include sourdough starters, environments that contribute to the formation of a sourdough starter (e.g., human skin, human saliva, water, air, insects), grain-based fermentations, or grains before fermentation. The biological sample is processed to detect the presence, abundance, and activity of one or more microorganisms. The sample is processed for the isolation, identification, and culturing of the microorganisms contained within. In some embodiments, isolation is performed by spreading the biological sample on solid medium to obtain single colonies, which are then propagated in a liquid medium under aerobic or anaerobic conditions. Isolated organisms are characterized by the phenotypic traits (e.g., acid tolerance, enzyme production, carbon source utilization). Each biological sample is processed to detect the presence and abundance of one or more metabolite in the sample. The environmental parameters or outcomes of the sample are recorded and included with microbial and metabolite detection information (e.g., pH, organoleptic properties, immunogenic gluten content, glycemic index). Dimensionality reduction analysis and multi-dimensional dimensionality reduction is performed individually and across all information collected, to determine the important organisms, metabolite, and environmental parameter relationships. Using the dimensionality reduction output, one or more microorganisms are selected for preparing products (e.g., ensembles, aggregates, and/or other synthetic groupings) containing the selected strains. The microorganism or group of microorganisms of interest are introduced to the environment (i.e., dough or food product). Samples are taken from the environment (i.e., dough or food product) in which the microorganisms were introduced, and the presence, abundance, and activity of the administered microorganisms are verified. From the additional samples, the presence and abundance of metabolites from the administered microorganisms are verified. From the additional samples, the desired outcomes are verified (e.g., pH, organoleptic properties, immunogenic gluten content, glycemic index).

In some embodiments, a sample or multiple samples are collected cross-sectionally or longitudinally from grain fermentations (e.g., dough) and processed to predict in silico the minimal and optimal microorganism or microbial consortia, needed to produce the desired food product, e.g., sourdough bread. In some embodiments, samples were obtained from publicly available databases and preprocessed datasets including, but not limited to, metabolomics, volatile organic compounds (VOCs), 16S rRNA, ITS rRNA, metagenomics, metatranscriptomics, ribosome profiling, and associated sample metadata. In some embodiments, the data is analyzed and integrated by tools including, but not limited to, alpha-diversity, beta-diversity, clustering analysis, network analysis, and differential abundance analysis.

In some embodiments, the sample is compared or correlated across metadata by the taxonomic or functional diversity within (alpha-diversity) each sample or across time using but not limited to the Shannon index (Tucker et al. 2017). In some embodiments, the sample is compared or correlated across metadata by the taxonomic or functional differences in composition (beta-diversity) across samples or across time by all samples using UniFrac (Lozupone and Knight 2005), Compositional Tensor Factorization (Martino et al. 2021), and/or Robust Aitchison PCA (Martino et al. 2019) performed across datatypes or within each datatype individually to form low-dimensional sample clusters (i.e. dimensionality reduction).

In some embodiments, network analysis is performed using the dimensionality reduction clusters and from network correlation analyses including all datatypes and metadata with Pearson correlations, Spearman correlations, canonical correspondence analysis (CCA), and/or partial least squares (PLS) (Meng et al. 2016; Rohart et al. 2017).

In some embodiments, the differential abundance of specific taxa or functional compositions across samples, within samples across time, or across samples and time was performed using ALDEx2 (Gloor et al. 2019), Linear Mixed Effects models (Rahman et al. 2023), and/or ANCOM-BC (Lin and Peddada 2020).

The microorganisms found below in Table 1 will be utilized in various embodiments of the present disclosure. The 16S or ITS sequences referred to in Table 1 were determined by ITS or 16S Illumina short-read sequencing. These microorganisms are predicted to produce a desired dough or food product, e.g., sourdough.

TABLE 1

Microorganisms of the Disclosure

| Predicted Genus Species | 16S or ITS |
|---|---|
| *Latilactobacillus sakei*† | SEQ ID NO: 1 |
| *Leuconostoc mesenteroides*† | SEQ ID NO: 2 |
| *Latilactobacillus curvatus*† | SEQ ID NO: 3 |
| *Lactobacillus sanfranciscensis* | SEQ ID NO: 4 |
| *Pediococcus inopinatus* | SEQ ID NO: 5 |
| *Lactobacillus paralimentarius* | SEQ ID NO: 6 |
| *Lactobacillus sakei* | SEQ ID NO: 7 |
| *Lactobacillus brevis* | SEQ ID NO: 8 |
| *Lactobacillus plantarum* | SEQ ID NO: 9 |
| *Pediococcus pentosaceus* | SEQ ID NO: 10 |
| *Lactobacillus brevis* | SEQ ID NO: 11 |
| *Pediococcus parvulus* | SEQ ID NO: 12 |
| *Acetobacter tropicalis* | SEQ ID NO: 13 |
| *Acetobacter orleanensis* | SEQ ID NO: 14 |
| *Lactobacillus hilgardii* | SEQ ID NO: 15 |
| *Lactobacillus parabuchneri* | SEQ ID NO: 16 |
| *Lactobacillus sanfranciscensis*† | SEQ ID NO: 17 |
| *Lactobacillus coryniformis* | SEQ ID NO: 18 |

TABLE 1-continued

Microorganisms of the Disclosure

| Predicted Genus Species | 16S or ITS |
|---|---|
| *Leuconostoc mesenteroides* | SEQ ID NO: 19 |
| *Lactobacillus casei* | SEQ ID NO: 20 |
| *Lactobacillus sanfranciscensis*[†] | SEQ ID NO: 21 |
| *Lactobacillus brevis* | SEQ ID NO: 22 |
| *Leuconostoc gelidum* | SEQ ID NO: 23 |
| *Lactococcus* sp. | SEQ ID NO: 24 |
| *Paracoccus laeviglucosivorans* | SEQ ID NO: 25 |
| *Acetobacter lovaniensis* | SEQ ID NO: 26 |
| *Lactobacillus sanfranciscensis*[††] | SEQ ID NO: 27 |
| *Leuconostoc gelidum*[††] | SEQ ID NO: 28 |
| *Lactobacillus sakei*[††] | SEQ ID NO: 29 |
| *Leuconostoc gelidum*[††] | SEQ ID NO: 30 |
| *Leuconostoc gelidum* | SEQ ID NO: 31 |
| *Lactobacillus sakei* | SEQ ID NO: 32 |
| *Lactobacillus sakei* | SEQ ID NO: 33 |
| *Lactobacillus perolens* | SEQ ID NO: 34 |
| *Lactobacillus sakei* | SEQ ID NO: 35 |
| *Secundilactobacillus* sp. | SEQ ID NO: 36 |
| *Lactobacillus sanfranciscensis*[†] | SEQ ID NO: 37 |
| *Gluconobacter thailandicus* | SEQ ID NO: 38 |
| *Leuconostoc mesenteroides*[††] | SEQ ID NO: 39 |
| *Lactobacillus rossiae* | SEQ ID NO: 40 |
| *Levilactobacillus brevis*[†] | SEQ ID NO: 41 |
| *Gluconobacter roseus* | SEQ ID NO: 42 |
| *Leucobacter albus* | SEQ ID NO: 43 |
| *Acetobacter persici* | SEQ ID NO: 44 |
| *Lactobacillus sakei*[††] | SEQ ID NO: 45 |
| *Lactobacillus plantarum*[††] | SEQ ID NO: 46 |
| *Leuconostoc gelidum*[††] | SEQ ID NO: 47 |
| *Paracoccus aminophilus* | SEQ ID NO: 48 |
| *Lactobacillus fermentum* | SEQ ID NO: 49 |
| *Leuconostoc gelidum*[††] | SEQ ID NO: 50 |
| *Lactobacillus sanfranciscensis* | SEQ ID NO: 51 |
| *Lactobacillus* sp. | SEQ ID NO: 52 |
| *Psychrobacter fulvigenes* | SEQ ID NO: 53 |
| *Weissella confusa* | SEQ ID NO: 54 |
| *Lactobacillus sakei* | SEQ ID NO: 55 |
| *Lactobacillus sanfranciscensis* | SEQ ID NO: 56 |
| *Fenollaria massiliensis* | SEQ ID NO: 57 |
| *Lactobacillus brevis* | SEQ ID NO: 58 |
| *Peptoniphilus* sp. | SEQ ID NO: 59 |
| *Lactobacillus brevis*[††] | SEQ ID NO: 60 |
| *Corynebacterium tuberculostearicum* | SEQ ID NO: 61 |
| *Lactobacillus sakei* | SEQ ID NO: 62 |
| *Lactobacillus acetotolerans* | SEQ ID NO: 63 |
| *Lactobacillus brevis* | SEQ ID NO: 64 |
| *Leuconostoc mesenteroides*[††] | SEQ ID NO: 65 |
| *Ezakiella coagulans* | SEQ ID NO: 66 |
| *Leuconostoc mesenteroides*[††] | SEQ ID NO: 67 |
| *Lactobacillus brevis*[††] | SEQ ID NO: 68 |
| *Pediococcus parvulus* | SEQ ID NO: 69 |
| *Eubacterium* sp. | SEQ ID NO: 70 |
| *Pediococcus parvulus* | SEQ ID NO: 71 |
| *Corynebacterium* sp. | SEQ ID NO: 72 |
| *Lactobacillus plantarum* | SEQ ID NO: 73 |
| *Lactobacillus pontis* | SEQ ID NO: 74 |
| *Micrococcus antarcticus* | SEQ ID NO: 75 |
| *Paracoccus marinus* | SEQ ID NO: 76 |
| *Lactobacillus brevis* | SEQ ID NO: 77 |
| *Anaerococcus nagyae* | SEQ ID NO: 78 |
| *Lactobacillus manihotivorans* | SEQ ID NO: 79 |
| *Lactobacillus acidophilus* | SEQ ID NO: 80 |
| *Lactobacillus sakei* | SEQ ID NO: 81 |
| *Lactobacillus sanfranciscensis* | SEQ ID NO: 82 |
| *Lactobacillus sanfranciscensis* | SEQ ID NO: 83 |
| *Lactobacillus helveticus* | SEQ ID NO: 84 |
| *Gluconobacter albidus* | SEQ ID NO: 85 |
| *Ezakiella peruensis* | SEQ ID NO: 86 |
| *Lactococcus* sp. | SEQ ID NO: 87 |
| *Lactobacillus paralimentarius* | SEQ ID NO: 88 |
| *Ruminococcus bicirculans* | SEQ ID NO: 89 |
| *Corynebacterium macginleyi* | SEQ ID NO: 90 |
| *Faecalibacterium* sp. | SEQ ID NO: 91 |
| *Lagierella massiliensis* | SEQ ID NO: 92 |
| *Corynebacterium kroppenstedtii* | SEQ ID NO: 93 |
| *Rothia* sp. | SEQ ID NO: 94 |

TABLE 1-continued

Microorganisms of the Disclosure

| Predicted Genus Species | 16S or ITS |
|---|---|
| *Lactobacillus perolens* | SEQ ID NO: 95 |
| *Pediococcus parvulus* | SEQ ID NO: 96 |
| *Lactobacillus sakei* | SEQ ID NO: 97 |
| *Lactobacillus siliginis* | SEQ ID NO: 98 |
| *Lactobacillus sakei* | SEQ ID NO: 99 |
| *Corynebacterium pseudodiphtheriticum* | SEQ ID NO: 100 |
| *Peptoniphilus* sp. | SEQ ID NO: 101 |
| *Pediococcus parvulus* | SEQ ID NO: 102 |
| *Lactobacillus hilgardii* | SEQ ID NO: 103 |
| *Lactobacillus sakei* | SEQ ID NO: 104 |
| *Lactobacillus brevis* | SEQ ID NO: 105 |
| *Clostridium* sp. | SEQ ID NO: 106 |
| *Lactobacillus* sp. | SEQ ID NO: 107 |
| *Corynebacterium simulans* | SEQ ID NO: 108 |
| *Rothia* sp. | SEQ ID NO: 109 |
| *Brevibacterium luteolum* | SEQ ID NO: 110 |
| *Lactobacillus sakei* | SEQ ID NO: 111 |
| *Acidiphilium organovorum* | SEQ ID NO: 112 |
| *Lactobacillus plantarum* | SEQ ID NO: 113 |
| *Peptoniphilus senegalensis* | SEQ ID NO: 114 |
| *Lactobacillus paralimentarius* | SEQ ID NO: 115 |
| *Anaerococcus octavius* | SEQ ID NO: 116 |
| *Pediococcus parvulus* | SEQ ID NO: 117 |
| *Lactobacillus plantarum* | SEQ ID NO: 118 |
| *Rothia dentocariosa* | SEQ ID NO: 119 |
| *Lactobacillus coryniformis* | SEQ ID NO: 120 |
| *Lactobacillus casei* | SEQ ID NO: 121 |
| *Corynebacterium* sp. | SEQ ID NO: 122 |
| *Leuconostoc carnosum* | SEQ ID NO: 123 |
| *Lactobacillus selangorensis* | SEQ ID NO: 124 |
| *Lactobacillus sakei* | SEQ ID NO: 125 |
| *Lactobacillus sakei* | SEQ ID NO: 126 |
| *Lactobacillus sanfranciscensis* | SEQ ID NO: 127 |
| *Weissella cibaria* | SEQ ID NO: 128 |
| *Pediococcus pentosaceus*[††] | SEQ ID NO: 129 |
| *Lactobacillus sakei* | SEQ ID NO: 130 |
| *Lactobacillus fuchuensis* | SEQ ID NO: 131 |
| *Corynebacterium casei* | SEQ ID NO: 132 |
| *Pediococcus argentinicus* | SEQ ID NO: 133 |
| *Lactobacillus rossiae* | SEQ ID NO: 134 |
| *Lactobacillus siliginis* | SEQ ID NO: 135 |
| *Pediococcus pentosaceus*[††] | SEQ ID NO: 136 |
| *Corynebacterium efficiens* | SEQ ID NO: 137 |
| *Anaerococcus* sp. | SEQ ID NO: 138 |
| *Dermacoccus profundi* | SEQ ID NO: 139 |
| *Eubacterium yurii* | SEQ ID NO: 140 |
| *Cutibacterium acnes* | SEQ ID NO: 141 |
| *Corynebacterium glucuronolyticum* | SEQ ID NO: 142 |
| *Lactobacillus sanfranciscensis* | SEQ ID NO: 143 |
| *Collinsella* sp. | SEQ ID NO: 144 |
| *Stomatobaculum longum* | SEQ ID NO: 145 |
| *Bacteriovorax stolpii* | SEQ ID NO: 146 |
| *Rothia* sp. | SEQ ID NO: 147 |
| *Corynebacterium faecale* | SEQ ID NO: 148 |
| *Lactococcus* sp. | SEQ ID NO: 149 |
| *Armatimonas rosea* | SEQ ID NO: 150 |
| *Lactobacillus sakei* | SEQ ID NO: 151 |
| *Acidiphilium organovorum* | SEQ ID NO: 152 |
| *Lactobacillus* sp. | SEQ ID NO: 153 |
| *Lactobacillus sakei* | SEQ ID NO: 154 |
| *Anaerotignum lactatifermentans* | SEQ ID NO: 155 |
| *Brachybacterium conglomeratum* | SEQ ID NO: 156 |
| *Saccharomyces* sp. | SEQ ID NO: 157 |
| *Kazachstania exigua* | SEQ ID NO: 158 |
| *Kazachstania humilis* | SEQ ID NO: 159 |
| *Saccharomyces paradoxus* | SEQ ID NO: 160 |
| *Saccharomyces* sp. | SEQ ID NO: 161 |
| *Kazachstania servazzii* | SEQ ID NO: 162 |
| *Saccharomyces cerevisiae*[†] | SEQ ID NO: 163 |
| *Kazachstania humilis* | SEQ ID NO: 164 |
| *Pichia fermentans* | SEQ ID NO: 165 |
| *Naumovozyma castellii* | SEQ ID NO: 166 |
| *Candida sake* | SEQ ID NO: 167 |
| *Kazachstania humilis* | SEQ ID NO: 168 |
| *Kazachstania unispora* | SEQ ID NO: 169 |
| *Saccharomyces* sp. | SEQ ID NO: 170 |

TABLE 1-continued

Microorganisms of the Disclosure

| Predicted Genus Species | 16S or ITS |
|---|---|
| *Kazachstania barnettii* | SEQ ID NO: 171 |
| *Kazachstania humilis* | SEQ ID NO: 172 |
| *Pichia fermentans* | SEQ ID NO: 173 |
| *Saccharomyces pastorianus* | SEQ ID NO: 174 |
| *Kazachstania bulderi* | SEQ ID NO: 175 |
| *Saccharomyces cerevisiae*†† | SEQ ID NO: 176 |
| *Wickerhamomyces anomalus* | SEQ ID NO: 177 |
| *Wickerhamomyces anomalus* | SEQ ID NO: 178 |
| *Pichia membranifaciens* | SEQ ID NO: 179 |
| *Wickerhamomyces anomalus* | SEQ ID NO: 180 |
| *Candida sake* | SEQ ID NO: 181 |
| *Wickerhamomyces anomalus* | SEQ ID NO: 182 |
| *Saccharomyces cerevisiae*†† | SEQ ID NO: 183 |
| *Pichia kudriavzevii* | SEQ ID NO: 184 |
| *Wickerhamomyces anomalus* | SEQ ID NO: 185 |
| *Saccharomyces paradoxus* | SEQ ID NO: 186 |
| *Hanseniaspora* sp. | SEQ ID NO: 187 |
| *Pichia membranifaciens* | SEQ ID NO: 188 |
| *Penicillium* sp. | SEQ ID NO: 189 |
| *Hanseniaspora* sp. | SEQ ID NO: 190 |
| *Meyerozyma guilliermondii* | SEQ ID NO: 191 |
| *Saccharomyces* sp. | SEQ ID NO: 192 |
| *Saccharomyces pastorianus* | SEQ ID NO: 193 |
| *Wickerhamomyces anomalus* | SEQ ID NO: 194 |
| *Candida glabrata* | SEQ ID NO: 195 |
| *Debaryomyces delbrueckii* | SEQ ID NO: 196 |
| *Kazachstania naganishii* | SEQ ID NO: 197 |
| *Pichia cephalocereana* | SEQ ID NO: 198 |
| *Saccharomyces paradoxus* | SEQ ID NO: 199 |
| *Saccharomyces* sp. | SEQ ID NO: 200 |
| *Pichia kudriavzevii* | SEQ ID NO: 201 |
| *Pichia kudriavzevii* | SEQ ID NO: 202 |
| *Kazachstania servazzii* | SEQ ID NO: 203 |
| *Xeromyces bisporus* | SEQ ID NO: 204 |
| *Aspergillus* sp. | SEQ ID NO: 205 |
| *Xeromyces bisporus* | SEQ ID NO: 206 |
| *Saccharomyces cerevisiae*† | SEQ ID NO: 207 |
| *Pichia cephalocereana* | SEQ ID NO: 208 |
| *Kazachstania humilis* | SEQ ID NO: 209 |
| *Saccharomyces cerevisiae*†† | SEQ ID NO: 210 |
| *Saccharomyces paradoxus* | SEQ ID NO: 211 |
| *Pichia kudriavzevii* | SEQ ID NO: 212 |
| *Kazachstania servazzii* | SEQ ID NO: 213 |
| *Penicillium* sp. | SEQ ID NO: 214 |
| *Penicillium* sp. | SEQ ID NO: 215 |
| *Aspergillus intermedius* | SEQ ID NO: 216 |
| *Pichia kudriavzevii* | SEQ ID NO: 217 |
| *Penicillium* sp. | SEQ ID NO: 218 |
| *Candida glabrata* | SEQ ID NO: 219 |
| *Penicillium tarraconense* | SEQ ID NO: 220 |
| *Penicillium* sp. | SEQ ID NO: 221 |
| *Candida parapsilosis* | SEQ ID NO: 222 |
| *Candida glabrata* | SEQ ID NO: 223 |
| *Aspergillus* sp. | SEQ ID NO: 224 |
| *Nakazawaea holstii* | SEQ ID NO: 225 |
| *Aspergillus* sp. | SEQ ID NO: 226 |
| *Phaeococcomyces* sp. | SEQ ID NO: 227 |
| *Pichia kudriavzevii* | SEQ ID NO: 228 |
| *Debaryomyces* sp. | SEQ ID NO: 229 |
| *Cephaloascus albidus* | SEQ ID NO: 230 |
| *Pichia kudriavzevii* | SEQ ID NO: 231 |
| *Saccharomyces cerevisiae*†† | SEQ ID NO: 232 |
| *Saccharomyces cerevisiae*†† | SEQ ID NO: 233 |
| *Aspergillus* sp. | SEQ ID NO: 234 |
| *Saccharomyces cerevisiae*†† | SEQ ID NO: 235 |
| *Penicillium* sp. | SEQ ID NO: 236 |
| *Eremothecium coryli* | SEQ ID NO: 237 |
| *Hanseniaspora mollemarum* | SEQ ID NO: 238 |
| *Cyberlindnera fabianii* | SEQ ID NO: 239 |
| *Kazachstania humilis* | SEQ ID NO: 240 |
| *Saccharomyces paradoxus* | SEQ ID NO: 241 |
| *Saccharomyces cerevisiae*†† | SEQ ID NO: 242 |
| *Saccharomycetales* sp. | SEQ ID NO: 243 |
| *Saccharomyces* sp. | SEQ ID NO: 244 |
| *Penicillium* sp. | SEQ ID NO: 245 |
| *Saccharomyces pastorianus* | SEQ ID NO: 246 |
| *Saccharomyces paradoxus* | SEQ ID NO: 247 |
| *Candida* sp. | SEQ ID NO: 248 |
| *Wickerhamomyces anomalus* | SEQ ID NO: 249 |
| *Aspergillus penicillioides* | SEQ ID NO: 250 |
| *Candida sake* | SEQ ID NO: 251 |
| *Pichia norvegensis* | SEQ ID NO: 252 |
| *Saccharomyces paradoxus* | SEQ ID NO: 253 |
| *Aspergillus* sp. | SEQ ID NO: 254 |
| *Candida sake*†† | SEQ ID NO: 255 |
| *Candida* sp.†† | SEQ ID NO: 256 |
| *Kazachstania* sp. | SEQ ID NO: 257 |
| *Pichia cephalocereana* | SEQ ID NO: 258 |
| *Saccharomyces paradoxus* | SEQ ID NO: 259 |
| *Candida sake*†† | SEQ ID NO: 260 |
| *Pichia kudriavzevii* | SEQ ID NO: 261 |
| *Kazachstania humilis* | SEQ ID NO: 262 |
| *Penicillium* sp. | SEQ ID NO: 263 |
| *Wickerhamomyces anomalus* | SEQ ID NO: 264 |
| *Penicillium* sp. | SEQ ID NO: 265 |
| *Penicillium* sp. | SEQ ID NO: 266 |

†Isolate
††Enrichment

Some microorganisms described in the present disclosure were deposited with the ATCC Patent Depository located at 10801 University Boulevard, Manassas, Virginia 20110, USA. The deposits were made under the terms of the Budapest Treaty on the International Recognition of the Deposit of Microorganisms for the Purposes of Patent Procedure. The ATCC Patent Depository accession numbers and corresponding dates of deposit for the aforementioned Budapest Treaty deposits are provided in Table 2 below.

TABLE 2

Budapest Treaty Deposits of the Disclosure

| Taxonomic Designation | Strain Designation | Short 16S/ITS SEQ ID NO[1] | Long 16S/ITS SEQ ID NO[2] | Patent Deposit No. | Patent Deposit Date |
|---|---|---|---|---|---|
| *Saccharomyces cerevisiae* | A5Y | 207 | 267 | PTA-127804 | Aug. 8, 2024 |
| *Kazachstania humilis* | S1-3 | 269* | 268 | PTA-127805 | Aug. 8, 2024 |
| *Fructilactobacillus sanfranciscensis* | H11B | 4 | 270 | PTA-127806 | Aug. 8, 2024 |
| *Pediococcus pentosaceus* | S1-1 | 10 | 271 | PTA-127807 | Aug. 8, 2024 |
| *Levilactobacillus brevis* | S1-2 | 8 | 272 | PTA-127808 | Aug. 8, 2024 |

[1]16S/ITS sequences were determined by ITS or 16S Illumina short-read sequencing
[2]16S/ITS sequences were determined amplicon 16S and ITS long Sanger sequencing
*SEQ ID NO: 269 is the reverse complement of SEQ ID NO: 159

In some embodiments, the isolated microbial strain is selected from any one of the microbial strains listed in Table 1. In some embodiments, the isolated microbial strain is selected from the group consisting of: *Saccharomyces cerevisiae* deposited as PTA-127804, *Kazachstania humilis* deposited as PTA-127805, *Fructilactobacillus sanfranciscensis* deposited as PTA-127806, *Pediococcus pentosaceus* deposited as PTA-127807, and *Levilactobacillus brevis* deposited as PTA-127808. In some embodiments, the isolated microbial strain is used to produce a starter culture, dough, or food product (e.g., a baked good).

Compositions

In some embodiments, the present disclosure provides compositions comprising the microorganisms described herein. In some embodiments, the composition is a starter culture, a dough, or a food product (e.g., a baked good). In some embodiments, the composition is a sourdough.

In some embodiments, the composition is a starter culture for bakery good production comprising one or more of the microorganisms described in Table 1. In some embodiments, the composition is a starter culture for bakery good production comprising one or more microorganisms with a nucleic acid sequence sharing at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-272. In some embodiments, the composition is a starter culture for bakery good production comprising one or more microorganisms with a nucleic acid sequence selected from any one of SEQ ID NOs: 1-272.

In some embodiments, the composition is a dough product comprising one or more of the microorganisms described in Table 1. In some embodiments, the composition is a dough product comprising one or more microorganisms with a nucleic acid sequence sharing at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-272. In some embodiments, the composition is dough product comprising one or more microorganisms with a nucleic acid sequence selected from any one of SEQ ID NOs: 1-272.

In some embodiments, the composition is a food product comprising one or more of the microorganisms described in Table 1. In some embodiments, the composition is a food product comprising one or more microorganisms with a nucleic acid sequence sharing at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-272. In some embodiments, the composition is food product comprising one or more microorganisms with a nucleic acid sequence selected from any one of SEQ ID NOs: 1-272.

In some embodiments, the composition is a sourdough comprising one or more of the microorganisms described in Table 1. In some embodiments, the composition is a sourdough comprising one or more microorganisms with a nucleic acid sequence sharing at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-272. In some embodiments, the composition is sourdough comprising one or more microorganisms with a nucleic acid sequence selected from any one of SEQ ID NOs: 1-272.

In some embodiments, the composition comprises one or more isolated microbial strains selected from the group consisting of: *Saccharomyces cerevisiae* deposited as PTA-127804, *Kazachstania humilis* deposited as PTA-127805, *Fructilactobacillus sanfranciscensis* deposited as PTA-127806, *Pediococcus pentosaceus* deposited as PTA-127807, and *Levilactobacillus brevis* deposited as PTA-127808. In some embodiments, the composition is a starter culture, dough, or food product (e.g., a baked good).

In some embodiments, the composition comprises *Saccharomyces cerevisiae*. In some embodiments, the composition comprises *Saccharomyces cerevisiae*, wherein the *Saccharomyces cerevisiae* comprises an ITS nucleic acid sequence sharing at least 97%, at least 98%, at least 99%, or 100% sequence identity to SEQ ID NO: 207. In some embodiments, the composition comprises *Saccharomyces cerevisiae* as deposited as PTA-127804. In some embodiments, the composition is a starter culture, dough, or food product (e.g., a baked good).

In some embodiments, the composition comprises *Saccharomyces cerevisiae*. In some embodiments, the composition comprises *Saccharomyces cerevisiae*, wherein the *Saccharomyces cerevisiae* comprises an ITS nucleic acid sequence sharing at least 97%, at least 98%, at least 99%, or 100% sequence identity to SEQ ID NO: 267. In some embodiments, the composition comprises *Saccharomyces cerevisiae* as deposited as PTA-127804. In some embodiments, the composition is a starter culture, dough, or food product (e.g., a baked good).

In some embodiments, the composition comprises *Kazachstania humilis*. In some embodiments, the composition comprises *Kazachstania humilis*, wherein the *Kazachstania humilis* comprises an ITS nucleic acid sequence sharing at least 97%, at least 98%, at least 99%, or 100% sequence identity to SEQ ID NO: 159. In some embodiments, the composition comprises *Kazachstania humilis* as deposited as PTA-127805. In some embodiments, the composition is a starter culture, dough, or food product (e.g., a baked good).

In some embodiments, the composition comprises *Kazachstania humilis*. In some embodiments, the composition comprises *Kazachstania humilis*, wherein the *Kazachstania humilis* comprises an ITS nucleic acid sequence sharing at least 97%, at least 98%, at least 99%, or 100% sequence identity to SEQ ID NO: 268. In some embodiments, the composition comprises *Kazachstania humilis* as deposited as PTA-127805. In some embodiments, the composition is a starter culture, dough, or food product (e.g., a baked good).

In some embodiments, the composition comprises *Kazachstania humilis*. In some embodiments, the composition comprises *Kazachstania humilis*, wherein the *Kazachstania humilis* comprises an ITS nucleic acid sequence sharing at least 97%, at least 98%, at least 99%, or 100% sequence identity to SEQ ID NO: 269. In some embodiments, the composition comprises *Kazachstania humilis* as deposited as PTA-127805. In some embodiments, the composition is a starter culture, dough, or food product (e.g., a baked good).

In some embodiments, the composition comprises *Fructilactobacillus sanfranciscensis*. In some embodiments, the composition comprises *Fructilactobacillus sanfranciscensis*, wherein the *Fructilactobacillus sanfranciscensis* comprises a 16S nucleic acid sequence sharing at least 97%, at least 98%, at least 99%, or 100% sequence identity to SEQ ID NO: 4. In some embodiments, the composition comprises *Fructilactobacillus sanfranciscensis* as deposited as PTA-127806. In some embodiments, the composition is a starter culture, dough, or food product (e.g., a baked good).

In some embodiments, the composition comprises *Fructilactobacillus sanfranciscensis*. In some embodiments, the composition comprises *Fructilactobacillus sanfranciscensis*, wherein the *Fructilactobacillus sanfranciscensis* comprises a 16S nucleic acid sequence sharing at least 97%, at least 98%, at least 99%, or 100% sequence identity to SEQ ID NO: 270. In some embodiments, the composition comprises *Fructilactobacillus sanfranciscensis* as deposited as PTA-127806. In some embodiments, the composition is a starter culture, dough, or food product (e.g., a baked good).

In some embodiments, the composition comprises *Pediococcus pentosaceus*. In some embodiments, the composition comprises *Pediococcus pentosaceus*, wherein the *Pediococcus pentosaceus* comprises a 16S nucleic acid sequence sharing at least 97%, at least 98%, at least 99%, or 100% sequence identity to SEQ ID NO: 10. In some embodiments, the composition comprises *Pediococcus pentosaceus* as deposited as PTA-127807. In some embodiments, the composition is a starter culture, dough, or food product (e.g., a baked good).

In some embodiments, the composition comprises *Pediococcus pentosaceus*. In some embodiments, the composition comprises *Pediococcus pentosaceus*, wherein the *Pediococcus pentosaceus* comprises a 16S nucleic acid sequence sharing at least 97%, at least 98%, at least 99%, or 100% sequence identity to SEQ ID NO: 271. In some embodiments, the composition comprises *Pediococcus pentosaceus* as deposited as PTA-127807. In some embodiments, the composition is a starter culture, dough, or food product (e.g., a baked good).

In some embodiments, the composition comprises *Levilactobacillus brevis*. In some embodiments, the composition comprises *Levilactobacillus brevis*, wherein the *Levilactobacillus brevis* comprises a 16S nucleic acid sequence sharing at least 97%, at least 98%, at least 99%, or 100% sequence identity to SEQ ID NO: 8. In some embodiments, the composition comprises *Levilactobacillus brevis* as deposited as PTA-127808. In some embodiments, the composition is a starter culture, dough, or food product (e.g., a baked good).

In some embodiments, the composition comprises *Levilactobacillus brevis*. In some embodiments, the composition comprises *Levilactobacillus brevis*, wherein the *Levilactobacillus brevis* comprises a 16S nucleic acid sequence sharing at least 97%, at least 98%, at least 99%, or 100% sequence identity to SEQ ID NO: 272. In some embodiments, the composition comprises *Levilactobacillus brevis* as deposited as PTA-127808. In some embodiments, the composition is a starter culture, dough, or food product (e.g., a baked good).

In some embodiments, the composition comprises: (a) *Saccharomyces cerevisiae* with an ITS nucleic acid sequence sharing at least 97%, at least 98%, at least 99%, or 100% sequence identity to SEQ ID NO: 207 or SEQ ID NO: 267; (b) *Kazachstania humilis* with an ITS nucleic acid sequence sharing at least 97%, at least 98%, at least 99%, or 100% sequence identity to SEQ ID NO: 159, SEQ ID NO: 268, or SEQ ID NO: 269; (c) *Fructilactobacillus sanfranciscensis* with a 16S nucleic acid sequence sharing at least 97%, at least 98%, at least 99%, or 100% sequence identity to SEQ ID NO: 4 or SEQ ID NO: 270; (d) *Pediococcus pentosaceus* with a 16S nucleic acid sequence sharing at least 97%, at least 98%, at least 99%, or 100% sequence identity to SEQ ID NO: 10 or SEQ ID NO: 271; and/or (e) *Levilactobacillus brevis* with a 16S nucleic acid sequence sharing at least 97%, at least 98%, at least 99%, or 100% sequence identity to SEQ ID NO: 8 or SEQ ID NO: 272. In some embodiments, the composition is a starter culture, dough, or food product (e.g., a baked good).

In some embodiments, the composition comprises: (a) a yeast with an ITS nucleic acid sequence sharing at least 97%, at least 98%, at least 99%, or 100% sequence identity to SEQ ID NO: 207 or SEQ ID NO: 267; (b) a yeast with an ITS nucleic acid sequence sharing at least 97%, at least 98%, at least 99%, or 100% sequence identity to SEQ ID NO: 159, SEQ ID NO: 268, or SEQ ID NO: 269; (c) a bacterium with a 16S nucleic acid sequence sharing at least 97%, at least 98%, at least 99%, or 100% sequence identity to SEQ ID NO: 4 or SEQ ID NO: 270; (d) a bacterium with a 16S nucleic acid sequence sharing at least 97%, at least 98%, at least 99%, or 100% sequence identity to SEQ ID NO: 10 or SEQ ID NO: 271; and/or (e) a bacterium with a 16S nucleic acid sequence sharing at least 97%, at least 98%, at least 99%, or 100% sequence identity to SEQ ID NO: 8 or SEQ ID NO: 272. In some embodiments, the composition is a starter culture, dough, or food product (e.g., a baked good).

In some embodiments, the composition comprises: (a) a *Saccharomyces cerevisiae* as deposited as PTA-127804; (b) a *Kazachstania humilis* as deposited as PTA-127805; (c) a *Fructilactobacillus sanfranciscensis* as deposited as PTA-127806; (d) a *Pediococcus pentosaceus* as deposited as PTA-127807; and/or (e) a *Levilactobacillus brevis* as deposited as PTA-127808. In some embodiments, the composition is a starter culture, dough, or food product (e.g., a baked good).

In some embodiments, the composition comprises: (a) a yeast with an ITS nucleic acid sequence sharing at least 97%, at least 98%, at least 99%, or 100% sequence identity to SEQ ID NO: 207 or SEQ ID NO: 267; and/or (b) a bacterium with a 16S nucleic acid sequence sharing at least 97%, at least 98%, at least 99%, or 100% sequence identity to SEQ ID NO: 4 or SEQ ID NO: 270. In some embodiments, the composition is a starter culture, dough, or food product (e.g., a baked good).

In some embodiments, the composition comprises: (a) a *Saccharomyces cerevisiae* as deposited as PTA-127804; and/or (b) a *Fructilactobacillus sanfranciscensis* as deposited as PTA-127806. In some embodiments, the composition is a starter culture, dough, or food product (e.g., a baked good).

In some embodiments, the composition comprising the microorganisms described herein is formulated as a liquid, a powder, a pill, a tablet, or a pellet. In some embodiments, the powder is a temperature-stable powder or a cold-requiring powder. In some embodiments, the composition is a time-controlled released product or a pH-controlled release product.

In some embodiments, the compositions comprising microorganisms of the present disclosure include combinations of microorganisms as spores and/or vegetative cells from bacteria and/or fungi. In some embodiments, the compositions comprise bacteria and/or fungi in the form of spores. In some embodiments, the compositions comprise bacteria and/or fungi in the form of vegetative cells.

In some embodiments, the composition comprises viable cells of the microorganisms described herein. In some embodiments, the composition comprises at least 25%, at least 50%, at least 75%, at least 85%, or at least 95% viable cells from one or more microorganisms described herein.

In some embodiments, the composition comprises a microbe with a viable cell count of at least $10^2$ cells/g, at least $10^3$ cells/g, at least $10^4$ cells/g, at least $10^5$ cells/g, at least $10^6$ cells/g, at least $10^7$ cells/g, at least $10^8$ cells/g, at least $10^9$ cells/g, at least $10^{10}$ cells/g, at least $10^{11}$ cells/g, at least $10^{12}$ cells/g, at least $10^{13}$ cells/g, at least $10^{14}$ cells/g, at least $10^{15}$ cells/g, at least $10^{16}$ cells/g, at least $10^{17}$ cells/g, or at least $10^{18}$ cells/g.

In some embodiments, the composition comprises microorganisms with a total viable cell count of at least $10^2$ cells/g, at least $10^3$ cells/g, at least $10^4$ cells/g, at least $10^5$ cells/g, at least $10^6$ cells/g, at least $10^7$ cells/g, at least $10^8$ cells/g, at least $10^9$ cells/g, or at least $10^{10}$ cells/g, at least $10^{11}$ cells/g, at least $10^{12}$ cells/g, at least $10^{13}$ cells/g, at least $10^{14}$ cells/g, at least $10^{15}$ cells/g, at least $10^{16}$ cells/g, at least $10^{17}$ cells/g, or at least $10^{18}$ cells/g.

In some embodiments, the composition comprises a microbe with a viable cell count of at least $10^2$ CFU/g, at least $10^3$ CFU/g, at least $10^4$ CFU/g, at least $10^5$ CFU/g, at least $10^6$ CFU/g, at least $10^7$ CFU/g, at least $10^8$ CFU/g, at least $10^9$ CFU/g, at least $10^{10}$ CFU/g, at least $10^{11}$ CFU/g, at least $10^{12}$ CFU/g, at least $10^{13}$ CFU/g, at least $10^{14}$ CFU/g, at least $10^{15}$ CFU/g, at least $10^{16}$ CFU/g, at least $10^{17}$ CFU/g, or at least $10^{18}$ CFU/g.

In some embodiments, the composition comprises microorganisms with a total viable cell count of at least $10^2$ CFU/g, at least $10^3$ CFU/g, at least $10^4$ CFU/g, at least $10^5$ CFU/g, at least $10^6$ CFU/g, at least $10^7$ CFU/g, at least $10^8$ CFU/g, at least $10^9$ CFU/g, or at least $10^{10}$ CFU/g, at least $10^{11}$ CFU/g, at least $10^{12}$ CFU/g, at least $10^{13}$ CFU/g, at least $10^{14}$ CFU/g, at least $10^{15}$ CFU/g, at least $10^{16}$ CFU/g, at least $10^{17}$ CFU/g, or at least $10^{18}$ CFU/g.

In some embodiments, the composition comprising one or more microorganisms described herein further comprises one or more additional compounds. In some embodiments, the compound is an enzyme (e.g., amylase or a gluten-degrading enzyme), salt (e.g., sodium chloride, an acetate salt, a fumarate salt, a citrate salt, and/or a carbonate salt), an antioxidant (e.g., ascorbic acid or ascorbate salts), or a growth-promoting ingredient for select microorganisms.

In some embodiments, the composition comprising one or more microorganisms described herein comprises one or more preservatives such as calcium propionate, sorbic acid, sodium benzoate, potassium sorbate, ascorbic acid, azodicarbonamide, or sugar.

In some embodiments, the composition comprising one or more microorganisms described herein comprises one or more leavening agents such as baking powder, baking soda, cream of tartar, air, steam, or baker's yeast.

In some embodiments, the composition comprising one or more microorganisms described herein comprises one or more flavoring agents. Flavoring agents include, but are not limited to, organic acids such as lactic, acetic, or ascorbic acid. Dehydrated grain or dairy products such as malt powder, milk powder, or malted milk powder. Liquid dairy products such as milk or cream.

Sugars including glucose, maltose, sucrose. Fats such as butter, olive oil, canola oil, and peanut oil. Herbs spices, and their extracts such as vanilla, rosemary, thyme, pepper, and garlic. Fermented foods including yogurt, chocolate, fermented grains or fermented vegetables. Whole Fruit, nuts, dehydrated fruits, and/or their extracts such as cherry, raisin, almond, pistachio, or apple.

In some embodiments, the composition comprising one or more microorganisms described herein is encapsulated. In some embodiments, the encapsulating composition is a matrix selected from a sugar matrix, gelatin matrix, polymer matrix, silica matrix, or foam matrix. In some embodiments, the encapsulating composition is a gelatin, chitosan, pectin, carrageenan, maltodextrin, starch, cyclodextrins, polyvinyl alcohol, liposomes, polyhydroxyalkanoates, silica, polyethylene glycol, whey protein, soy protein, casein, alginate, sugars, fats, or wax.

In some embodiments, the composition comprising one or more microorganisms described herein is incorporated into dough as a single dose. In some embodiments, the composition comprising one or more microorganisms described herein is incorporated into dough in multiple doses.

In some embodiments, the composition comprising one or more microorganisms described herein is shelf-stable in a refrigerator (2-4 °C) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the composition comprising one or more microorganisms described herein is shelf-stable in a refrigerator (2-4 °C) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks.

In some embodiments, the composition comprising one or more microorganisms described herein is shelf-stable at room temperature (20-22 °C) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the composition comprising one or more microorganisms described herein is shelf-stable at room temperature (20-22 °C) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks.

In some embodiments, the composition comprising one or more microorganisms described herein is shelf-stable in a freezer (−18 to −20 °C) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days.

In some embodiments, the composition comprising one or more microorganisms described herein is shelf-stable in a freezer (−18 to −20 °C) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks.

In some embodiments, the composition comprising one or more microorganisms described herein is shelf-stable at a relative humidity of at least 15%, at least 20%, at least 25%, at least 30%, at least 35%, at least 40%, at least 45%, at least 50%, at least 55%, at least 60%, at least 65%, at least 70%, at least 75%, or at least 80%.

Methods and Uses

In some embodiments, the present disclosure relates to a method of producing a dough, the method comprising admixing one or more of the microorganisms described herein to the dough and incubating the admixture for a period of time. In some embodiments, the method comprises a further step of baking the dough. The present disclosure also relates to a food product (e.g., a baked good) produced by the methods described herein.

In some embodiments, the present disclosure provides a method of producing fermented dough or baked goods with improved organoleptic or human health impacts comprising administering a composition comprising one or more microorganisms described herein to a dough in an amount effective to produce the desired effects in the dough administered compared to a dough that was not administered the composition or administered a non-defined microbial community or administered baker's yeast alone.

In some embodiments, the disclosure provides methods of improving the rheological properties of dough and/or the baked good by using one or more of the microorganisms described herein. Rheological properties include, but are not limited to, reduced time of fermentation, bread texture, bread shape, bread or dough volume, sweet taste, sour taste, aroma, bread crust and bread crumb color, bread moisture retention, and bread crumb structure.

In some embodiments, the method comprises incubating the admixture comprising the one or more microorganisms for a period of time. In some embodiments, the admixture is incubated for at least at least 5 minutes, at least 10 minutes, at least 15 minutes, at least 30 minutes, at least 45 minutes, at least 1 hour, at least 2 hours, at least 3 hours, at least 4 hours, at least 5 hours, at least 6 hours, at least 12 hours, at least 24 hours, at least 36 hours, at least 48 hours, at least 60 hours, at least 72 hours, at least 84 hours, at least 96 hours, at least 108 hours, or at least 120 hours.

In some embodiments, the method comprises incubating the admixture comprising the one or more microorganisms at different temperatures. In some embodiments, the admixture is incubated at least −5 degrees Celsius, at least 0 degrees Celsius, at least 5 degrees Celsius, at least 10 degrees Celsius, at least 15 degrees Celsius, at least 20 degrees Celsius, at least 25 degrees Celsius, at least 30 degrees Celsius, at least 40 degrees Celsius, at least 50 degrees Celsius, at least 60 degrees Celsius, at least 70 degrees Celsius, at least 80 degrees Celsius, at least 90 degrees Celsius, or at least 100 degrees Celsius.

In some embodiments, the composition comprising one or more microorganisms described herein reduces time of fermentation. In some embodiments, the one or more microorganisms reduce time of fermentation by at least 5 minutes, at least 10 minutes, at least 15 minutes, at least 30 minutes, at least 45 minutes, at least 1 hour, at least 2 hours, at least 3 hours, at least 4 hours, at least 5 hours, at least 6 hours, at least 12 hours, at least 24 hours, at least 36 hours, at least 48 hours, at least 60 hours, at least 72 hours, at least 84 hours, at least 96 hours, at least 108 hours, or at least 120 hours.

In some embodiments, the composition comprising one or more microorganisms described herein improves the texture of the dough and/or baked good. The term "texture" includes, but is not limited to, hardness, adhesiveness, resilience, cohesiveness, chewiness, springiness, and gumminess of the dough and/or baked good.

In some embodiments, the composition comprising one or more microorganisms described herein increases leavening of dough. In some embodiments, the increased leavening of dough during fermentation results in a baked good that has the desired volume, texture, and/or crumb.

In some embodiments, the composition comprising one or more microorganisms described herein increases rise rate of dough. In some embodiments, the increased rise rate of dough during fermentation results in a baked good that has the desired volume, texture, and/or crumb.

In some embodiments, the composition comprising one or more microorganisms described herein increases elasticity of the dough and/or baked good. In some embodiments, the composition comprising one or more microorganisms described herein decreases elasticity of the dough and/or baked good.

In some embodiments, the composition comprising one or more microorganisms described herein increases firmness of the dough and/or baked good. In some embodiments, the composition comprising one or more microorganisms described herein decreases firmness of the dough and/or baked good.

In some embodiments, the composition comprising one or more microorganisms described herein affects proteins in the dough and/or baked good. Proteins in the dough or baked good include, but are not limited to, gliadins, glutenin, secalins, albumin, globulins, and prolamins. In some embodiments, the composition comprising one or more microorganisms described herein increases protein degradation in the dough and/or baked good. In some embodiments, the composition comprising one or more microorganisms described herein decreases protein degradation in the dough and/or baked good.

In some embodiments, the composition comprising one or more microorganisms described herein produces peptides in the dough and/or baked good. Some peptide classes produced include, but are not limited to, antioxidant peptides, antihypertensive peptides, and anti-tumoral peptides.

In some embodiments, the composition comprising one or more microorganisms described herein degrades chemical compounds and/or chemical precursors in the dough and/or baked good. Chemical compounds include, but are not limited to, phytic acid, tannins, biogenic amines, acrylamide, furosine and 5-hydroxymethylfurfural.

In some embodiments, the composition comprising one or more microorganisms described herein generates compounds that enhance flavor and/or aroma of the dough and/or baked good. Flavor and aroma compounds include, but are not limited to, phenolics, esters, aldehydes, ketones, alcohols, and lipids.

In some embodiments, the composition comprising one or more microorganisms described herein generates compounds that enhance nutritional quality of the dough and/or baked good. Compounds that enhance the nutritional value of bread and dough include, but are not limited to, polyphenols, vitamins, and minerals.

In some embodiments, the composition comprising one or more microorganisms described herein degrades simple and/or complex carbohydrates in the dough and/or baked good. In some embodiments, the composition comprising one or more microorganisms described herein utilizes simple and/or complex carbohydrates in the dough and/or baked good. Carbohydrates include, but are not limited to, fructans, dextrins, maltose, glucose, fructose, melibiose, starch, sorbitol, mannitol, and raffinose.

In some embodiments, the composition comprising one or more microorganisms described herein modulates the pH of dough over the length of fermentation (i.e., from addition of the microbial composition to the baked product). In some embodiments, the composition comprising one or more microorganisms described herein maintains the pH of dough over the length of fermentation. In some embodiments, the composition comprising one or more microorganisms described herein maintains the pH of dough at the mixing stage, autolyse stage, bulk stage, portion stage, and/or baked/final stage of fermentation.

In some embodiments, the composition comprising one or more microorganisms described herein lowers the pH of dough over the length of fermentation (i.e., from addition of the microbial composition to the baked product). In some embodiments, the composition comprising one or more microorganisms described herein lowers the pH of dough at the mixing stage, autolyse stage, bulk stage, portion stage, and/or baked/final stage of fermentation. In some embodiments, the composition comprising one or more microorganisms described herein lowers the pH of the baked good. In some embodiments, the composition comprising one or more microorganisms described herein lowers the pH of dough by about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0.

In some embodiments, the composition comprising one or more microorganisms described herein increases the pH of dough over the length of fermentation (i.e., from addition of the microbial composition to the baked product). In some embodiments, the composition comprising one or more microorganisms described herein increases the pH of dough at the mixing stage, autolyse stage, bulk stage, portion stage, and/or baked/final stage of fermentation. In some embodiments, the composition comprising one or more microorganisms described herein increases the pH of the baked good. In some embodiments, the composition comprising one or more microorganisms described herein increases the pH of dough by about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0.

In some embodiments, use of the composition comprising one or more microorganisms described herein results in a dough and/or food product with a pH of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0 of the dough or the baked good. In some embodiments, use of the composition comprising one or more microorganisms described herein results in a dough and/or food product with a pH between about 4 and about 5. In some embodiments, use of the composition comprising one or more microorganisms described herein results in a dough and/or food product with a pH between about 4.0 and about 4.5. In some embodiments, use of the composition comprising one or more microorganisms described herein results in a dough and/or food product with a pH between about 4.5 and about 5.0. In some embodiments, use of the composition comprising one or more microorganisms described herein results in a dough and/or food product with a pH between about 4.25 and about 4.5. In some embodiments, use of the composition comprising one or more microorganisms described herein results in a dough and/or food product with a pH between about 4.5 and about 4.75. In some embodiments, use of the composition comprising one or more microorganisms described herein results in a dough and/or food product with a pH between about 4.75 and about 5.0.

In some embodiments, the composition comprising one or more microorganisms described herein generates organic acids during fermentation. These acids include but are not limited to lactic, acetic, propionic, butyric, isobutyric, valeric, and isovaleric acids. The single organism, set, or ensemble of organisms' ability to produce organic acids both in dough and other mediums can be assessed using measurements of total titratable acidity (TTA) or more specifically using analytical chemistry techniques such as high-performance liquid chromatography (HPLC).

In some embodiments, the composition comprising one or more microorganisms described herein degrades dough substrates during the fermentation process that impact human health. Substrates degraded by microorganisms include allergens such as gluten, high glycemic carbohydrates, and those which impact the digestibility of breads. Gluten is a widely dispersed protein found in grains such as wheat, barley, and rye. While gluten is essential to maintain the structure of bread, it is also an allergen for a portion of the population. The microorganisms in the present disclosure act to degrade dough proteins including gluten through enzymatic digestion, specifically those glutens that cause allergic reactions (i.e., the immunogenic gluten epitopes). The glycemic index attempts to quantitatively measure how quickly and significantly the carbohydrates in food consumed will affect blood sugar. Catabolism of carbohydrates, such as glucose, by the microorganisms described herein act to lower the glycemic index of breads through the fermentation of blood glucose elevating sugars before they are ingested. Digestibility enhancement is a process in which foods are transformed to make them easier to be broken down and for the nutrients contained within to be absorbed. In some embodiments, the compositions comprising one or more microorganisms described herein increase digestibility of breads. In some embodiments, digestibility of breads is enhanced through degradation of proteins, carbohydrates, organic acids, and the liberation of nutrients essential for effective digestion.

In some embodiments, the composition comprising one or more microorganisms described herein has a lower glycemic index compared to the same composition produced without the microorganisms of the present disclosure.

In some embodiments, consumption of a composition comprising one or more microorganisms described herein results in a lower blood glucose level in a subject compared to the same composition produced without the microorganisms of the present disclosure.

In some embodiments, the composition comprising one or more microorganisms described herein increase the shelf-life of the dough or baked good. In some embodiments, the composition comprising one or more microorganisms described herein increases shelf-life by at least one day, at least two days, at least three days, at least four days, at least five days, at least six days, at least seven days, at least eight days, at least nine days, at least ten days, at least two weeks, at least three weeks, at least four weeks, at least five weeks, at least six weeks, at least seven weeks, or at least 8 weeks compared to the same dough or baked good produced without the microorganisms of the present disclosure.

In some embodiments, the composition comprising one or more microorganisms described herein competitively excludes microbial pathogens, such as molds or other microorganisms that lead to food spoilage.

In some embodiments, the composition comprising one or more microorganisms described herein modulates the metabolism or activity of other microorganisms in the dough, baked good, or other medium.

EXAMPLES

The following is a description of various methods and materials used in the studies. They are put forth so as to provide those of ordinary skill in the art with a complete disclosure and description of how to make and use the present invention, and are not intended to limit the scope of what the inventors regard as their invention, nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present invention. Efforts have been made to ensure accuracy with respect to numbers used (e.g., amounts, percentages, etc.), but some experimental errors and deviations should be accounted for.

Example 1: In Silico Isolation of Microorganisms

Sample Collection

Samples of sourdough starters were obtained through collection from outside sources or produced in-house through spontaneous fermentation. Sourdough starters were produced by "backslopping", which involves mixing whole wheat flour, rye, all-purpose flour, or some mixture of the flours with water at room temperature (e.g., 70-75° F. or 21-24 °C) for 24 hours or at colder temperatures (e.g., 40-69° F. or 4.5-20.6 °C). Then, on the second day, and proceeding days, the mixture was refreshed with part of the previous day's fermented mixture with additional flour and water. Starters obtained from an outside source were similarly refreshed daily, weekly, monthly, or bi-monthly. For each starter, one or more samples were obtained across passages from an epoch or across a fermentation cycle (e.g., across 24 hours or up to two weeks).

The environmental conditions and metadata were collected for each sample. Sample metadata included sample history, pH, temperature, flour type, leavening time, age, time of collection, the total number of bacterial or fungal cells (e.g., CFUs), organoleptic properties, immunogenic gluten content, and glycemic index.

FIG. 1A shows the blood glucose level across time from consuming bread produced with baker's yeast plus additives or a two strain inoculant comprising *Fructilactobacillus sanfranciscensis* (PTA-127806) and *Saccharomyces cerevisiae* (PTA-127804). Bread produced using the two strain inoculant exhibited lower blood glucose levels compared to bread produced using baker's yeast plus additives.

Figure 1B:
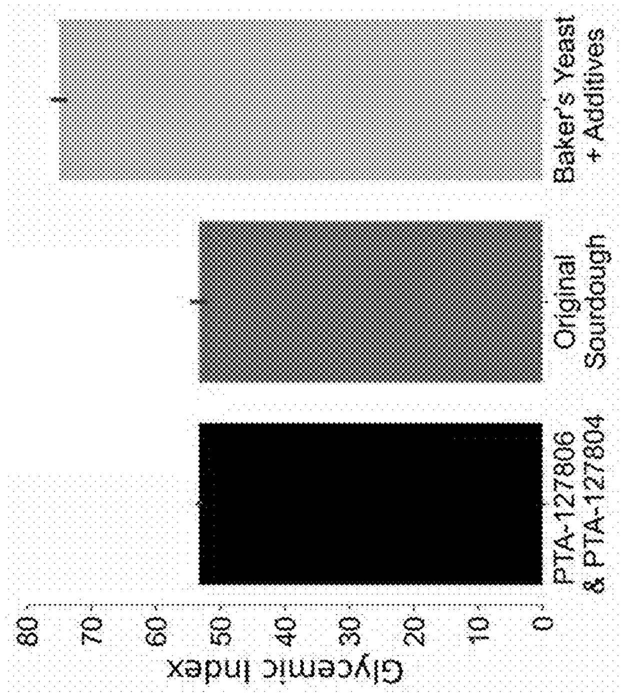
FIG. 1B shows the glycemic index from consuming bread produced using a two strain inoculant comprising *Fructilactobacillus sanfranciscensis* (PTA-127806) and *Saccharomyces cerevisiae* (PTA-127804), original sourdough, or baker's yeast plus additives.

FIG. 1B shows the glycemic index from consuming bread produced using a two strain inoculant comprising *Fructilactobacillus sanfranciscensis* (PTA-127806) and *Saccharomyces cerevisiae* (PTA-127804), original sourdough, or baker's yeast plus additives. Bread produced using the two strain inoculant exhibited a lower glycemic index compared to bread produced using baker's yeast plus additives.

Figure 2:
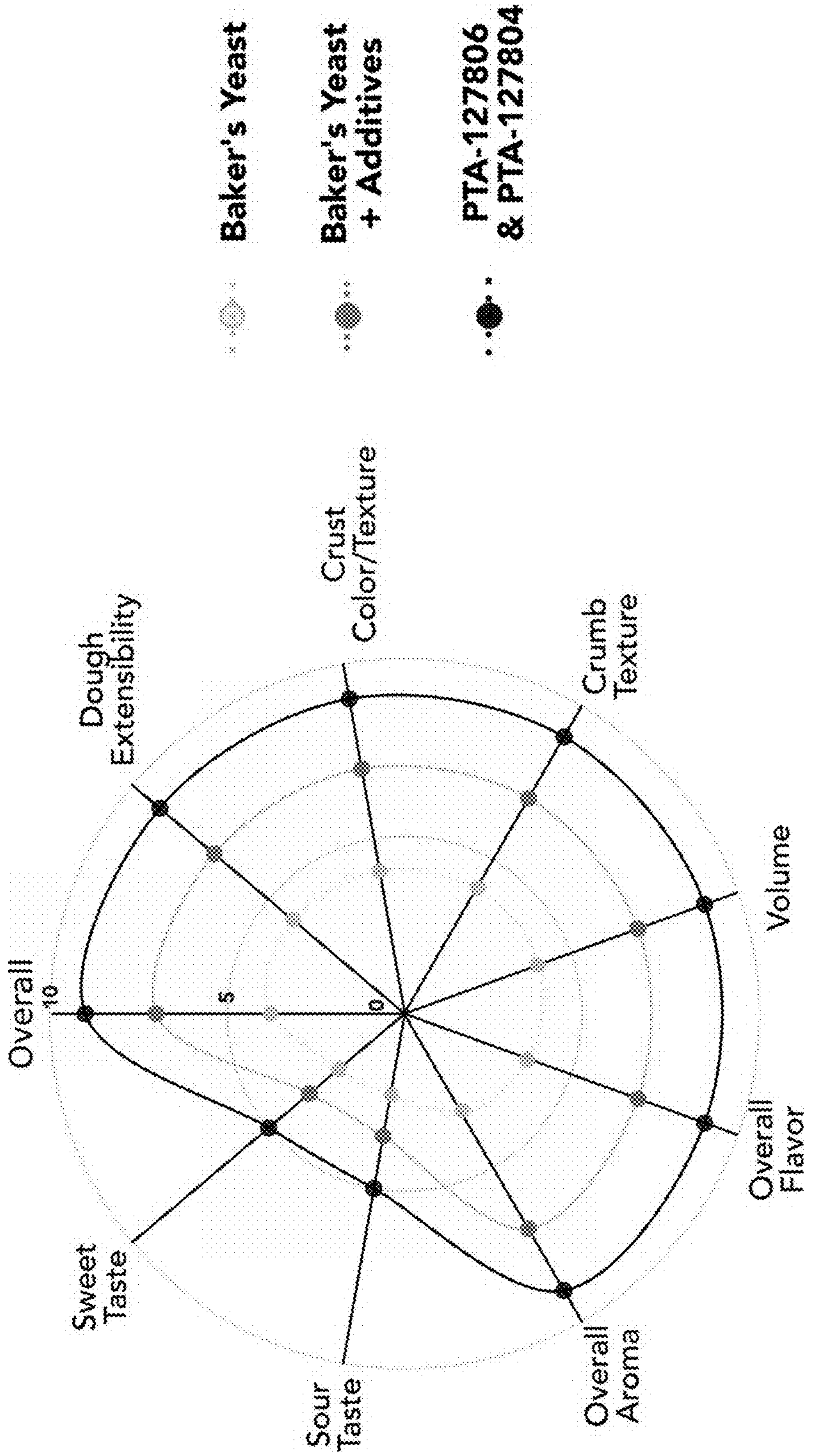
FIG. 2 depicts the organoleptic properties of bread made with baker's yeast, baker's yeast plus additives, or a two strain inoculant comprising *Fructilactobacillus sanfranciscensis* (PTA-127806) and *Saccharomyces cerevisiae* (PTA-127804). Each organoleptic property was scored on a scale of 0 to 10. The node in the graph represents the average score across five judges.

FIG. 2 depicts the organoleptic properties of bread made with a two strain inoculant comprising *Fructilactobacillus sanfranciscensis* (PTA-127806) and *Saccharomyces cerevisiae* (PTA-127804), baker's yeast plus additives, or baker's yeast. The results show that the two strain inoculant provided a better overall organoleptic experience compared to baker's yeast or baker's yeast plus additives.

Sample Processing and Data Production

DNA was extracted from a sample, a set of two samples, or more than two samples containing multiple organisms. Extracted DNA was subjected to PCR to enrich the copy number of a selected conserved target gene (i.e., 16S rRNA or internal transcribed spacer (ITS) sequencing). Amplified DNA of the enriched genes was sequenced using selected sequencing technology. Resulting sequences were trimmed, quality filtered, and clustered into operational taxonomic units (OTUs). Taxonomy was assigned to OTUs by sequence alignment to a reference database for the target gene of interest. Extracted DNA was subjected to fragmentation with subsequent short-read sequencing (e.g., 20-300 base pairs per sequence) and direct sequencing of long-reads (e.g., 300 to greater than 1 million base pairs per sequence) using selected sequencing technology (i.e. shotgun metagenomics). The resulting sequences were trimmed, quality filtered, and directly aligned to known sequence databases or reconstructed into genomes (e.g., metagenome-assembled genomes (MAG)). The taxonomic abundance and functional capacity abundance of each MAG and sample were quantified through a reference database. RNA was extracted from a sample, a set of two samples, or more than two samples containing multiple organisms of the same or similar samples to those from which DNA was extracted (i.e., metatranscriptomics). The RNA was enriched for mRNA and sequenced using selected sequencing technology. The resulting RNA sequences were then trimmed, quality filtered, in silico enriched for mRNA, and then directly aligned to functional gene databases or aligned to MAGs constructed from the DNA extracted samples. The transcriptional regulation and abundance were then quantified from the alignments for each sample and MAG. Only the RNA contained within the ribosome at the time of sampling was extracted from a sample, a set of two samples, or more than two samples containing multiple organisms of the same or similar samples to those from which DNA was extracted (i.e., ribosome profiling). The RNA was enriched for mRNA and sequenced using selected sequencing technology. The resulting RNA sequences were then trimmed, quality filtered, in silico enriched for mRNA, and then directly aligned to functional gene databases or aligned to MAGs constructed from the DNA extracted samples. The translational regulation and abundance were then quantified from the alignments for each sample and MAG.

Metabolites were quantified in a sample, a set of two samples, or more than two samples that are the same or similar samples to those from which DNA was extracted. Metabolites were measured using either Liquid Chromatography-Mass Spectrometry (LC-MS/MS), Nuclear Magnetic Resonance (NMR) Spectroscopy, chromatograph/mass spectrometer (GC/MS), Mass Spectrometry (MS), or High-Performance Liquid Chromatography (HPLC). For LC-MS/MS, metabolites were first extracted using liquid-liquid extraction or solid-phase extraction, then Liquid Chromatography (LC) was used to separate the metabolites within the sample based on their chemical properties followed by MS or Triple Quadrupole MS to detect and quantify metabolites based on their mass-to-charge ratio (m/z). Next, the raw data was processed for peak picking, deconvolution, retention time alignment, spectral matching or molecular networking to known metabolites, and quantification by peak areas or intensities. For GC/MS, volatile organic compounds (VOCs) were captured from each sample and then introduced into the GC/MS system through direct injection, headspace sampling, or thermal desorption. The carrier in the GC was either helium or nitrogen, which leads to the separation of compounds based on volatility. After separation, the MS detected and quantified metabolites based on their mass-to-charge ratio (m/z). Data was processed in a similar way to LC-MS/MS.

In Silico Identification of Microbe Combinations

Across samples and for each sample across time, each data type (e.g., metabolite, VOCs, 16S, ITS, metagenomics, metatranscriptomics, metadata, and ribosome profiling). Each sample was compared or correlated across metadata by the taxonomic or functional diversity within (alpha-diversity) each sample or across time using the Shannon index (Tucker et al. 2017). Each sample was compared or correlated across metadata by the taxonomic or functional differences in composition (beta-diversity) across samples or across time by all samples using UniFrac (Lozupone and Knight 2005), Compositional Tensor Factorization (Martino et al. 2021), and/or Robust Aitchison PCA (Martino et al. 2019) performed across datatypes or within each datatype individually to form low-dimensional sample clusters (i.e. dimensionality reduction). Network analysis was performed using the dimensionality reduction clusters and from network correlation analyses including all datatypes and metadata with Pearson correlations, Spearman correlations, canonical correspondence analysis (CCA), and partial least squares (PLS) (Meng et al. 2016; Rohart et al. 2017). The differential abundance of specific taxa or functional compositions across samples, within samples across time, or across samples and time was performed through ALDEx2 (Gloor et al. 2019), Linear Mixed Effects models (Rahman et al. 2023), and ANCOM-BC (Lin and Peddada 2020).

Figure 3A:
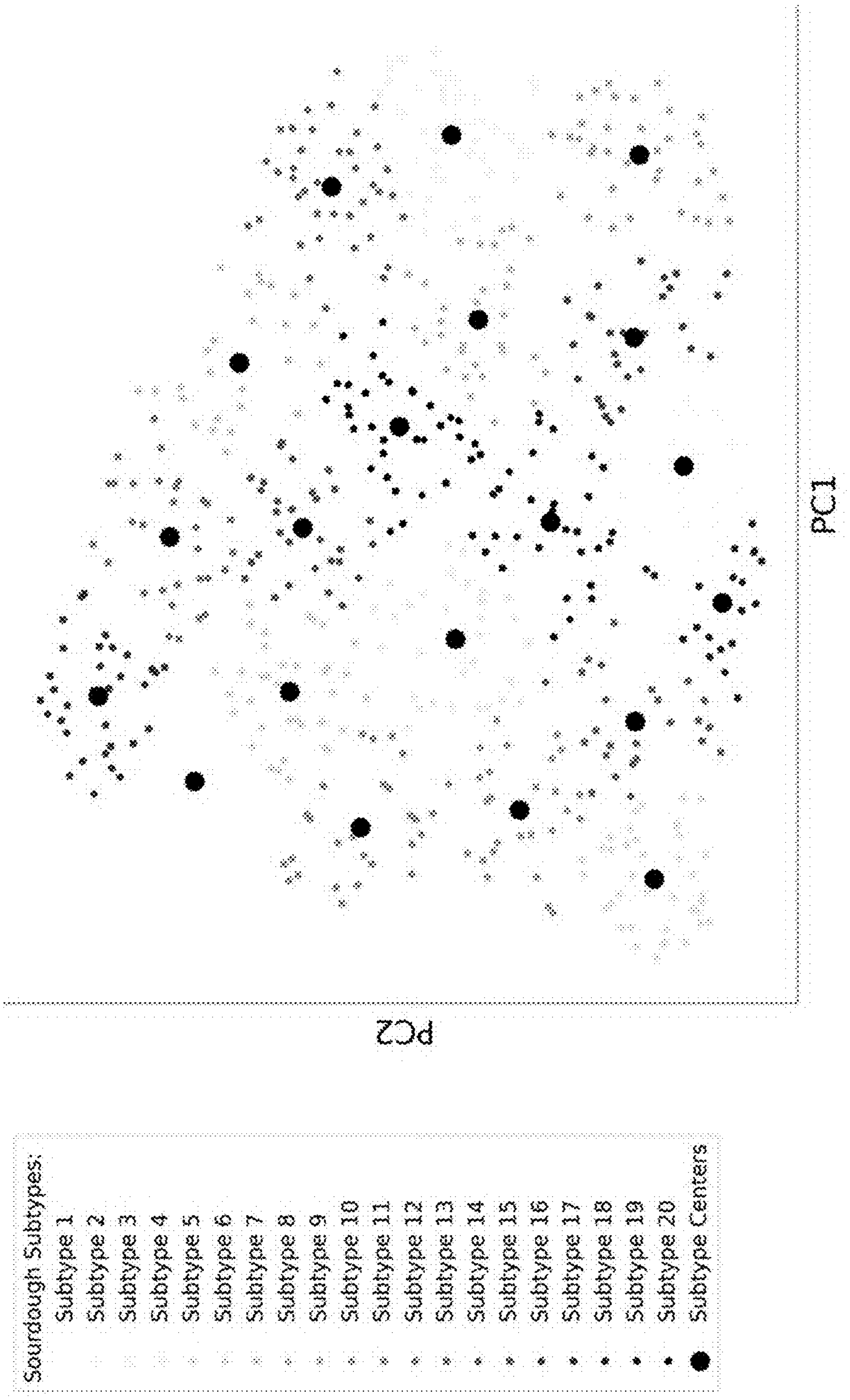
FIG. 3A shows a Robust Aitchison principal component analysis (RPCA) plot where each dot represents a different sourdough microbial community and the distance between the dots represents their similarity colored by the sourdough sub-types with cluster centers of representative sourdoughs shown as larger dots. Each representative sourdough was sampled across time and different fermentation conditions to determine the key strains in sourdough.
Figure 3B:
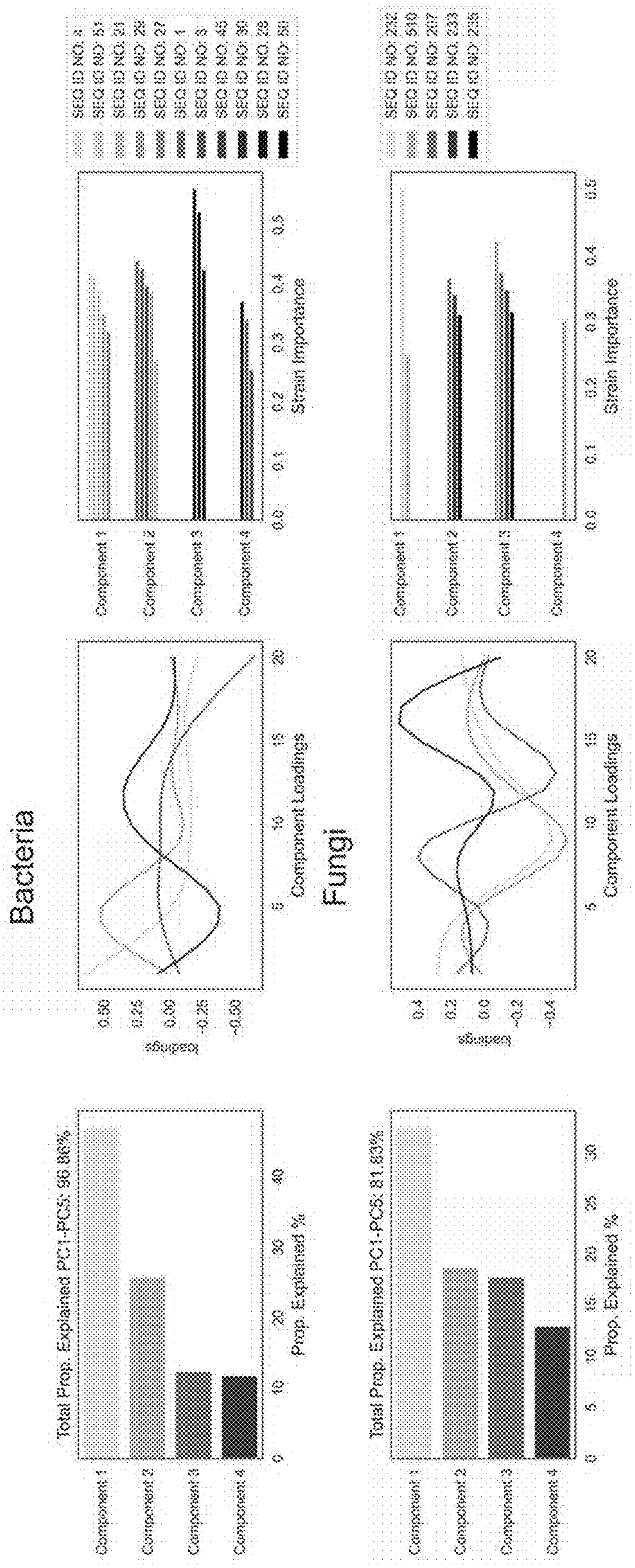
FIG. 3B shows compositional tensor factorization across time for the first four principal components (PCs), which reconstructed 96.9% and 81.8% of the total variation across time for bacteria and fungi, respectively (left panel). The trajectories across time (middle panel) of the important strains in the community across time linked to each PC (right panel) were determined.

FIG. 3A shows a Robust Aitchison principal component analysis (RPCA) plot where each dot represents a different sourdough microbial community and the distance between the dots represents their similarity colored by the sourdough sub-types with cluster centers of representative sourdoughs represented as larger dots. Each representative sourdough was sampled across time and different fermentation conditions to determine the key strains in sourdough. FIG. 3B shows compositional tensor factorization across time for the first four principal components (PCs) which reconstruct 96.9% and 81.8% of the total variation across time for bacteria and fungi, respectively (left panel). The trajectories across time (middle panel) of the important strains in the community across time linked to each PC (right panel) were determined. Within each representative sourdoughs identified in RPCA (FIG. 3A), when sampled across time, key strains of both bacteria and fungi were identified that contribute to the fermentations across time.

Figure 4C:
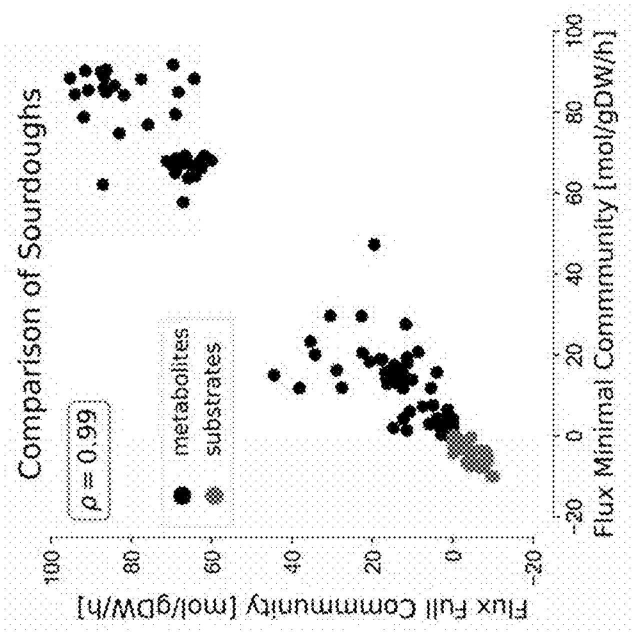
FIG. 4C shows the similarity of substrate utilization or metabolite production in final sourdough between the full (five strain) and minimal (two strain) communities.
Figure 4B:
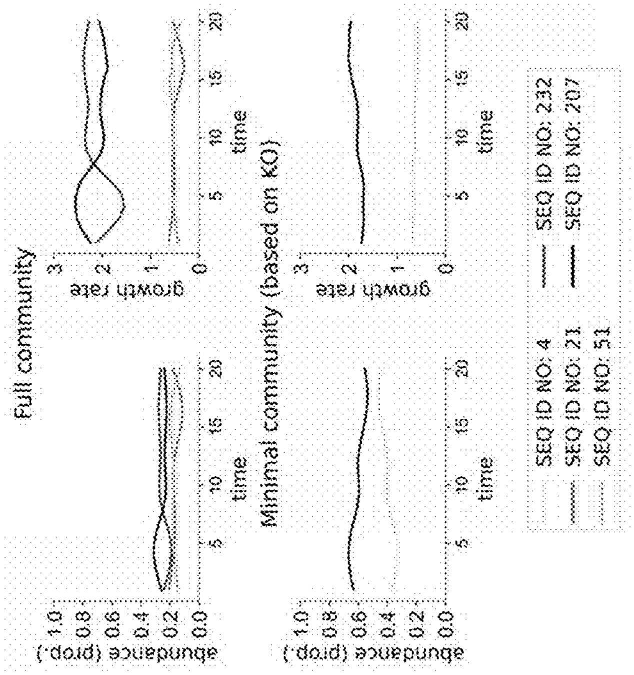
FIG. 4B shows the impact of abundances (left panel) and growth rates (right panel) across fermentation time in the sourdough for the full (five strain) and minimal (two strain) communities.
Figure 4A:
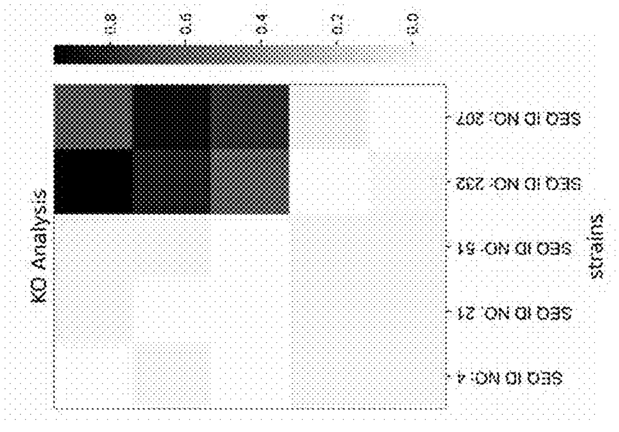
FIG. 4A shows metabolic modeling knock out analysis of the impact on growth rate of all other strains by removing one strain from the microbial community to determine the key microbial community members.

FIG. 4A shows metabolic modeling knock out analysis of the impact on growth rate of all other strains by removing one strain from the microbial community to determine the key microbial community members. FIG. 4B shows the impact of abundances (left panel) and growth rates (right panel) across fermentation time in the sourdough for the full (five strain) and minimal (two strain) communities. FIG. 4C shows the similarity of substrate utilization or metabolite production in the final sourdough between the full (five strain) and minimal (two strain) communities. These results show that the minimal two strain community was predicted in silico to have a 99% similarity to the full five strain community in the substrates catabolized and metabolites produced in the final sourdough fermentation. Thus, based on but not limited to the alpha-diversity, beta-diversity, clustering analysis, network analysis, and differential abundance analysis information, the minimal and optimal microorganisms that form a community can be predicted in silico to produce a desired sourdough.

Example 2: Microbial Identification for Exclusion of Undesirable Organisms

This example aims to identify the impact of select microbial compositions to competitively exclude microbial pathogens, molds, or other organisms that lead to food spoilage.

Method for Identifying Antimycotic Capability of Supernatant Using Disk Diffusion Susceptibility of mold to experimental organisms was conducted using the disk diffusion method (aka Kirby-Bauer method). Experimental organisms were grown to maximum optical density. Experimental cultures were centrifuged at 4,000 g for 10 minutes and the supernatant was harvested and applied to 6 mm sterile filter paper disks. Select molds were densely plated to form a lawn on solid media. The supernatant-saturated disks were applied to the plates with the selected molds and allowed to incubate for 24 hours at 32 °C Plates were removed from the incubator and clearing of the mold around each disk was observed and measured to determine the antimycotic capability of each experimental sample.

Figure 5:
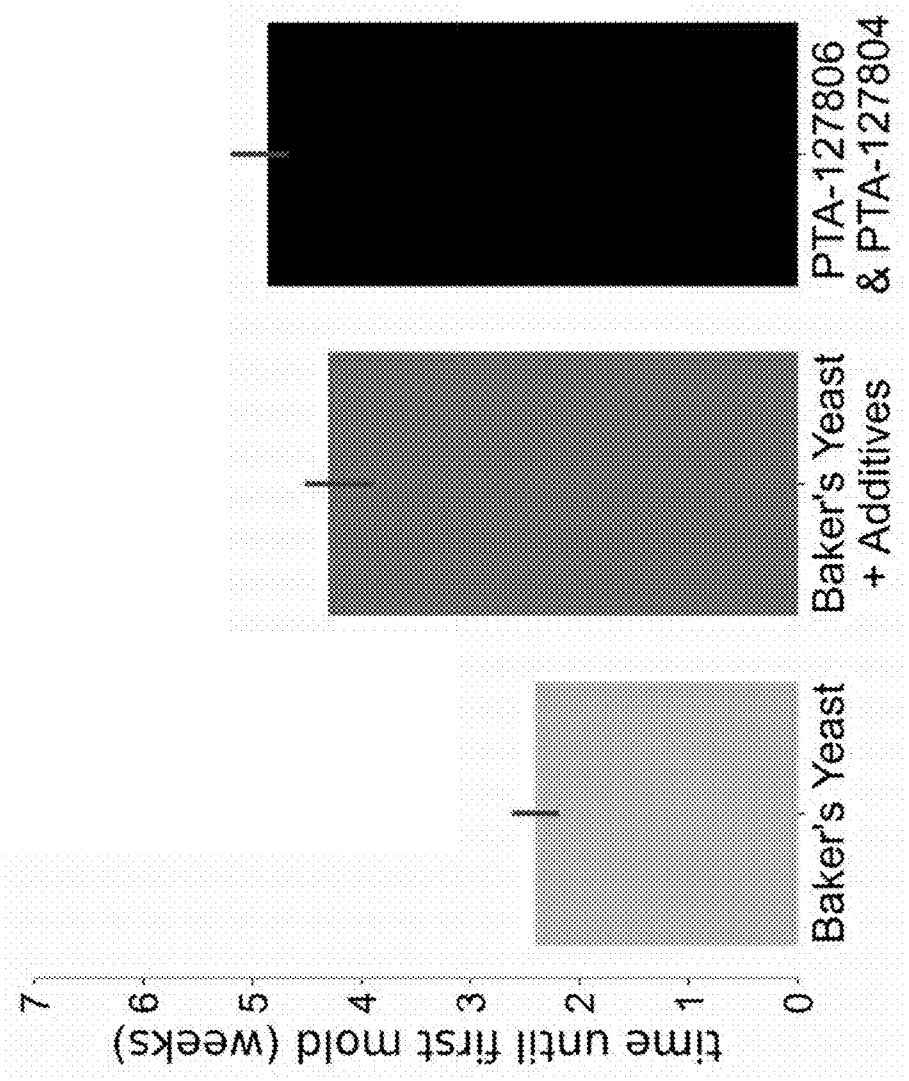
FIG. 5 shows the time until mold formed on baked bread produced using baker's yeast, baker's yeast plus additives, or a two strain inoculant comprising *Fructilactobacillus sanfranciscensis* (PTA-127806) and *Saccharomyces cerevisiae* (PTA-127804).

FIG. 5 shows the time until mold formed on baked bread produced using baker's yeast, baker's yeast plus additives, or a two strain inoculant comprising *Fructilactobacillus sanfranciscensis* (PTA-127806) and *Saccharomyces cerevisiae* (PTA-127804). These results show that the two strain inoculant prevented molding of baked goods.

Example 3: Microbial Identification for Modulation of Organisms in a Consortia This example aims to identify the impact of select microbial compositions to modulate the metabolism or activity of other organisms in a dough or other medium.

Method to Assess Microbial Growth as Part of a Consortia in Dough

Each organism to be tested was cultured in isolation in growth media and incubated at 32 °C for 24 hours. Cells were harvested by centrifugation and 0.1 g of centrifuged cell concentrate was retained for colony-forming unit (CFU) plating. To conduct CFU plating, 0.1 g of the retained cell concentrate was diluted in 1 mL of sterile water and then was serially diluted. Each serial dilution was spread onto solid media optimal for the growth of the specific organism. Each plate for CFU analysis was incubated for 24 hours at 32 °C and colonies were counted for the dilution factor that results in 30-100 total colonies on the respective plate. Cell counts for each culture were calculated using colony count and back calculated using the dilution factor to get the total CFU/g for each organism tested. Wheat flour dough was prepared by mixing 1000 g all-purpose flour (King Arthur Baking Company, USA) 700 g distilled water, and 30 g salt, using a FAMAG IM-8 mixer (Fabbrica Macchine Alimentari Grillo, Italy) for each set or ensemble of organisms to be tested. Co-culture experiments were conducted using methods outlined by Carbonetto et al. (Carbonetto et al. 2020). Each set or ensemble of organisms was mixed into their respective dough at $10^7$ cells per organism per gram of dough. Control doughs were prepared by adding $10^7$ total cells per dough using each organism to be tested in isolation. Doughs were incubated at a selected temperature of interest for 24 hours. At the conclusion of 24 hours, organisms in the dough were CFU counted by resuspending 2 g of dough in 40 mL of tryptone/NaCl solution (1 g of tryptone and 8.5 g of NaCl in 1000 mL of distilled water). The dough/tryptone/NaCl mix was serial diluted and each dilution was spread on solid media optimal for the growth of each organism in the set or consortia. Cell counts were conducted on the dilution, which resulted in 30-100 total colonies on the respective plate. Cell counts for each culture were calculated using colony count and back calculated using the dilution factor to get the total CFU/g for each organism tested. The CFU counts were compared between co-culture and controls to make inferences about the interaction between the organisms.

Figure 6:
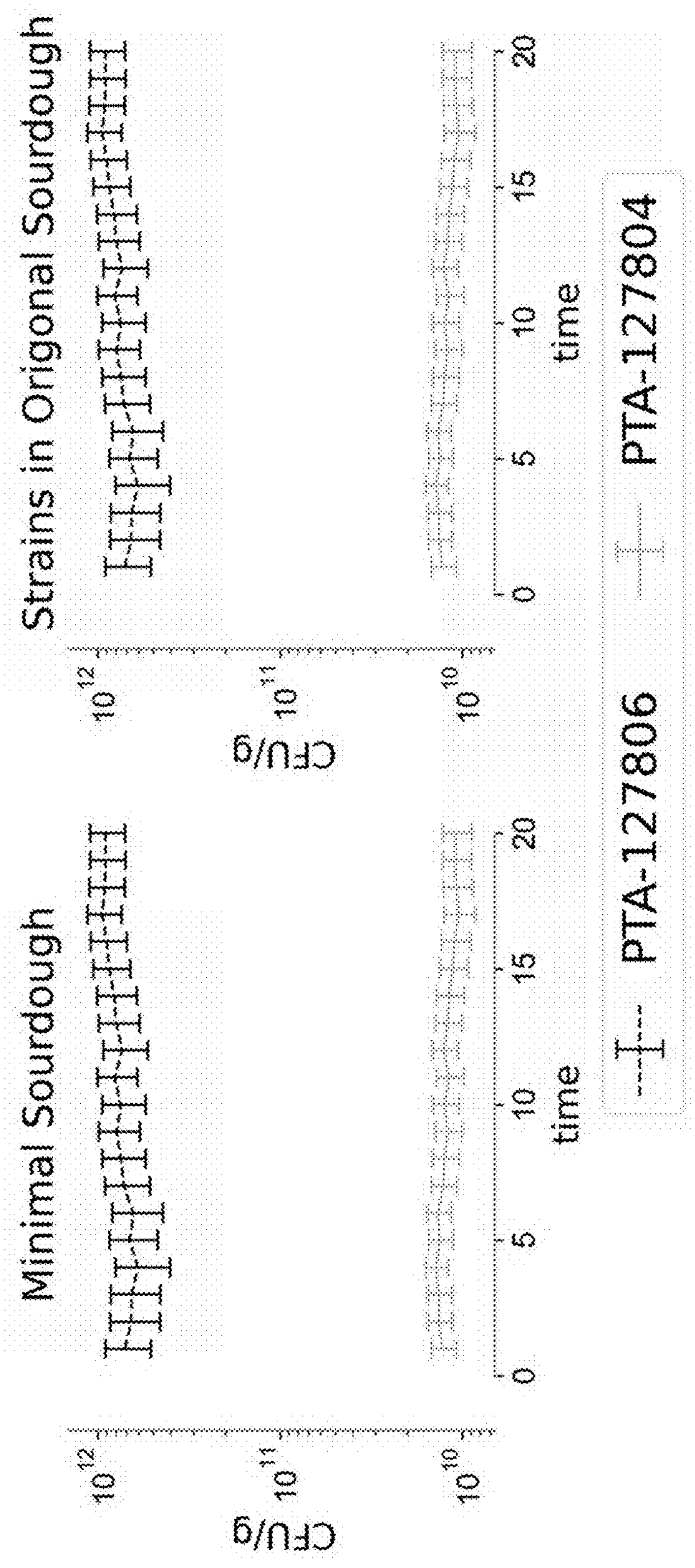
FIG. 6 shows the CFU/g between a two strain inoculant comprising *Fructilactobacillus sanfranciscensis* (PTA-127806) and *Saccharomyces cerevisiae* (PTA-127804) (left panel) and the original sourdough from which they were isolated (right panel) across dough fermentation time (hours).

FIG. 6 shows the CFU/g between a two strain inoculant comprising *Fructilactobacillus sanfranciscensis* (PTA-127806) and *Saccharomyces cerevisiae* (PTA-127804) (left panel) and the original sourdough from which they were isolated (right panel) across dough fermentation time (hours). The two strain inoculant replicated abundances across time in the original sourdough.

Example 4: Isolation, Propagation and Formulation of Microorganisms

This example aims to isolate microorganisms from a consortium and propagate and formulate the microorganisms into a stable product using standard microbiology techniques.

Method for Isolation and Storage of Microorganisms

Microorganisms were isolated from a sample containing a collection of different microorganisms (i.e., a microbial consortium). First, when the sample contained a high level of biomass, a dilution was made by pipetting 100 μL of sample into 900 μL of sterile several times serially. Next, the diluted sample was streaked onto a solid medium to promote the growth of the microbe of interest, including MRS (De MAN, Rogosa, and Sharpe 1960), YPD, or TSB (Doyle, Mehrhof, and Ernst 1968) then incubated in both aerobic and anaerobic conditions between 20-50 °C After incubation, single colonies, which represent a single strain of microorganism, were chosen by color, shape, and size and transferred to a liquid medium of the same type using aseptic techniques. To ensure the purity of the strain, this process was repeated on the colony grown in the liquid medium. Once purified, the single strain is then transferred to a medium suited for long-term storage, such as a solution containing glycerol, and frozen between −40 °C to −80 °C (Gherna and Reddy 2014).

The microorganisms were propagated through use of growth medium. Medium for growing bacteria or fungi includes carbon, nitrogen, salts, minerals, vitamins, pH buffer, and other energy sources or selective agents such as those provided in (Ronald M. Atlas 2004). Suitable mediums for bacteria include but are not limited to MRS (De MAN, Rogosa, and Sharpe 1960) or TSB (Doyle, Mehrhof, and Ernst 1968) and suitable mediums for fungi include but are not limited to YPD ("YPD Media" 2010) or PDB (Eddleman n.d.).

The microorganisms were preserved using common techniques of microbiology. These techniques include but are not limited to freeze-drying, desiccation, freeze-drying with cryoprotectants, spray drying, matrix encapsulation, vacuum drying, and protective packaging.

Figure 7:
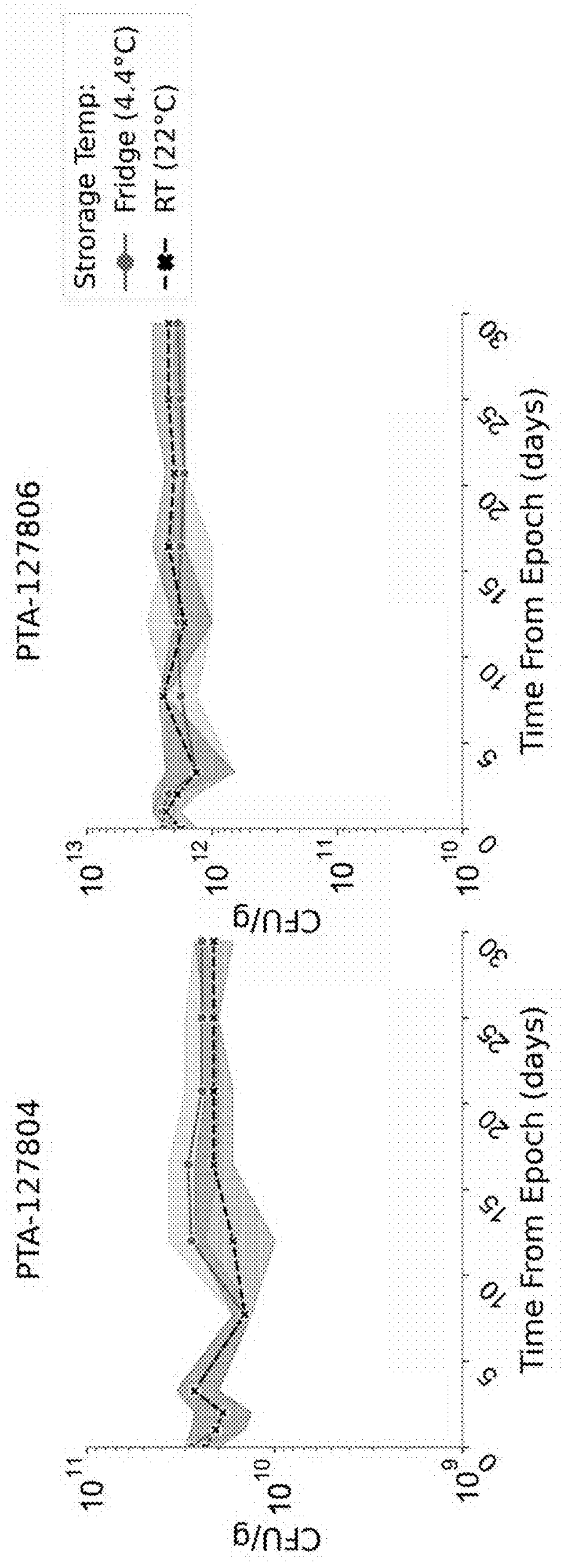
FIG. 7 shows fridge (4.4 °C, light gray line) and room temperature (22 °C, dark gray line) shelf-stability measured by CFU/g of freeze-dried powder across freeze-drying time for *Saccharomyces cerevisiae* (PTA-127804) and *Fructilactobacillus sanfranciscensis* (PTA-127806) isolated and propagated from a sourdough.

FIG. 7 shows fridge (4.4 °C, light gray line) and room temperature (22 °C, dark gray line) shelf-stability measured by CFU/g of freeze-dried powder (y-axis) across freeze-drying time (x-axis) for *Saccharomyces cerevisiae* (PTA-127804) and *Fructilactobacillus sanfranciscensis* (PTA-127806) isolated and propagated from a sourdough. These results show that the two strain inoculant had at least 30 days of stable viability.

Example 5: Identification of Microbes

This example aims to identify microorganisms from a consortium using molecular or microbiological techniques including but not limited to DNA sequencing, qPCR, carbohydrate metabolism, or microscopy.

Method for Identification of Microorganisms by Conserved Target Gene DNA Sequencing DNA was extracted from a single organism, a set of two organisms, or an ensemble comprised of more than two organisms. Extracted DNA was subjected to PCR to enrich the copy number of a selected conserved target gene (i.e., 16S rRNA or internal transcribed spacer). Amplified DNA of the enriched genes was sequenced using selected sequencing technology. Resulting sequences were trimmed, quality filtered, and clustered into operational taxonomic units (OTUs). Taxonomy was assigned to OTUs by sequence alignment to a reference database for the target gene of interest. The identity of microorganisms in each sample was inferred using the OTUs with assigned taxonomy.

Example 6: Microbial Identification for pH Modification

This example aims to identify the impact of select microbial compositions on their ability to lower, raise, or maintain the pH of the dough or baked good. pH can be assessed by a pH meter by measuring a single time point or over the length of the fermentation.

Method for Assaying pH Using a pH Meter or Probe

Each organism to be tested was cultured in isolation or as a part of a consortium in growth media and incubated at 32 °C for 24 hours. Cells were harvested by centrifugation and 0.1 g of centrifuged cell concentrate was retained for colony-forming unit (CFU) plating. To conduct CFU plating, 0.1 g of the retained cell concentrate was diluted in 1 mL of sterile water and then was serially diluted. Each serial dilution was spread onto solid media optimal for the growth of the specific organism. Each plate for CFU analysis was incubated for 24 hours at 32 °C and colonies were counted for the dilution factor that resulted in 30-100 total colonies on the respective plate. Cell counts for each culture were calculated using the colony count and back calculated using the dilution factor to get the total CFU/g for each organism to be tested. Wheat flour dough was prepared by mixing 1000 g all-purpose flour (King Arthur Baking Company, USA) 700 g distilled water, and 30 g salt, using a FAMAG IM-8 mixer (Fabbrica Macchine Alimentari Grillo, Italy) for each organism, set, or ensemble of organisms tested. Each organism, set, or ensemble of organisms was mixed into their respective dough at a normalized amount across all experimental doughs at $10^7$ to $10^{13}$ total cells per dough. Samples were taken for each dough at the conclusion of mixing to act as a baseline measurement. The dough was then left to ferment in an incubated or unincubated environment for 24-100 hours. The pH was continuously or periodically measured using a calibrated Pro2Go Portable pH meter (Mettler Toledo, USA) by interesting the probe into the dough. In other cases, pH was assessed using colorimetric or fluorescence-based assays in which dough or other medium was inoculated with the organism(s) and samples were evaluated at a single time point or over the course of fermentation.

Method of Assaying pH Using a Colorimetric Assay

Each organism to be tested was cultured in isolation or as a part of a consortium in liquid growth media and incubated at 32 °C for 24 hours. The indicator dye that fits the pH range to be tested was selected. For sourdough organisms, two of the most relevant are bromocresol green with a pH detection range between 3.1-6.5, and bromocresol purple with a pH range from 4.9-7.6. The indicator dye was diluted by adding 0.5 g of the dye to 500 mL of deionized water. Standards were made to generate a standard curve. For each standard required, 10 mL of deionized water was mixed with the appropriate levels of acid or base to generate standards that span the breadth of the range to be tested in regular intervals. For instance, if an eight-point standard curve was desired for testing with bromocresol green dye, the eight-point standard covered pH 3.1-6.5, using pH 0.5 as the interval between standards. 10 μL of diluted dye was added to the 10 mL standards just prior to conducting the experiment. In a clear, flat bottom, 96-well plate, 100 μL of each standard with dye was added to the appropriate number of wells. 1 μL of each culture to be tested was inoculated into 99 μL of fresh liquid growth media (pH 7) with 0.1% diluted dye to the remaining empty wells in the plate. The plate was incubated at 32 °C for 24-100 hours in a BioTek Synergy plate reader (Agilent Technologies, USA) with shaking. The plate reader was set to read the samples every 15 minutes. After the experiment was concluded, the standard curve was used to determine the absolute pH change and rate of pH change for each experimental well.

Figure 8:
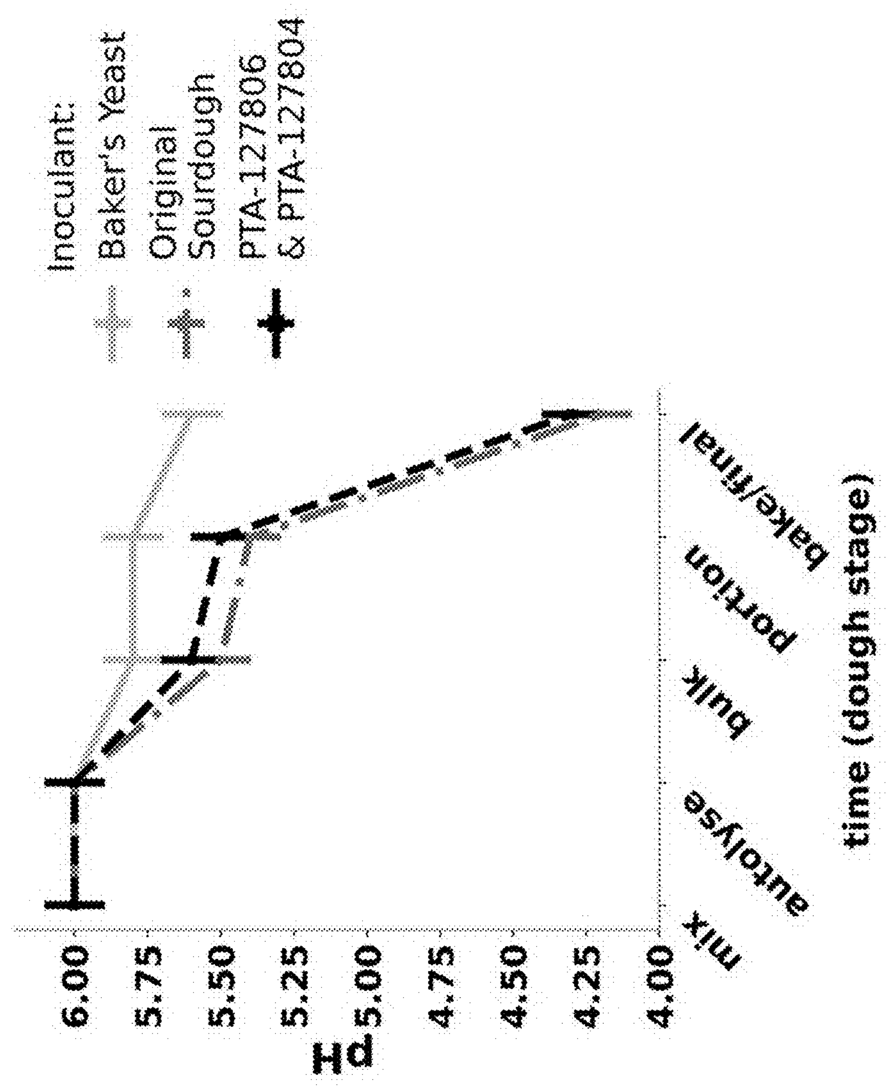
FIG. 8 shows the pH of dough across fermentation stages of baker's yeast, the original traditional sourdough starter, or a two strain inoculant comprising *Fructilactobacillus sanfranciscensis* (PTA-127806) and *Saccharomyces cerevisiae* (PTA-127804).

FIG. 8 shows the pH of dough across fermentation stages for baker's yeast, the original sourdough starter, or a two strain inoculant comprising *Fructilactobacillus sanfranciscensis* (PTA-127806) and *Saccharomyces cerevisiae* (PTA-127804). These results show that the two strain inoculant effectively reduced the pH of dough as well as the original sourdough.

Example 7: Microbial Identification for Rheological Benefit

This example aims to identify the impact of the microbial compositions described herein on rheological properties, such as extensibility or firmness, of dough and bread.

Method for Measuring Dough Extensibility by Rheometer

Each microorganism to be tested was cultured in isolation or as a part of a consortium in growth media and incubated at 32 °C for 24 hours. Cells were harvested by centrifugation and 0.1 g of centrifuged cell concentrate was retained for colony-forming unit (CFU) plating. To conduct CFU plating, 0.1 g of the retained cell concentrate was diluted in 1 mL of sterile water and then was serially diluted. Each serial dilution was spread onto solid media optimal for the growth of the specific organism. Each plate for CFU analysis was incubated for 24 hours at 32 °C and colonies are counted for the dilution factor that results in 30-100 total colonies on the respective plate. Cell counts for each culture were calculated using the colony count and back calculating using the dilution factor to get the total CFU/g for each organism to be tested. Wheat flour dough was prepared by mixing 1000 g all-purpose flour (King Arthur Baking Company, USA) 700 g distilled water, and 30 g salt, using a FAAMAG IM-8 mixer (Fabbrica Macchine Alimentari Grillo, Italy) for each organism, set, or ensemble of organisms to be tested. Each organism, set, or ensemble of organisms was mixed into their respective dough at a normalized amount across all experimental doughs at $10^7$ to $10^{13}$ total cells per dough. Samples were taken for each dough at the conclusion of mixing to act as a baseline measurement. The dough was incubated to allow for fermentation with samples taken periodically or at the fermentation endpoint.

Figure 9:
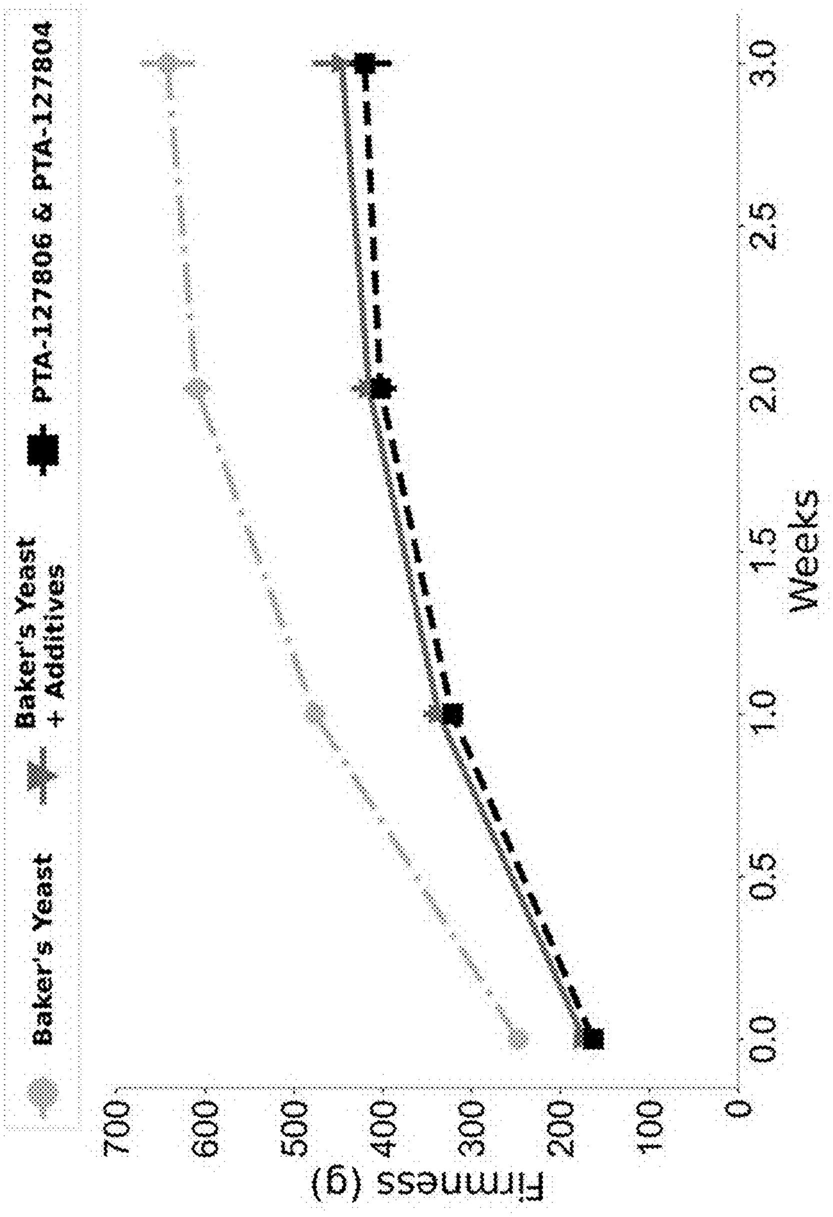
FIG. 9 shows the firmness across weeks from baking with baker's yeast, baker's yeast plus additives, or a two strain inoculant comprising *Fructilactobacillus sanfranciscensis* (PTA-127806) and *Saccharomyces cerevisiae* (PTA-127804).

Experimental dough samples were tested for small amplitude oscillatory shear using an MCR502 rheometer equipped with a 40 mm sand-blasted parallel plate geometry (Anton Paar, AUT). Dough loaded into the rheometer was allowed to sit for 5 minutes and measurements evaluating elasticity of the dough were collected in triplicate at 25 °C FIG. 9 shows firmness of dough overtime from using baker's yeast, yeast plus preservatives and conditioners (additives), or a two strain inoculant comprising *Fructilactobacillus sanfranciscensis* (PTA-127806) and *Saccharomyces cerevisiae* (PTA-127804). These results show that the two strain inoculant prevented staling of bread as well as baked goods made with preservatives.

Example 8: Microbial Identification for Leavening Ability

This example aims to identify the impact of select microbial compositions on their ability to leaven dough or bread.

Method for Determining Dough Leavening

Each organism to be tested was cultured in isolation or as a part of consortia in growth media and incubated at 32 °C for 24 hours. Cells were harvested by centrifugation and 0.1 g of centrifuged cell concentrate was retained for colony-forming unit (CFU) plating. To conduct CFU plating, 0.1 g of the retained cell concentrate was diluted in 1 mL of sterile water and then was serially diluted. Each serial dilution was spread onto solid media optimal for the growth of the specific organism. Each plate for CFU analysis was incubated for 24 hours at 32 °C and colonies were counted for the dilution factor that results in 30-100 total colonies on the respective plate. Cell counts for each culture were calculated using the colony count and back calculated using the dilution factor to get the total CFU/g for each organism to be tested. Wheat flour dough was prepared by mixing 1000 g all-purpose flour (King Arthur Baking Company, USA) 700 g distilled water, and 30 g salt, using a FAAMAG IM-8 mixer (Fabbrica Macchine Alimentari Grillo, Italy) for each organism, set, or ensemble of organisms to be tested. Each organism, set, or ensemble of organisms was mixed into their respective dough at a normalized amount across all experimental doughs at $10^7$ to $10^{13}$ total cells per dough.

A 5 g portion of dough from each experimental group was put into a 15 mL conical tube and centrifuged at 4,000 g for 2 minutes. Experimental doughs were left to ferment in an incubated or unincubated environment for 24-48 hours. A camera was preset to take photographs of the dough in the tubes every 10 minutes to generate a timelapse. The method for evaluation of total rise and rise rate was calculated as outlined by Landis et al. using the R package GrowthCurver (Landis et al. 2021).

Figure 10:
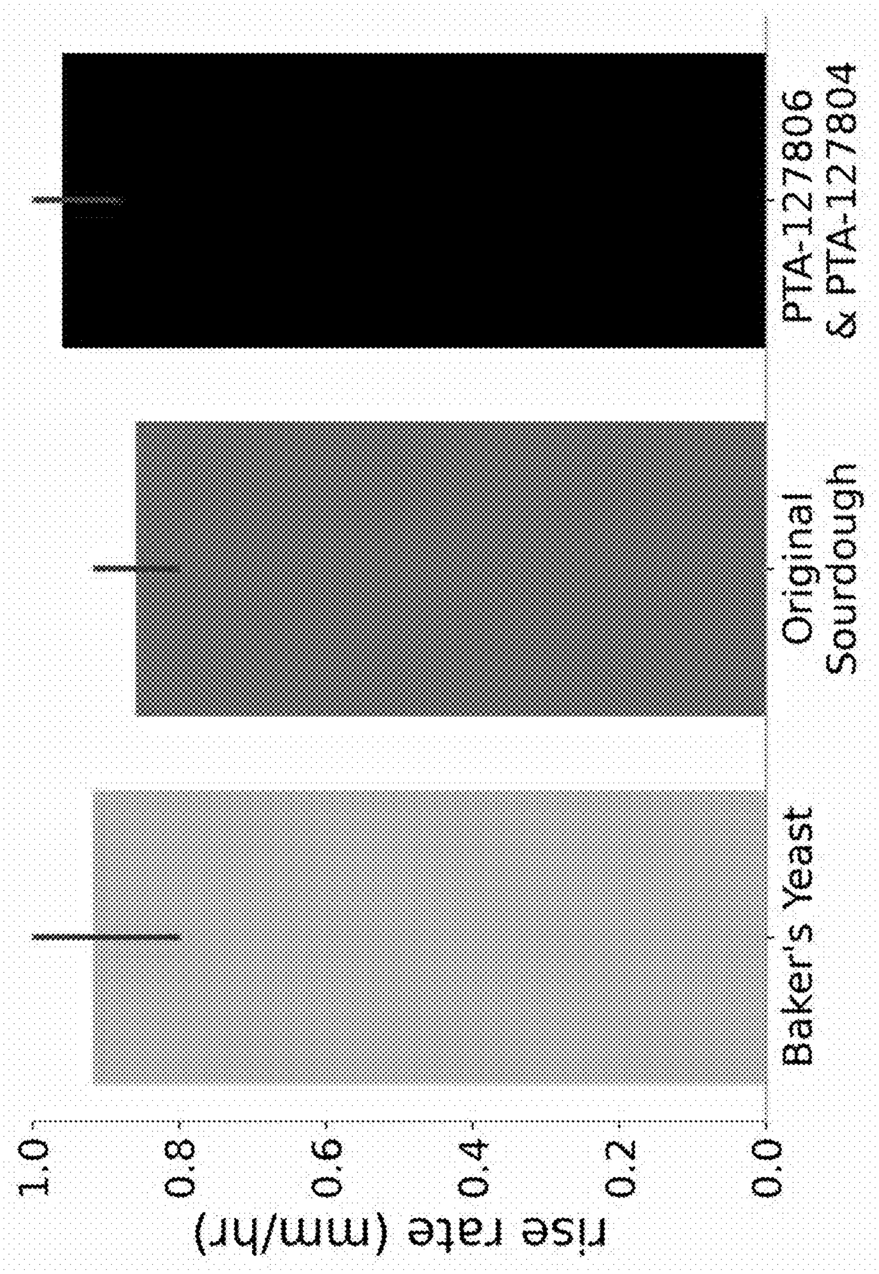
FIG. 10 shows the rise rate of baker's yeast, the original traditional sourdough starter, or a two strain inoculant comprising *Fructilactobacillus sanfranciscensis* (PTA-127806) and *Saccharomyces cerevisiae* (PTA-127804).

FIG. 10 shows the rise rate of baker's yeast, the original traditional sourdough starter, or a two strain inoculant comprising *Fructilactobacillus sanfranciscensis* (PTA-127806) and *Saccharomyces cerevisiae* (PTA-127804). These results show that the two strain inoculant raised dough at the same rate as baker's yeast and faster than the original sourdough.

Example 9: Microbial Identification for Organic Acid Generation

This example aims to identify the ability of select microbial compositions to generate organic acids in dough during fermentation.

Method for Measuring Organic Acids in Dough by Assessing Titratable Acidity (TTA)

Each organism to be tested is cultured in isolation or as a part of a consortium in growth media and incubated at 32 °C for 24 hours. Cells are harvested by centrifugation and 0.1 g of centrifuged cell concentrate is retained for colony-forming unit (CFU) plating. To conduct CFU plating, 0.1 g of the retained cell concentrate is diluted in 1 mL of sterile water and then is serially diluted. Each serial dilution is spread onto solid media optimal for the growth of the specific organism. Each plate for CFU analysis is incubated for 24 hours at 32 °C and colonies are counted for the dilution factor that results in 30-100 total colonies on the respective plate. Cell counts for each culture are calculated using the colony count and back calculating using the dilution factor to get the total CFU/g for each organism to be tested. Wheat flour dough is prepared by mixing 1000 g all-purpose flour (King Arthur Baking Company, USA) 700 g distilled water, and 30 g salt, using a FAMAG IM-8 mixer (Fabbrica Macchine Alimentari Grillo, Italy) for each organism, set, or ensemble of organisms to be tested.

Each organism, set, or ensemble of organisms is mixed into their respective dough at a normalized amount across all experimental doughs at $10^7$ to $10^{13}$ total cells per dough. Samples are taken for each dough at the conclusion of mixing to act as a baseline measurement. The dough is incubated to allow for fermentation with samples taken periodically or at the fermentation endpoint. For each experimental dough, 10 g of dough is added to 90 mL of deionized water and homogenized by vortexing for 3 minutes. While stirring the diluted dough mixture, 0.1 M NaOH is slowly added, and the pH of the mixture is recorded. Once the pH of the mixture equals 8.3, the experiment is concluded and TTA is reported as the total volume of NaOH added.

Method for Measuring Organic Acids in Dough by HPLC

Each organism to be tested is cultured in isolation or as a part of a consortium in growth media and incubated at 32 °C for 24 hours. Cells are harvested by centrifugation and 0.1 g of centrifuged cell concentrate is retained for colony-forming unit (CFU) plating. To conduct CFU plating, 0.1 g of the retained cell concentrate is diluted in 1 mL of sterile water and then is serially diluted. Each serial dilution is spread onto solid media optimal for the growth of the specific organism. Each plate for CFU analysis is incubated for 24 hours at 32 °C and colonies are counted for the dilution factor that results in 30-100 total colonies on the respective plate. Cell counts for each culture are calculated using the colony count and back calculating using the dilution factor to get the total CFU/g for each organism to be tested. Wheat flour dough is prepared by mixing 1000 g all-purpose flour (King Arthur Baking Company, USA) 700 g distilled water, and 30 g salt, using a FAMAG IM-8 mixer (Fabbrica Macchine Alimentari Grillo, Italy) for each organism, set, or ensemble of organisms to be tested.

Each organism, set, or ensemble of organisms is mixed into their respective dough at a normalized amount across all experimental doughs at $10^7$ to $10^{13}$ total cells per dough. Samples are taken for each dough at the conclusion of mixing to act as a baseline measurement. The dough is incubated to allow for fermentation with samples taken periodically or at the fermentation endpoint.

For each experimental dough, lg of dough is homogenized in 10 mL of deionized water by vortex for 10 minutes and then centrifuged at 12,000 g for 10 minutes. The supernatant is harvested, and 7 mL of supernatant is added to 0.2 mL potassium II hexaferrocyanate, (0.085 mol/L) and 0.2 mL zinc sulfate (0.25 mol/L). Samples are vortexed, centrifuged at 12,000 g for 10 minutes, and filtered through a 0.22 μm filter. The filtrate is then run on an HPLC/RI/UV system at 60 °C using 0.005 mol/L H2SO4 at a flow rate of 0.6 ml/min and analyzed for the presence of organic acids.

Example 10: Microbial Identification for Protein Degradation

This example aims to identify the ability of select microbial compositions to degrade proteins in the dough and/or baked good.

Method for Assaying Protein Hydrolysis in Dough

Each organism to be tested is cultured in isolation or as a part of a consortium in growth media and incubated at 32 °C for 24 hours. Cells are harvested by centrifugation and 0.1 g of centrifuged cell concentrate is retained for colony-forming unit (CFU) plating. To conduct CFU plating, 0.1 g of the retained cell concentrate is diluted in 1 mL of sterile water and then is serially diluted. Each serial dilution is spread onto solid media optimal for the growth of the specific organism. Each plate for CFU analysis is incubated for 24 hours at 32 °C and colonies are counted for the dilution factor that results in 30-100 total colonies on the respective plate. Cell counts for each culture are calculated using the colony count and back calculating using the dilution factor to get the total CFU/g for each organism to be tested. Wheat flour dough is prepared by mixing 1000 g all-purpose flour (King Arthur Baking Company, USA) 700 g distilled water, and 30 g salt, using a FAMAG IM-8 mixer (Fabbrica Macchine Alimentari Grillo, Italy) for each organism, set, or ensemble of organisms to be tested. Each organism, set, or ensemble of organisms is mixed into their respective dough at a normalized amount across all experimental doughs at $10^7$ to $10^{13}$ total cells per dough. Samples are taken for each dough at the conclusion of mixing to act as a baseline measurement. Experimental doughs are left to ferment in an incubated or unincubated environment for 24-100 hours and samples are taken periodically across the fermentation. In addition, 8 samples for the generation of a standard curve are generated using leucine. The concentration of leucine for generating the standard curve at 0.125, 0.25, 0.375, 0.5, 0.625, 0.75, 0.875, 1.0 mmol/L. Protein hydrolysis is measured for each experimental and standard curve sample using the Trinitrobenzenesulfonic acid method to measure free amino groups ($NH_2$) (Adler-Nissen 1979; Zotta et al. 2006). To do so, 0.25 g of each dough or leucine stand control sample to be tested is mixed with 2.0 mL of phosphate buffer (pH 8.5) in a tube to which 2.0 mL of 0.1% Trinitrobenzenesulfonic acid is added. The tube is vortexed, wrapped in aluminum foil to prevent light exposure, and incubated at 50 °C for 60 minutes. At the conclusion of the incubation, 4.0 mL of 0.1N HCL is added to stop the reaction, and the tube is incubated at room temperature for 30 minutes. 100 L from the experimental and standard curve samples are added to a clear, flat bottom 96 well plate and are read by a BioTek Synergy plate reader at 340 nM (Agilent Technologies, USA). After the experiment is concluded, the standard curve can be used to determine the protein degradation in each experimental well.

Example 11: Microbial Identification for Production of Peptides

This example aims to identify the ability of select microbial compositions to produce peptides in the dough and/or baked good.

Method for Identifying Antioxidant Peptides in Dough

Each organism to be tested is cultured in isolation or as a part of a consortium in growth media and incubated at 32 °C for 24 hours. Cells are harvested by centrifugation and 0.1 g of centrifuged cell concentrate is retained for colony-forming unit (CFU) plating. To conduct CFU plating, 0.1 g of the retained cell concentrate is diluted in 1 mL of sterile water and then is serially diluted. Each serial dilution is spread onto solid media optimal for the growth of the specific organism. Each plate for CFU analysis is incubated for 24 hours at 32 °C and colonies are counted for the dilution factor that results in 30-100 total colonies on the respective plate. Cell counts for each culture are calculated using the colony count and back calculating using the dilution factor to get the total CFU/g for each organism to be tested. Wheat flour dough is prepared by mixing 1000 g all-purpose flour (King Arthur Baking Company, USA) 700 g distilled water, and 30 g salt, using a FAMAG IM-8 mixer (Fabbrica Macchine Alimentari Grillo, Italy) for each organism, set, or ensemble of organisms to be tested. Each organism, set, or ensemble of organisms is mixed into their respective dough at a normalized amount across all experimental doughs at $10^7$ to $10^{13}$ total cells per dough. Samples are taken for each dough at the conclusion of mixing to act as a baseline measurement. Experimental doughs are left to ferment in an incubated or unincubated environment for 24-100 hours and samples are taken periodically across the fermentation. Water/salt-soluble extracts are prepared from each dough using a method developed by Weiss et al. (Weiss, Vogelmeier, and Gorg 1993). Briefly, 7.5 g of each dough is diluted in 30 mL of 50 mM Tris-HCL (pH 8.8) and incubated at 4 °C for 1 hour. The incubated sample is centrifuged at 20,000 g for 20 minutes. The supernatant is retained for analysis of antioxidant peptide content. Inhibition of linoleic acid autoxidation is measured as described by Coda et al. (Coda et al. 2012) with the exception that the samples are not freeze-dried. For each sample 1 mL of supernatant is added to 1 mL of 50 mM linoleic acid which was diluted in 100% ethanol. The sample is incubated in the dark at 60 °C for 8 days. Positive antioxidant controls, butylated hydroxytoluene (1 mg/ml), and α-tocopherol (1 mg/ml) were treated in the same way as the extracted supernatants. After incubation, 100 μL of sample is mixed with 4.7 mL of 75% (vol/vol) ethanol, 100 μL of 30% (wt/vol) ammonium thiocyanate, 100 μL of 0.02 M ferrous chloride diluted in 1M HCL. The samples are incubated for 3 minutes, added to a clear, flat bottom 96 well plate, and read by a BioTek Synergy plate reader at 500 nM (Agilent Technologies, USA). The results for experimental samples are compared to the positive control references and relative antioxidant capacity is assessed.

Example 12: Microbial Identification for Degradation of Chemical Compounds

This example aims to identify the ability of select microbial compositions to degrade chemical compounds and chemical precursors in the dough and/or baked good.

Method for Identifying Acrylamide in Dough

Each organism to be tested is cultured in isolation or as a part of a consortium in growth media and incubated at 32 °C for 24 hours. Cells are harvested by centrifugation and 0.1 g of centrifuged cell concentrate is retained for colony-forming unit (CFU) plating. To conduct CFU plating, 0.1 g of the retained cell concentrate is diluted in 1 mL of sterile water and then is serially diluted. Each serial dilution is spread onto solid media optimal for the growth of the specific organism. Each plate for CFU analysis is incubated for 24 hours at 32 °C and colonies are counted for the dilution factor that results in 30-100 total colonies on the respective plate. Cell counts for each culture are calculated using the colony count and back calculating using the dilution factor to get the total CFU/g for each organism to be tested. Wheat flour dough is prepared by mixing 1000 g all-purpose flour (King Arthur Baking Company, USA) 700 g distilled water, and 30 g salt, using a FAMAG IM-8 mixer (Fabbrica Macchine Alimentari Grillo, Italy) for each organism, set, or ensemble of organisms to be tested. Each organism, set, or ensemble of organisms is mixed into their respective dough at a normalized amount across all experimental doughs at $10^7$ to $10^{13}$ total cells per dough. Samples are taken for each dough at the conclusion of mixing to act as a baseline measurement. Experimental doughs are left to ferment in an incubated or unincubated environment for 24-100 hours and samples are taken periodically across the fermentation. Assessment of acrylamide in dough is done using the Acrylamide Starter Kit for UPLC MS/MS (Waters Corporation, USA) and liquid chromatography-tandem mass spectrometry (LC-MS/MS) using the methods outlined by the kit manual and Diana et al. ("Free Amino Acids, Acrylamide and Biogenic Amines in Gamma-Aminobutyric Acid Enriched Sourdough and Commercial Breads" 2014). Briefly, lg of dough is taken from each sample and an isotopically labeled internal standard (Acrylamide d3) is added to the samples prior to extraction in order to correct for any variability during extraction. Samples are extracted using the Acrylamide Starter Kit for UPLC MS/MS by the manufacturer-recommended protocol. Extracts are cleaned up using Dispersive solid phase extraction tubes containing 300 mg of secondary amine sorbent and 900 mg of MgSO4. The extract is then evaporated and reconstituted in 0.1% formic acid. The reconstituted extract is then evaluated by LC-MS/MS using parameters outlined in the Acrylamide Starter Kit for UPLC MS/MS manual.

Example 13: Microbial Identification for Degradation and/or Utilization of Carbohydrates This example aims to identify the ability of select microbial compositions to degrade and/or utilize simple and/or complex carbohydrates in the dough and/or baked good.

Method for Evaluating Carbohydrate Utilization

Each organism to be tested is cultured in isolation or as a part of a consortium in growth media and incubated at 32 °C for 24 hours. Each culture is centrifuged at 3,000 g for 10 minutes, cells are harvested and resuspended in a carbon source and electron donor free medium with 0.017% (w/v) bromocresol purple as an indicator of acidification of carbohydrates. Add the resuspended culture dropwise to each well of the 50 wells on an API50 CH test strip (bioMerieux SA, FRA) and incubate the strip at 32 °C for 24 to 48 hours. Carbohydrates tested by the assay include d-galactose, d-glucose, d-fructose, maltose, glycogen, aesculin/ferric citrate, starch, glycerol, erythritol, d-arabinose, 1-arabinose, d-ribose, d-xylose, 1-xylose, methyl 3-d-xylopyranoside, d-cellobiose, d-adonitol, d-lactose, d-saccharose, d-trehalose, d-melibiose, d-mannose, 1-arabitol, 1-sorbose, 1-rhamnose, dulcitol, inositol, d-mannitol, d-sorbitol, methyl d-mannopyranoside, methyl d-glucopyranoside, N-acetyl glucosamine, amygdalin, arbutin, melezitose, raffinose, xylitol, inulin, salicin, gentiobiose, turanose, d-lyxose, d-tagatose, d-fucose, 1-fucose, d-arabitol, potassium gluconate, potassium 2-ketogluconate and potassium 5-ketogluconate. At the conclusion of the incubation check the strip for qualitative acidification of the growth media by color change, if the carbohydrate has been utilized the media in the well will be yellow, if it has not been utilized the media will remain purple.

Example 14: Microbial Identification for Generation of Aroma and Flavor Compounds This example aims to identify the ability of select microbial compositions that generate compounds that enhance the flavor or aroma in the dough and/or baked good.

Method for Identification and Quantitation of Volatile Flavor and Aroma Compounds in Bread Each organism to be tested is cultured in isolation or as a part of consortia in growth media and incubated at 32 °C for 24 hours. Cells are harvested by centrifugation and 0.1 g of centrifuged cell concentrate is retained for colony-forming unit (CFU) plating. To conduct CFU plating, 0.1 g of the retained cell concentrate is diluted in 1 mL of sterile water and then is serially diluted. Each serial dilution is spread onto solid media optimal for the growth of the specific organism. Each plate for CFU analysis is incubated for 24 hours at 32 °C and colonies are counted for the dilution factor that results in 30-100 total colonies on the respective plate. Cell counts for each culture are calculated using the colony count and back calculating using the dilution factor to get the total CFU/g for each organism to be tested. Wheat flour dough is prepared by mixing 1000 g all-purpose flour (King Arthur Baking Company, USA) 700 g distilled water, and 30 g salt, using a FAMAG IM-8 mixer (Fabbrica Macchine Alimentari Grillo, Italy) for each organism, set, or ensemble of organisms to be tested. Each organism, set, or ensemble of organisms is mixed into their respective dough at a normalized amount across all experimental doughs at $10^7$ to $10^{13}$ total cells per dough. Experimental doughs are left to ferment in an incubated or unincubated environment for 24-100 hours and then baked. Baked bread is then evaluated for volatile aroma and flavor compounds by headspace solid-phase microextraction (HS-SPME) followed by gas chromatography-mass spectrometry (GC-MS) as detailed by Aslankoohi et al. (Aslankoohi et al. 2016). For the solid-phase extraction, 5.0 g of baked bread is put in a sealed glass vial and the volatiles are sampled using a triphase DVB/Carboxen/PDMS 50/30 m SPME fiber. Volatiles from the fiber are injected into a gas chromatograph-mass spectrometer by heating the fiber at 250 °C for 5 minutes. The GC-MS is equipped with a non-polar column and 1.4 ml/min helium is used for the carrier. The temperature of the during measurement is held at 36 °C for 10 minutes and raised by 6 °C a minute until 220 °C is reached. The spectra of volatile compounds are then deconvoluted and matched to a reference library for identification.

Example 15: Microbial Identification for Enhancement of Nutritional Qualities in Bread and Dough This example aims to identify the ability of select microbial compositions that enhance the nutritional quality in the dough and/or baked good.

Method to Assay Free Mineral Content in Bread

Each organism to be tested is cultured in isolation or as a part of consortia in growth media and incubated at 32 °C for 24 hours. Cells are harvested by centrifugation and 0.1 g of centrifuged cell concentrate is retained for colony-forming unit (CFU) plating. To conduct CFU plating, 0.1 g of the retained cell concentrate is diluted in 1 mL of sterile water and then is serially diluted. Each serial dilution is spread onto solid media optimal for the growth of the specific organism. Each plate for CFU analysis is incubated for 24 hours at 32 °C and colonies are counted for the dilution factor that results in 30-100 total colonies on the respective plate. Cell counts for each culture are calculated using the colony count and back calculating using the dilution factor to get the total CFU/g for each organism to be tested. Wheat flour dough is prepared by mixing 1000 g all-purpose flour (King Arthur Baking Company, USA) 700 g distilled water, and 30 g salt, using a FAMAG IM-8 mixer (Fabbrica Macchine Alimentari Grillo, Italy) for each organism, set, or ensemble of organisms to be tested. Each organism, set, or ensemble of organisms is mixed into their respective dough at a normalized amount across all experimental doughs at $10^7$ to $10^{13}$ total cells per dough. Experimental doughs are left to ferment in an incubated or unincubated environment for 24-100 hours and then baked. Baked bread is evaluated for free mineral content by methods outlined by Cizeikiene et al. (Cizeikiene et al. 2015). Soluble minerals are extracted from each experimental bread by combining 10 g baked bread with 50 mL deionized water and vortexed for 30 minutes to homogenize the sample. The samples are then centrifuged at 3,000 g for 5 minutes. The resulting supernatant is retained, and the pellet is washed with 50 mL of 0.9% NaCl (pH 2.0) and incubated at room temperature for 30 minutes. The samples are centrifuged, and the supernatant is retained. This process of washing is repeated twice more with 0.9% NaCl (pH 7.0) and the supernatant from each step is pooled together at completion. The pooled supernatant is then dried in a 105 °C-oven followed by washing in a muffle oven at 500 °C Calcium, zinc, iron, and manganese content is determined using a Spectr AA-Plus atomic absorption spectrophotometer by the Cereal and Grain Association AACC method 40-70.

Example 16: Microbial Identification for Environmental Condition Tolerance

This example aims to identify the ability of select microbial compositions that maintain viability across a broad range of environmental conditions.

Method to Assay Viability of Organisms Grown in Hypersaline Growth Media

Optimal growth media is determined for each organism to be tested and the organism is grown to max optical density in the optimal media. Solid media is prepared with a range of gradually increasing NaCl concentrations and 200 μL of liquid culture is added to each plate. Plates are incubated for 24 hours at 32 °C and colonies are counted for each dilution to determine the salt tolerance of each organism.

Numbered Embodiments

Embodiment 1. A composition comprising a purified population of one or more microorganisms comprising a nucleic acid sequence that shares at least 97% sequence identity with a nucleic acid sequence selected from SEQ ID NOs: 1-272; and a food-grade carrier or excipient.

Embodiment 2. The composition of embodiment 1, wherein the purified population of one or more microorganisms comprises a nucleic acid sequence that shares at least 98% sequence identity with a nucleic acid sequence selected from SEQ ID NOs: 1-272.

Embodiment 3. The composition of embodiment 1, wherein the purified population of one or more microorganisms comprises a nucleic acid sequence that shares at least 99% sequence identity with a nucleic acid sequence selected from SEQ ID NOs: 1-272.

Embodiment 4. The composition of embodiment 1, wherein the purified population of one or more microorganisms comprises a nucleic acid sequence selected from SEQ ID NOs: 1-272.

Embodiment 5. The composition of embodiment 1, wherein the purified population of one or more microorganisms comprises a yeast with an ITS nucleic acid sequence sharing at least 97%, at least 98%, or at least 99% sequence identity with SEQ ID NO: 207 or SEQ ID NO: 267.

Embodiment 6. The composition of embodiment 1, wherein the purified population of one or more microorganisms comprises a yeast with an ITS nucleic acid sequence comprising SEQ ID NO: 207 or SEQ ID NO: 267.

Embodiment 7. The composition of embodiment 1, wherein the purified population of one or more microorganisms comprises a *Saccharomyces cerevisiae* as deposited as PTA-127804.

Embodiment 8. The composition of embodiment 1, wherein the purified population of one or more microorganisms comprises a yeast with an ITS nucleic acid sequence sharing at least 97%, at least 98%, or at least 99% sequence identity with SEQ ID NO: 159, SEQ ID NO: 268, or SEQ ID NO: 269.

Embodiment 9. The composition of embodiment 1, wherein the purified population of one or more microorganisms comprises a yeast with an ITS nucleic acid sequence comprising SEQ ID NO: 159, SEQ ID NO: 268, or SEQ ID NO: 269.

Embodiment 10. The composition of embodiment 1, wherein the purified population of one or more microorganisms comprises a *Kazachstania humilis* as deposited as PTA-127805.

Embodiment 11. The composition of embodiment 1, wherein the purified population of one or more microorganisms comprises a bacterium with a 16S nucleic acid sequence sharing at least 97%, at least 98%, or at least 99% sequence identity with SEQ ID NO: 4 or SEQ ID NO: 270.

Embodiment 12. The composition of embodiment 1, wherein the purified population of one or more microorganisms comprises a bacterium with a 16S nucleic acid sequence comprising SEQ ID NO: 4 or SEQ ID NO: 270.

Embodiment 13. The composition of embodiment 1, wherein the purified population of one or more microorganisms comprises a *Fructilactobacillus sanfranciscensis* as deposited as PTA-127806.

Embodiment 14. The composition of embodiment 1, wherein the purified population of one or more microorganisms comprises a bacterium with a 16S nucleic acid sequence sharing at least 97%, at least 98%, or at least 99% sequence identity with SEQ ID NO: 10 or SEQ ID NO: 271.

Embodiment 15. The composition of embodiment 1, wherein the purified population of one or more microorganisms comprises a bacterium with a 16S nucleic acid sequence comprising SEQ ID NO: 10 or SEQ ID NO: 271.

Embodiment 16. The composition of embodiment 1, wherein the purified population of one or more microorganisms comprises a *Pediococcus pentosaceus* as deposited as PTA-127807.

Embodiment 17. The composition of embodiment 1, wherein the purified population of one or more microorganisms comprises a bacterium with a 16S nucleic acid sequence sharing at least 97%, at least 98%, or at least 99% sequence identity with SEQ ID NO: 8 or SEQ ID NO: 272.

Embodiment 18. The composition of embodiment 1, wherein the purified population of one or more microorganisms comprises a bacterium with a 16S nucleic acid sequence comprising SEQ ID NO: 8 or SEQ ID NO: 272.

Embodiment 19. The composition of embodiment 1, wherein the purified population of one or more microorganisms comprises a *Levilactobacillus brevis* as deposited as PTA-127808.

Embodiment 20. The composition of embodiment 1, wherein the purified population of one or more microorganisms comprises:

(a) a yeast with an ITS nucleic acid sequence sharing at least 97%, at least 98%, at least 99%, or 100% sequence identity to SEQ ID NO: 207 or SEQ ID NO: 267;

(b) a yeast with an ITS nucleic acid sequence sharing at least 97%, at least 98%, at least 99%, or 100% sequence identity to SEQ ID NO: 159, SEQ ID NO: 268, or SEQ ID NO: 269;

(c) a bacterium with a 16S nucleic acid sequence sharing at least 97%, at least 98%, at least 99%, or 100% sequence identity to SEQ ID NO: 4 or SEQ ID NO: 270;

(d) a bacterium with a 16S nucleic acid sequence sharing at least 97%, at least 98%, at least 99%, or 100% sequence identity to SEQ ID NO: 10 or SEQ ID NO: 271; and/or (e) a bacterium with a 16S nucleic acid sequence sharing at least 97%, at least 98%, at least 99%, or 100% sequence identity to SEQ ID NO: 8 or SEQ ID NO: 272.

Embodiment 21. The composition of embodiment 1, wherein the purified population of one or more microorganisms comprises:

(a) a yeast with an ITS nucleic acid sequence sharing at least 97%, at least 98%, at least 99%, or 100% sequence identity to SEQ ID NO: 207 or SEQ ID NO: 267; and/or (b) a bacterium with a 16S nucleic acid sequence sharing at least 97%, at least 98%, at least 99%, or 100% sequence identity to SEQ ID NO: 4 or SEQ ID NO: 270.

Embodiment 22. The composition of embodiment 1, wherein the purified population of one or more microorganisms comprises:

(a) a yeast with an ITS nucleic acid sequence sharing at least 97%, at least 98%, at least 99%, or 100% sequence identity to SEQ ID NO: 207 or SEQ ID NO: 267; and (b) a bacterium with a 16S nucleic acid sequence sharing at least 97%, at least 98%, at least 99%, or 100% sequence identity to SEQ ID NO: 4 or SEQ ID NO: 270.

Embodiment 23. The composition of embodiment 1, wherein the purified population of one or more microorganisms comprises:

(a) a *Saccharomyces cerevisiae* as deposited as PTA-127804;

(b) a *Kazachstania humilis* as deposited as PTA-127805;

(c) a *Fructilactobacillus sanfranciscensis* as deposited as PTA-127806;

(d) a *Pediococcus pentosaceus* as deposited as PTA-127807; and/or (e) a *Levilactobacillus brevis* as deposited as PTA-127808.

Embodiment 24. The composition of embodiment 1, wherein the purified population of one or more microorganisms comprises:

(a) a *Saccharomyces cerevisiae* as deposited as PTA-127804; and/or (b) a *Fructilactobacillus sanfranciscensis* as deposited as PTA-127806.

Embodiment 25. The composition of embodiment 1, wherein the purified population of one or more microorganisms comprises:

(a) a *Saccharomyces cerevisiae* as deposited as PTA-127804; and (b) a *Fructilactobacillus sanfranciscensis* as deposited as PTA-127806.

Embodiment 26. The composition of any one of embodiments 1-25, wherein the one or more microorganisms is lyophilized.

Embodiment 27. The composition of any one of embodiments 1-26, wherein the one or more microorganisms is encapsulated.

Embodiment 28. The composition of any one of embodiments 1-27, wherein the one or more microorganisms is present in the composition at about $10^2$ CFU/g or more.

Embodiment 29. The composition of embodiment 28, wherein the one or more microorganisms is present in the composition at about $10^9$ CFU/g, about $10^{10}$ CFU/g, about $10^{11}$ CFU/g, about $10^{12}$ CFU/g, about $10^{13}$ CFU/g, or about $10^{14}$ CFU/g.

Embodiment 30. The composition of any one of embodiments 1-29, wherein the composition comprises one or more additional preservatives.

Embodiment 31. The composition of any one of embodiments 1-30, wherein the composition comprises one or more additional flavoring agents.

Embodiment 32. The composition of any one of embodiments 1-31, wherein the composition comprises one or more additional leavening agents.

Embodiment 33. The composition of any one of embodiments 1-32, wherein the composition is formulated as a dry powder, food ingredient, food preparation, food supplement, water additive, moisture-stabilized additive, consumable, solid, gel, liquid, or dough.

Embodiment 34. The composition of any one of embodiments 1-32, wherein the composition is a food.

Embodiment 35. The composition of any one of embodiments 1-32, wherein the composition is a dough.

Embodiment 36. The composition of any one of embodiments 1-32, wherein the composition is a starter culture for bakery good production.

Embodiment 37. The composition of any one of embodiments 1-32, wherein the composition is a baked good.

Embodiment 38. The composition of embodiment 37, wherein the baked good is a bread.

Embodiment 39. The composition of embodiment 37, wherein the baked good is a sourdough bread.

Embodiment 40. A method for improving the fermentation of a food product, the method comprising admixing an effective amount of the composition of any one of embodiments 1-32 to the food product.

Embodiment 41. A method of producing a dough, the method comprising admixing an effective amount of the composition of any one of embodiments 1-32 to the dough.

Embodiment 42. A method of increasing the shelf-life of a dough or baked good, the method comprising admixing an effective amount of the composition of any one of embodiments 1-32 to the dough or baked good.

Embodiment 43. A method of lowering the pH of a dough, the method comprising admixing an effective amount of the composition of any one of embodiments 1-32 to the dough.

Embodiment 44. A method of increasing organic acids in a dough, the method comprising admixing an effective amount of the composition of any one of embodiments 1-32 to the dough.

Embodiment 45. A method of enhancing rheological properties of a dough, the method comprising admixing an effective amount of the composition of any one of embodiments 1-32 to the dough.

Embodiment 46. A method of increasing protein degradation in a dough, the method comprising admixing an effective amount of the composition of any one of embodiments 1-32 to the dough.

Embodiment 47. A method of increasing peptide or protein production in a dough, the method comprising admixing an effective amount of the composition of any one of embodiments 1-32 to the dough.

Embodiment 48. A method of increasing degradation of complex and/or simple carbohydrates in a dough, the method comprising admixing an effective amount of the composition of any one of embodiments 1-32 to the dough.

Embodiment 49. A method of increasing degradation of chemical compounds or chemical precursors in a dough, the method comprising admixing an effective amount of the composition of any one of embodiments 1-32 to the dough.

Embodiment 50. A method of increasing the flavor or aroma of a dough, the method comprising admixing an effective amount of the composition of any one of embodiments 1-32 to the dough.

Embodiment 51. A method of increasing leavening ability of a dough, the method comprising admixing an effective amount of the composition of any one of embodiments 1-32 to the dough.

Embodiment 52. A method of increasing nutritional quality of a dough, the method comprising admixing an effective amount of the composition of any one of embodiments 1-32 to the dough.

Embodiment 53. The method of embodiment 52, wherein the method reduces the glycemic index of the dough or a baked food product of the dough.

Embodiment 54. The method of embodiment 52, wherein the method reduces glutens in the dough or a baked food product of the dough.

Embodiment 55. A method of modulating activity of one or more microorganisms in a dough, the method comprising admixing an effective amount of the composition of any one of embodiments 1-32 to the dough.

Embodiment 56. A method for improving fermentation of a dough, comprising: admixing an effective amount of a composition comprising a purified population of one or more microorganisms comprising a nucleic acid sequence that shares at least 97% sequence identity with a nucleic acid sequence selected from SEQ ID NOs: 1-272 to the dough.

Embodiment 57. A method for increasing the shelf-life of a dough, comprising: admixing an effective amount of a composition comprising a purified population of one or more microorganisms comprising a nucleic acid sequence that shares at least 97% sequence identity with a nucleic acid sequence selected from SEQ ID NOs: 1-272 to the dough.

Embodiment 58. A method of enhancing rheological properties of a dough, the method comprising: admixing an effective amount of a composition comprising a purified population of one or more microorganisms comprising a nucleic acid sequence that shares at least 97% sequence identity with a nucleic acid sequence selected from SEQ ID NOs: 1-272 to the dough.

Embodiment 59. The method of any one of embodiments 55-58, wherein the admixture results in a baked food product.

Embodiment 60. The method of embodiment 59, wherein the baked food product is a sourdough bread.

Embodiment 61. A method for increasing the shelf-life of a baked food product, comprising: admixing an effective amount of a composition comprising a purified population of one or more microorganisms comprising a nucleic acid sequence that shares at least 97% sequence identity with a nucleic acid sequence selected from SEQ ID NOs: 1-272 to a dough, wherein the admixture results in the baked food product with an increased shelf-life.

Embodiment 62. The method of any one of embodiments 40 to 61, wherein the method comprises incubating the admixture for a period of time.

Embodiment 63. The method of embodiment 62, wherein the admixture is incubated for at least 15 minutes, at least 30 minutes, at least 1 hour, at least 2 hours, at least 6 hours, at least 12 hours, at least 24 hours, at least 36 hours, at least 48 hours, at least 60 hours, at least 72 hours, at least 84 hours, at least 96 hours, at least 108 hours, or at least 120 hours.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

REFERENCES CITED

Albagli, G.; do Monte Schwartz, I.; Amaral, P. F. F.; Ferreira, T. F.; Finotelli, P. V. How dried sourdough starter can enable and spread the use of sourdough bread. LWT 2021, 149, 111888.

Adler-Nissen, J. 1979. "Determination of the Degree of Hydrolysis of Food Protein Hydrolysates by Trinitrobenzenesulfonic Acid." *Journal of Agricultural and Food Chemistry* 27 (6): 1256-62.

Arora, K., Ameur, H., Polo, A., Di Cagno, R., Rizzello, C. G., and Gobbetti, M. (2021). Thirty years of knowledge on sourdough fermentation: a systematic review. Trends Food Sci. Technol. 108, 71-83.

Aslankoohi, Elham, Beatriz Herrera-Malaver, Mohammad Naser Rezaei, Jan Steensels, Christophe M. Courtin, and Kevin J. Verstrepen. 2016. "Non-Conventional Yeast Strains Increase the Aroma Complexity of Bread." *PloS One* 11 (10): e0165126.

Carbonetto, Belén, Thibault Nidelet, Stephane Guezenec, Marc Perez, Diego Segond, and Delphine Sicard. 2020. "Interactions between Yeast Species and Lactic Acid Bacteria in Sourdough." *Microorganisms* 8 (2). https://doi.org/10.3390/microorganisms8020240.

Cavallo, Noemi, Maria De Angelis, Maria Calasso, Maurizio Quinto, Annalisa Mentana, Fabio Minervini, Stefan Cappelle, and Marco Gobbetti. 2017. "Microbial Cell-Free Extracts Affect the Biochemical Characteristics and Sensorial Quality of Sourdough Bread." Food Chemistry 237 (December): 159-68.

Chavan, Rupesh S., and Shraddha R. Chavan. 2011. "Sourdough Technology-A Traditional Way for Wholesome Foods: A Review." *Comprehensive Reviews in Food Science and Food Safety* 10 (3): 169-82.

Cizeikiene, Dalia, Grazina Juodeikiene, Elena Bartkiene, Jonas Damasius, and Algimantas Paskevicius. 2015. "Phytase Activity of Lactic Acid Bacteria and Their Impact on the Solubility of Minerals from Wholemeal Wheat Bread." *International Journal of Food Sciences and Nutrition* 66 (7): 736-42.

Cizeikiene, D.; Jagelaviciute, J.; Stankevicius, M.; Maruska, A. Thermophilic lactic acid bacteria affect the characteristics of sourdough and whole-grain wheat bread. Food Biosci. 2020, 38, Coda, Rossana, Carlo Giuseppe Rizzello, Daniela Pinto, and Marco Gobbetti. 2012. "Selected Lactic Acid Bacteria Synthesize Antioxidant Peptides during Sourdough Fermentation of Coda, Rossana, Angela Cassone, Carlo G. Rizzello, Luana Nionelli, Gianluigi Cardinali, and Marco Gobbetti. 2011. "Antifungal Activity of Wickerhamomyces *Anomalus* and *Lactobacillus Plantarum* during Sourdough Fermentation: Identification of Novel Compounds and Long-Term Effect during Storage of Wheat Bread." Applied and Environmental Microbiology 77 (10): 3484-92.Cereal Flours." *Applied and Environmental Microbiology* 78 (4): 1087-96.

Corsetti, A., M. Gobbetti, B. De Marco, F. Balestrieri, F. Paoletti, L. Russi, and J. Rossi. 2000. "Combined Effect of Sourdough Lactic Acid Bacteria and Additives on Bread Firmness and Staling." Journal of Agricultural and Food Chemistry 48 (7): 3044-51.

Crowley, Peter. 2004. Factors Affecting Bread Crumb Structure as Evaluated by Digital Image Analysis.

De MAN, J. C., M. Rogosa, and M. Elisabeth Sharpe. 1960. "A MEDIUM FOR THE CULTIVATION OF LACTOBACILLI." *The Journal of Applied Bacteriology* 23 (1): 130-35.

Di Cagno, Raffaella, Carlo G. Rizzello, Maria De Angelis, Angela Cassone, Giammaria Giuliani, Anna Benedusi, Antonio Limitone, Rosalinda F. Surico, and Marco Gobbetti. 2008. "Use of Selected Sourdough Strains of *Lactobacillus* for Removing Gluten and Enhancing the Nutritional Properties of Gluten-Free Bread." Journal of Food Protection 71 (7): 1491-95.

Doyle, J. E., W. H. Mehrhof, and R. R. Ernst. 1968. "Limitations of Thioglycolate Broth as a Sterility Test Medium for Materials Exposed to Gaseous Ethylene Oxide." *Applied Microbiology* 16 (11): 1742-44.

Eddleman, Harold. n.d. "Bacteria Media from Potato." Accessed Sep. 4, 2023. https://web.archive.org/web/20110716090823/http://www.disknet.com/indiana_bio-lab/b029.htm.

Diana, M., Rafecas, M. Quilez, J. "Free Amino Acids, Acrylamide and Biogenic Amines in Gamma-Aminobutyric Acid Enriched Sourdough and Commercial Breads." 2014. *Journal of Cereal Science* 60 (3): 639-44.

Garcia-Vaquero, Marco, and João Miguel Rocha. 2023. Sourdough Innovations: Novel Uses of Metabolites, Enzymes, and Microbiota from Sourdough Processing.

Gherna, Robert L., and C. A. Reddy. 2014. "Culture Preservation." In *Methods for General and Molecular Microbiology,* 1019-33. Washington, DC, USA: ASM Press.

Gloor, G., A. Fernandes, J. Macklaim, A. Albert, M. Links, T. Quinn, J. R. Wu, R. G. Wong, and B. Lieng. 2019. "ALDEx2 Package: Analysis of Differential Abundance Taking Sample Variation into Account." Version.

Gobbetti, M.G.M. Handbook on Sourdough Biotechnology, 1st ed.; EUA: New York, NY, USA, 2013; pp. 1-298.

Hammes, W. P., and M. G. Ganzle. 1998. "Sourdough Breads and Related Products." In *Microbiology of Fermented Foods*, edited by Brian J. B. Wood, 199-216. Boston, MA: Springer US.

Karaman, Kevser, Osman Sagdic, and M Zeki Durak. 2018. "Use of phytase active yeasts and lactic acid bacteria isolated from sourdough in the production of whole wheat bread." LWT: Food Science and Technology 91 (August 2017).

Landis, Elizabeth A., Angela M. Oliverio, Erin A. McKenney, Lauren M. Nichols, Nicole Kfoury, Megan Biango- Daniels, Leonora K. Shell, et al. 2021. "The Diversity and Function of Sourdough Starter Microbiomes." eLife 10 (January). https://doi.org/10.7554/eLife.61644.

Lin, Huang, and Shyamal Das Peddada. 2020. "Analysis of Compositions of Microbiomes with Bias Correction." *Nature Communications* 11 (1): 3514.

Lopez, H. W., A. Ouvry, E. Bervas, C. Guy, A. Messager, C. Demigne, and C. Remesy. 2000. "Strains of Lactic Acid Bacteria Isolated from Sour Doughs Degrade Phytic Acid and Improve Calcium and Magnesium Solubility from Whole Wheat Flour." Journal of Agricultural and Food Chemistry 48 (6): 2281-85.

Loponen, Jussi, and Michael G. Ganzle. 2018. "Use of Sourdough in Low FODMAP Baking." Foods (Basel, Switzerland) 7 (7). https://doi.org/10.3390/foods7070096.

Lozupone, Catherine, and Rob Knight. 2005. "UniFrac: A New Phylogenetic Method for Comparing Microbial Communities." *Applied and Environmental Microbiology* 71 (12): 8228-35.

Martino, Cameron, James T. Morton, Clarisse A. Marotz, Luke R. Thompson, Anupriya Tripathi, Rob Knight, and Karsten Zengler. 2019. "A Novel Sparse Compositional Technique Reveals Microbial Perturbations." mSystems 4 (1). https://doi.org/10.1128/mSystems.00016-19.

Martino, Cameron, Liat Shenhav, Clarisse A. Marotz, George Armstrong, Daniel McDonald, Yoshiki Vizquez-Baeza, James T. Morton, et al. 2021. "Context-Aware Dimensionality Reduction Deconvolutes Gut Microbial Community Dynamics." *Nature Biotechnology* 39 (2): 165-68.

Meng, Chen, Oana A. Zeleznik, Gerhard G. Thallinger, Bernhard Kuster, Amin M. Gholami, and Aedin C. Culhane. 2016. "Dimension Reduction Techniques for the Integrative Analysis of Multi-Omics Data." *Briefings in Bioinformatics* 17 (4): 628-41.

Montemurro, Marco, Erica Pontonio, Marco Gobbetti, and Carlo Giuseppe Rizzello. 2019. "Investigation of the Nutritional, Functional and Technological Effects of the Sourdough Fermentation of Sprouted Flours." International Journal of Food Microbiology 302 (August): 47-58.

Novotni, Dubravka, Michael Gänzle, and João Miguel Rocha. 2021. "Chapter 5—Composition and Activity of Microbiota in Sourdough and Their Effect on Bread Quality and Safety." In *Trends in Wheat and Bread Making*, edited by Charis M. Galanakis, 129-72. Academic Press.

Rahman, Gibraan, James T. Morton, Cameron Martino, Gregory D. Sepich-Poore, Celeste Allaband, Caitlin Guccione, Yang Chen, Daniel Hakim, Mehrbod Estaki, and Rob Knight. 2023. "BIRDMAn: A Bayesian Differential Abundance Framework That Enables Robust Inference of Host-Microbe Associations." *bioRxiv: The Preprint Server for Biology*, February. https://doi.org/10.1101/2023.01.30.526328.

Rizzello, Carlo G., Maria De Angelis, Raffaella Di Cagno, Alessandra Camarca, Marco Silano, Ilario Losito, Massimo De Vincenzi, et al. 2007. "Highly Efficient Gluten Degradation by Lactobacilli and Fungal Proteases during Food Processing: New Perspectives for Celiac Disease." Applied and Environmental Microbiology 73 (14): 4499-4507.

Rizzello, Carlo Giuseppe, Jose Antonio Curiel, Luana Nionelli, Olimpia Vincentini, Raffaella Di Cagno, Marco Silano, Marco Gobbetti, and Rossana Coda. 2014. "Use of Fungal Proteases and Selected Sourdough Lactic Acid Bacteria for Making Wheat Bread with an Intermediate Content of Gluten." Food Microbiology 37 (February): 59-68.

Rizzello, Carlo Giuseppe, Piero Portincasa, Marco Montemurro, Domenica Maria Di Palo, Michele Pio Lorusso, Maria De Angelis, Leonilde Bonfrate, Bernard Genot, and Marco Gobbetti. 2019. "Sourdough Fermented Breads Are More Digestible than Those Started with Baker's Yeast Alone: An In Vivo Challenge Dissecting Distinct Gastrointestinal Responses." Nutrients 11 (12). https://doi.org/10.3390/nu11122954.

Rodriguez-Ramiro, I., C. A. Brearley, S. F. A. Bruggraber, A. Perfecto, P. Shewry, and S. Fairweather-Tait. 2017. "Assessment of iron bioavailability from different bread making processes using an in vitro intestinal cell model." Food Chemistry 228: 91-98.

Rohart, Florian, Benôit Gautier, Amrit Singh, and Kim-Anh Lê Cao. 2017. "mixOmics: An R Package for 'Omics Feature Selection and Multiple Data Integration." *PLoS Computational Biology* 13 (11): e1005752.

Ronald M. Atlas. 2004. *Handbook of Microbiological Media, Third Edition*. Taylor & Francis.

Tucker, Caroline M., Marc W. Cadotte, Silvia B. Carvalho, T. Jonathan Davies, Simon Ferrier, Susanne A. Fritz, Rich Grenyer, et al. 2017. "A Guide to Phylogenetic Metrics for Conservation, Community Ecology and Macroecology." *Biological Reviews of the Cambridge Philosophical Society* 92 (2): 698-715.

Siepmann, F. B.; Ripari, V.; Waszczynskyj, N.; Spier, M. R. Overview of Sourdough Technology: From Production to Marketing. Food Bioprocess Technol. 2018, 11

Timmermans, Evelyne, Ine Langie, An Bautil, Kristof Brijs, Carolien Buvé, Ann Van Loey, Ilse Scheirlinck, Roel Van der Meulen, and Christophe M. Courtin. 2023. "Study of the Fermentation Characteristics of Non-Conventional Yeast Strains in Sweet Dough." Foods (Basel, Switzerland) 12 (4). https://doi.org/10.3390/foods12040830.

Vermeulen, N., M. G. Gänzle, and R. F. Vogel. 2007. "Glutamine Deamidation by Cereal-associated Lactic Acid Bacteria." Journal of Applied Microbiology 103 (4): 1197-1205.

Weiss, W., C. Vogelmeier, and A. Görg. 1993. "Electrophoretic Characterization of Wheat Grain Allergens from Different Cultivars Involved in Bakers' Asthma." *Electrophoresis* 14 (8): 805-16.

"YPD Media." 2010. *Cold Spring Harbor Protocols* 2010 (9): db.rec12315.

Zotta, Teresa, Paolo Piraino, Annamaria Ricciardi, Paul L. H. McSweeney, and Eugenio Parente. 2006. "Proteolysis in Model Sourdough Fermentations." *Journal of Agricultural and Food Chemistry* 54 (7): 2567-74.

What is claimed is:

1. A composition comprising:

(a) a purified population of microorganisms comprising:

(i) a yeast with an ITS nucleic acid sequence sharing at least 99% sequence identity to SEQ ID NO: 207;

(ii) a bacterium with a 16S nucleic acid sequence sharing at least 99% sequence identity to SEQ ID NO: 4; and/or (iii) a bacterium with a 16S nucleic acid sequence sharing at least 99% sequence identity to SEQ ID NO: 8; and (b) a food-grade carrier or excipient; and wherein the purified population of microorganisms is lyophilized.

2. The composition of claim 1, wherein the purified population of microorganisms comprises a yeast with an ITS nucleic acid sequence comprising SEQ ID NO: 207.

3. The composition of claim 1, wherein the purified population of microorganisms comprises a bacterium with a 16S nucleic acid sequence comprising SEQ ID NO: 4.

4. The composition of claim 1, wherein the purified population of microorganisms comprises a bacterium with a 16S nucleic acid sequence comprising SEQ ID NO: 8.

5. The composition of claim 1, wherein the purified population of microorganisms comprises a *Saccharomyces cerevisiae* as deposited as PTA-127804.

6. The composition of claim 1, wherein the purified population of microorganisms comprises a *Fructilactobacillus sanfranciscensis* as deposited as PTA-127806.

7. The composition of claim 1, wherein the purified population of microorganisms comprises a *Levilactobacillus brevis* as deposited as PTA-127808.

8. The composition of claim 1, wherein the purified population of microorganisms comprises:

(a) a yeast with an ITS nucleic acid sequence sharing at least 99% sequence identity to SEQ ID NO: 207;

(b) a bacterium with a 16S nucleic acid sequence sharing at least 99% sequence identity to SEQ ID NO: 4; and (c) a bacterium with a 16S nucleic acid sequence sharing at least 99% sequence identity to SEQ ID NO: 8.

9. The composition of claim 1, wherein the purified population of microorganisms comprises:

(a) a yeast with an ITS nucleic acid sequence comprising SEQ ID NO: 207;

(b) a bacterium with a 16S nucleic acid sequence comprising SEQ ID NO: 4; and/or (c) a bacterium with a 16S nucleic acid sequence comprising SEQ ID NO: 8.

10. The composition of claim 1, wherein the purified population of microorganisms comprises:

(a) a yeast with an ITS nucleic acid sequence comprising SEQ ID NO: 207;

(b) a bacterium with a 16S nucleic acid sequence comprising SEQ ID NO: 4; and (c) a bacterium with a 16S nucleic acid sequence comprising SEQ ID NO: 8.

11. The composition of claim 1, wherein the purified population of microorganisms comprises:

(a) a *Saccharomyces cerevisiae* as deposited as PTA-127804;

(b) a *Fructilactobacillus sanfranciscensis* as deposited as PTA-127806; and/or (c) a *Levilactobacillus brevis* as deposited as PTA-127808.

12. The composition of claim 1, wherein the purified population of microorganisms comprises:

(a) a *Saccharomyces cerevisiae* as deposited as PTA-127804;

(b) a *Fructilactobacillus sanfranciscensis* as deposited as PTA-127806; and (c) a *Levilactobacillus brevis* as deposited as PTA-127808.

13. The composition of claim 1, wherein each of the microorganisms is present in the composition at about $10^2$ CFU/g or more.

14. The composition of claim 1, wherein each of the microorganisms is present in the composition at about $10^9$ CFU/g, about $10^{10}$ CFU/g, about $10^{11}$ CFU/g, about $10^{12}$ CFU/g, about $10^{13}$ CFU/g, or about $10^{14}$ CFU/g.

15. The composition of claim 1, wherein the composition comprises one or more preservatives, flavoring agents, or leavening agents.

16. The composition of claim 1, wherein the composition comprises maltose, trehalose, sucrose, maltodextrin, ascorbic acid, or a combination thereof.

17. The composition of claim 1, wherein the composition is formulated as a dry powder, food ingredient, food preparation, food supplement, water additive, moisture-stabilized additive, consumable, solid, gel, liquid, or dough.

18. The composition of claim 1, wherein the composition is a starter culture for baked good production, a baked good, or a dough.

19. The composition of claim 1, wherein the composition is a further comprises a bacterium with a 16S nucleic acid sequence sharing at least 99% sequence identity to SEQ ID NO: 269.

20. The composition of claim 1, wherein the composition further comprises a *Kazachstania humilis* as deposited as PTA-127805.

21. A method for improving fermentation of a food product, the method comprising admixing an effective amount of the composition of claim 1 to the food product.

22. A method of producing a dough, the method comprising admixing an effective amount of the composition of claim 1 to the dough.

23. A method of increasing leavening ability of a dough, the method comprising admixing an effective amount of the composition of claim 1 to the dough.

24. A method of lowering pH of a dough, the method comprising admixing an effective amount of the composition of claim 1 to the dough.

25. A method of increasing shelf-life of a dough or baked good, the method comprising admixing an effective amount of the composition of claim 1 to the dough or baked good.

26. A method of enhancing rheological properties of a dough or baked good, the method comprising admixing an effective amount of the composition of claim 1 to the dough or baked good.

27. A method of increasing flavor or aroma of a dough or baked good, the method comprising admixing an effective amount of the composition of claim 1 to the dough or baked good.

28. A method of increasing nutritional quality of a dough or baked good, the method comprising admixing an effective amount of the composition of claim 1 to the dough or baked good.

29. A method of increasing degradation of:

(a) complex and/or simple carbohydrates in a dough;

(b) chemical compounds or chemical precursors in a dough; or (c) proteins in a dough;

the method comprising admixing an effective amount of the composition of claim 1 to the dough.

30. A method of increasing production of organic acids, peptides, and/or proteins in a dough, the method comprising admixing an effective amount of the composition of claim 1 to the dough.

* * * * *

SEQUENCE LISTING

```
Sequence total quantity: 272
SEQ ID NO: 1            moltype = DNA  length = 100
FEATURE                 Location/Qualifiers
source                  1..100
```

```
                         mol_type = genomic DNA
                         organism = Latilactobacillus sakei
SEQUENCE: 1
gtgtcagcag ccgcggtaat acgtaggtgg caagcgttgt ccggatttat tgggcgtaaa  60
gcgagcgcag gcggtttctt aagtctgatg tgaaagcctt                       100

SEQ ID NO: 2             moltype = DNA  length = 100
FEATURE                  Location/Qualifiers
source                   1..100
                         mol_type = genomic DNA
                         organism = Leuconostoc mesenteroides
SEQUENCE: 2
gtgtcagcag ccgcggtaat acgtatgtcc cgagcgttat ccggatttat tgggcgtaaa  60
gcgagcgcag acggtttatt aagtctgatg tgaaagcccg                       100

SEQ ID NO: 3             moltype = DNA  length = 100
FEATURE                  Location/Qualifiers
source                   1..100
                         mol_type = genomic DNA
                         organism = Latilactobacillus curvatus
SEQUENCE: 3
gtgtcagccg ccgcggtaat acgtaggtgg caagcgttgt ccggatttat tgggcgtaaa  60
gcgagcgcag gcggtttctt aagtctgatg tgaaagcctt                       100

SEQ ID NO: 4             moltype = DNA  length = 100
FEATURE                  Location/Qualifiers
source                   1..100
                         mol_type = genomic DNA
                         organism = Lactobacillus sanfranciscensis
SEQUENCE: 4
tacgtaggtg gcaaacgttg tccggattta ttgggcgtaa agggagcgca ggcggtttat  60
taagtctgat gtgaaagcct tcggcttaac cggagaagtg                       100

SEQ ID NO: 5             moltype = DNA  length = 100
FEATURE                  Location/Qualifiers
source                   1..100
                         mol_type = genomic DNA
                         organism = Pediococcus inopinatus
SEQUENCE: 5
tacgtaggtg gcaagcgtta tccggattta ttgggcgtaa agcgagcgca ggcggtttct  60
taagtctaat gtgaaagcct tcggcttaac cgaagaagtg                       100

SEQ ID NO: 6             moltype = DNA  length = 100
FEATURE                  Location/Qualifiers
source                   1..100
                         mol_type = genomic DNA
                         organism = Lactobacillus paralimentarius
SEQUENCE: 6
tacgtaggtg gcaagcgttg tccggattta ttgggcgtaa agagaatgta ggcggtttat  60
taagtttgaa gtgaaagccc tcggctcaac cgaggaagtg                       100

SEQ ID NO: 7             moltype = DNA  length = 100
FEATURE                  Location/Qualifiers
source                   1..100
                         mol_type = genomic DNA
                         organism = Lactobacillus sakei
SEQUENCE: 7
tacgtaggtg gcaagcgttg tccggattta ttgggcgtaa agcgagcgca ggcggtttct  60
taagtctgat gtgaaagcct tcggctcaac cgaagaagtg                       100

SEQ ID NO: 8             moltype = DNA  length = 100
FEATURE                  Location/Qualifiers
source                   1..100
                         mol_type = genomic DNA
                         organism = Lactobacillus brevis
SEQUENCE: 8
tacgtaggtg gcaagcgttg tccggattta ttgggcgtaa agcgagcgca ggcggttttt  60
taagtctgat gtgaaagcct tcggcttaac cggagaagtg                       100

SEQ ID NO: 9             moltype = DNA  length = 100
FEATURE                  Location/Qualifiers
source                   1..100
                         mol_type = genomic DNA
                         organism = Lactobacillus plantarum
SEQUENCE: 9
tacgtaggtg gcaagcgttg tccggattta ttgggcgtaa agcgagcgca ggcggttttt  60
taagtctgat gtgaaagcct tcggctcaac cgaagaagtg                       100

SEQ ID NO: 10            moltype = DNA  length = 100
```

```
FEATURE                Location/Qualifiers
source                 1..100
                       mol_type = genomic DNA
                       organism = Pediococcus pentosaceus
SEQUENCE: 10
tacgtaggtg gcaagcgtta tccggattta ttgggcgtaa agcgagcgca ggcggtcttt  60
taagtctaat gtgaaagcct tcggctcaac cgaagaagtg                        100

SEQ ID NO: 11          moltype = DNA  length = 100
FEATURE                Location/Qualifiers
source                 1..100
                       mol_type = genomic DNA
                       organism = Lactobacillus brevis
SEQUENCE: 11
tacgtaggtg gcaagcgttg tccggattta ttgggcgtaa agcgagcgca ggcggtttct  60
taagtctgat gtgaaagcct tcggcttaac cggagaagtg                        100

SEQ ID NO: 12          moltype = DNA  length = 100
FEATURE                Location/Qualifiers
source                 1..100
                       mol_type = genomic DNA
                       organism = Pediococcus parvulus
SEQUENCE: 12
tacgtaggtg gcaagcgtta tccggattta ttgggcgtaa agcgagcgca ggcggtcttt  60
taagtctaat gtgaaagcct tcggcttaac cgaagaagtg                        100

SEQ ID NO: 13          moltype = DNA  length = 100
FEATURE                Location/Qualifiers
source                 1..100
                       mol_type = genomic DNA
                       organism = Acetobacter tropicalis
SEQUENCE: 13
tacgaagggg gctagcgttg ctcggaatga ctgggcgtaa agggcgtgta ggcggtttgt  60
acagtcagat gtgaaatccc cgggcttaac ctgggagctg                        100

SEQ ID NO: 14          moltype = DNA  length = 100
FEATURE                Location/Qualifiers
source                 1..100
                       mol_type = genomic DNA
                       organism = Acetobacter orleanensis
SEQUENCE: 14
tacgaagggg gctagcgttg ctcggaatga ctgggcgtaa agggcgtgta ggcggtttgt  60
acagttagat gtgaaatccc cgggcttaac ctgggagctg                        100

SEQ ID NO: 15          moltype = DNA  length = 100
FEATURE                Location/Qualifiers
source                 1..100
                       mol_type = genomic DNA
                       organism = Lactobacillus hilgardii
SEQUENCE: 15
tacgtaggtg gcaagcgttg tccggattta ttgggcgtaa agcgagcgca ggcggttttt  60
taggtctgat gtgaaagcct tcggcttaac cggagaagtg                        100

SEQ ID NO: 16          moltype = DNA  length = 100
FEATURE                Location/Qualifiers
source                 1..100
                       mol_type = genomic DNA
                       organism = Lactobacillus parabuchneri
SEQUENCE: 16
tacgtaggtg gcaagcgttg tccggattta ttgggcgtaa agcgagcgca ggcggtttct  60
taggtctgat gtgaaagcct tcggcttaac cggagaagtg                        100

SEQ ID NO: 17          moltype = DNA  length = 100
FEATURE                Location/Qualifiers
source                 1..100
                       mol_type = genomic DNA
                       organism = Lactobacillus sanfranciscensis
SEQUENCE: 17
gtgtcagcag ccgcggtaat acgtaggtgg caaacgttgt ccggatttat tgggcgtaaa  60
gggagcgcag gcggtttatt aagtctgatg tgaaagcctt                        100

SEQ ID NO: 18          moltype = DNA  length = 100
FEATURE                Location/Qualifiers
source                 1..100
                       mol_type = genomic DNA
                       organism = Lactobacillus coryniformis
SEQUENCE: 18
tacgtaggtg gcaagcgttg tccggattta ttgggcgtaa agcgagcgca ggcggttttt  60
taagtctgat gtgaaagcct tcggcttaac cgaagaagtg                        100
```

```
SEQ ID NO: 19          moltype = DNA  length = 100
FEATURE                Location/Qualifiers
source                 1..100
                       mol_type = genomic DNA
                       organism = Leuconostoc mesenteroides
SEQUENCE: 19
tacgtatgtc ccgagcgtta tccggattta ttgggcgtaa agcgagcgca gacggtttat  60
taagtctgat gtgaaagccc ggagctcaac tccggaatgg                        100

SEQ ID NO: 20          moltype = DNA  length = 100
FEATURE                Location/Qualifiers
source                 1..100
                       mol_type = genomic DNA
                       organism = Lactobacillus casei
SEQUENCE: 20
tacgtaggtg gcaagcgtta tccggattta ttgggcgtaa agcgagcgca ggcggttttt  60
taagtctgat gtgaaagccc tcggcttaac cgaggaagcg                        100

SEQ ID NO: 21          moltype = DNA  length = 100
FEATURE                Location/Qualifiers
source                 1..100
                       mol_type = genomic DNA
                       organism = Lactobacillus sanfranciscensis
SEQUENCE: 21
gtgtcagccg ccgcggtaat acgtaggtgg caaacgttgt ccggatttat tgggcgtaaa  60
gggagcgcag gcggtttatt aagtctgatg tgaaagcctt                        100

SEQ ID NO: 22          moltype = DNA  length = 100
FEATURE                Location/Qualifiers
source                 1..100
                       mol_type = genomic DNA
                       organism = Lactobacillus brevis
SEQUENCE: 22
tacgtaggtg gcaagcgttg tccggattta ttgggcgtaa agcgagcgca ggcggttatt  60
taagtctgat gtgaaagcct tcggcttaac cgaagaagtg                        100

SEQ ID NO: 23          moltype = DNA  length = 100
FEATURE                Location/Qualifiers
source                 1..100
                       mol_type = genomic DNA
                       organism = Leuconostoc gelidum
SEQUENCE: 23
tacgtatgtc ccgagcgtta tccggattta ttgggcgtaa agcgagcgca gacggttgat  60
taagtctgat gtgaaagccc ggagctcaac tccggaatgg                        100

SEQ ID NO: 24          moltype = DNA  length = 100
FEATURE                Location/Qualifiers
source                 1..100
                       mol_type = genomic DNA
                       organism = Lactococcus sp.
SEQUENCE: 24
tacgtaggtc ccgagcgttg tccggattta ttgggcgtaa agcgagcgca ggtggtttat  60
taagtctggt gtaaaaggca gtggctcaac cattgtatgc                        100

SEQ ID NO: 25          moltype = DNA  length = 100
FEATURE                Location/Qualifiers
source                 1..100
                       mol_type = genomic DNA
                       organism = Paracoccus laeviglucosivorans
SEQUENCE: 25
tacggagggg gctagcgttg ttcggaatta ctgggcgtaa agcgcacgta ggcggaccgg  60
aaagtcagag gtgaaatccc agggctcaac cttggaactg                        100

SEQ ID NO: 26          moltype = DNA  length = 100
FEATURE                Location/Qualifiers
source                 1..100
                       mol_type = genomic DNA
                       organism = Acetobacter lovaniensis
SEQUENCE: 26
tacgaagggg gctagcgttg ctcggaatga ctgggcgtaa agggcgtgta ggcggtttac  60
acagtcagat gtgaaatccc cgggcttaac ctgggagctg                        100

SEQ ID NO: 27          moltype = DNA  length = 100
FEATURE                Location/Qualifiers
source                 1..100
                       mol_type = genomic DNA
                       organism = Lactobacillus sanfranciscensis
SEQUENCE: 27
```

```
gtgccagcag ccgcggtaat acgtaggtgg caaacgttgt ccggatttat tgggcgtaaa  60
gggagcgcag gcggtttatt aagtctgatg tgaaagcctt                        100

SEQ ID NO: 28          moltype = DNA  length = 100
FEATURE                Location/Qualifiers
source                 1..100
                       mol_type = genomic DNA
                       organism = Leuconostoc gelidum
SEQUENCE: 28
gtgtcagcag ccgcggtaat acgtatgtcc cgagcgttat ccggatttat tgggcgtaaa  60
gcgagcgcag acggttgatt aagtctgatg tgaaagcccg                        100

SEQ ID NO: 29          moltype = DNA  length = 100
FEATURE                Location/Qualifiers
source                 1..100
                       mol_type = genomic DNA
                       organism = Lactobacillus sakei
SEQUENCE: 29
gtgccagcag ccgcggtaat acgtaggtgg caagcgttgt ccggatttat tgggcgtaaa  60
gcgagcgcag gcggtttctt aagtctgatg tgaaagcctt                        100

SEQ ID NO: 30          moltype = DNA  length = 100
FEATURE                Location/Qualifiers
source                 1..100
                       mol_type = genomic DNA
                       organism = Leuconostoc gelidum
SEQUENCE: 30
gtgtcagccg ccgcggtaat acgtatgtcc cgagcgttat ccggatttat tgggcgtaaa  60
gcgagcgcag acggttgatt aagtctgatg tgaaagcccg                        100

SEQ ID NO: 31          moltype = DNA  length = 100
FEATURE                Location/Qualifiers
source                 1..100
                       mol_type = genomic DNA
                       organism = Leuconostoc gelidum
SEQUENCE: 31
tacgtatgtc ccgagcgtta tccggattta ttgggcgtaa agcgagcgca gacggttgtt  60
taagtctgat gtgaaagccc ggagctcaac tccggaaagg                        100

SEQ ID NO: 32          moltype = DNA  length = 100
FEATURE                Location/Qualifiers
source                 1..100
                       mol_type = genomic DNA
                       organism = Lactobacillus sakei
SEQUENCE: 32
tacgtaggtg gcaagcgtta tccggaatta ttgggcgtaa agcgcgcgta ggcggttttt  60
taagtctgat gtgaaagccc acggctcaac cgtggagggt                        100

SEQ ID NO: 33          moltype = DNA  length = 100
FEATURE                Location/Qualifiers
source                 1..100
                       mol_type = genomic DNA
                       organism = Lactobacillus sakei
SEQUENCE: 33
tacgtaggtc ccgagcgttg tccggattta ttgggcgtaa agcgagcgca ggcggtttga  60
taagtctgaa gttaaaggct gtggctcaac catagttcgc                        100

SEQ ID NO: 34          moltype = DNA  length = 100
FEATURE                Location/Qualifiers
source                 1..100
                       mol_type = genomic DNA
                       organism = Lactobacillus perolens
SEQUENCE: 34
tacgtaggtg gcaagcgttg tccggattta ttgggcgtaa agcgagtgca ggcggtcttt  60
taagtctgat gtgaaagcct tcggcttaac cgaagaaggg                        100

SEQ ID NO: 35          moltype = DNA  length = 100
FEATURE                Location/Qualifiers
source                 1..100
                       mol_type = genomic DNA
                       organism = Lactobacillus sakei
SEQUENCE: 35
tacgtaggtc ccgagcgttg tccggattta ttgggcgtaa agcgagcgca ggcggttaga  60
taagtctgaa gttaaaggct gtggcttaac catagtacgc                        100

SEQ ID NO: 36          moltype = DNA  length = 100
FEATURE                Location/Qualifiers
source                 1..100
                       mol_type = genomic DNA
```

```
                          organism = Secundilactobacillus sp.
SEQUENCE: 36
tacgtaggtg gcaagcgtta tccggattta ttgggcgtaa agagagtgca ggcggtttgt  60
taagtctgat gtgaaagcct tcggctcaac cgaagaagtg                        100

SEQ ID NO: 37             moltype = DNA  length = 100
FEATURE                   Location/Qualifiers
source                    1..100
                          mol_type = genomic DNA
                          organism = Lactobacillus sanfranciscensis
SEQUENCE: 37
gtgccagccg ccgcggtaat acgtaggtgg caaacgttgt ccggatttat tgggcgtaaa  60
gggagcgcag gcggtttatt aagtctgatg tgaaagcctt                        100

SEQ ID NO: 38             moltype = DNA  length = 100
FEATURE                   Location/Qualifiers
source                    1..100
                          mol_type = genomic DNA
                          organism = Gluconobacter thailandicus
SEQUENCE: 38
tacgaagggg gctagcgttg ctcggaatga ctgggcgtaa agggcgcgta ggcggttgat  60
gcagtcagat gtgaaatccc cgggcttaac ctgggaactg                        100

SEQ ID NO: 39             moltype = DNA  length = 100
FEATURE                   Location/Qualifiers
source                    1..100
                          mol_type = genomic DNA
                          organism = Leuconostoc mesenteroides
SEQUENCE: 39
gtgtcagccg ccgcggtaat acgtatgtcc cgagcgttat ccggatttat tgggcgtaaa  60
gcgagcgcag acggtttatt aagtctgatg tgaaagcccg                        100

SEQ ID NO: 40             moltype = DNA  length = 100
FEATURE                   Location/Qualifiers
source                    1..100
                          mol_type = genomic DNA
                          organism = Lactobacillus rossiae
SEQUENCE: 40
tacgtaggtg gcaagcgtta tccggattta ttgggcgtaa agggagtgca ggcggttatt  60
taagtctgat gtgaaagcct tcggcttaac cggagaaggg                        100

SEQ ID NO: 41             moltype = DNA  length = 100
FEATURE                   Location/Qualifiers
source                    1..100
                          mol_type = genomic DNA
                          organism = Levilactobacillus brevis
SEQUENCE: 41
gtgtcagcag ccgcggtaat acgtaggtgg caagcgttgt ccggatttat tgggcgtaaa  60
gcgagcgcag gcggtttttt aagtctgatg tgaaagcctt                        100

SEQ ID NO: 42             moltype = DNA  length = 100
FEATURE                   Location/Qualifiers
source                    1..100
                          mol_type = genomic DNA
                          organism = Gluconobacter roseus
SEQUENCE: 42
tacgaagggg gctagcgttg ctcggaatga ctgggcgtaa agggcgcgta ggcggttgtt  60
acagtcagat gtgaaatccc cgggcttaac ctgggaactg                        100

SEQ ID NO: 43             moltype = DNA  length = 100
FEATURE                   Location/Qualifiers
source                    1..100
                          mol_type = genomic DNA
                          organism = Leucobacter albus
SEQUENCE: 43
tacgtagggt gcaagcgttg tccggaatta ttgggcgtaa agagctcgta ggcggcttgt  60
cgcgtctgct gtgaaatccc ggggctcaac cccgggcctg                        100

SEQ ID NO: 44             moltype = DNA  length = 100
FEATURE                   Location/Qualifiers
source                    1..100
                          mol_type = genomic DNA
                          organism = Acetobacter persici
SEQUENCE: 44
tacgaagggg gctagcgttg ctcggaatga ctgggcgtaa agggcgtgta ggcggtttgc  60
acagttagat gtgaaatccc cgggcttaac ctgggagctg                        100

SEQ ID NO: 45             moltype = DNA  length = 100
FEATURE                   Location/Qualifiers
```

```
source                 1..100
                       mol_type = genomic DNA
                       organism = Lactobacillus sakei
SEQUENCE: 45
gtgccagccg ccgcggtaat acgtaggtgg caagcgttgt ccggatttat tgggcgtaaa  60
gcgagcgcag gcggtttctt aagtctgatg tgaaagcctt                        100

SEQ ID NO: 46          moltype = DNA  length = 100
FEATURE                Location/Qualifiers
source                 1..100
                       mol_type = genomic DNA
                       organism = Lactobacillus plantarum
SEQUENCE: 46
gtgtcagccg ccgcggtaat acgtaggtgg caagcgttgt ccggatttat tgggcgtaaa  60
gcgagcgcag gcggtttttt aagtctgatg tgaaagcctt                        100

SEQ ID NO: 47          moltype = DNA  length = 100
FEATURE                Location/Qualifiers
source                 1..100
                       mol_type = genomic DNA
                       organism = Leuconostoc gelidum
SEQUENCE: 47
gtgccagcag ccgcggtaat acgtatgtcc cgagcgttat ccggatttat tgggcgtaaa  60
gcgagcgcag acggttgatt aagtctgatg tgaaagcccg                        100

SEQ ID NO: 48          moltype = DNA  length = 100
FEATURE                Location/Qualifiers
source                 1..100
                       mol_type = genomic DNA
                       organism = Paracoccus aminophilus
SEQUENCE: 48
tacggagggg gctagcgttg ttcggaatta ctgggcgtaa agcgcacgta ggcggactgg  60
aaagttggag gtgaaatccc agggctcaac cttggaactg                        100

SEQ ID NO: 49          moltype = DNA  length = 100
FEATURE                Location/Qualifiers
source                 1..100
                       mol_type = genomic DNA
                       organism = Lactobacillus fermentum
SEQUENCE: 49
tacgtaggtg gcaagcgtta tccggattta ttgggcgtaa agagagtgca ggcggttttc  60
taagtctgat gtgaaagcct tcggcttaac cggagaagtg                        100

SEQ ID NO: 50          moltype = DNA  length = 100
FEATURE                Location/Qualifiers
source                 1..100
                       mol_type = genomic DNA
                       organism = Leuconostoc gelidum
SEQUENCE: 50
gtgccagccg ccgcggtaat acgtatgtcc cgagcgttat ccggatttat tgggcgtaaa  60
gcgagcgcag acggttgatt aagtctgatg tgaaagcccg                        100

SEQ ID NO: 51          moltype = DNA  length = 100
FEATURE                Location/Qualifiers
source                 1..100
                       mol_type = genomic DNA
                       organism = Lactobacillus sanfranciscensis
SEQUENCE: 51
tacgtaggtg gcaaacgttg tccggattta ttgggcgtaa agggagcgcg ggcggtttat  60
taagtctgat gtgaaagtct tcggcttaac cggagaagtg                        100

SEQ ID NO: 52          moltype = DNA  length = 100
FEATURE                Location/Qualifiers
source                 1..100
                       mol_type = genomic DNA
                       organism = Lactobacillus sp.
SEQUENCE: 52
tacgtaggtg gcaagcgttg tccggattta ttgggcgtaa agagaatgta ggcggtttat  60
taagtttgaa gtgaaaaccc tcggctcaac cgaggaagtg                        100

SEQ ID NO: 53          moltype = DNA  length = 100
FEATURE                Location/Qualifiers
source                 1..100
                       mol_type = genomic DNA
                       organism = Psychrobacter fulvigenes
SEQUENCE: 53
tacagagggt gcaagcgtta atcggaatta ctgggcgtaa agcgagcgta ggtggcttga  60
taagtcagat gtgaaatccc cgggcttaac ctgggaactg                        100
```

```
SEQ ID NO: 54          moltype = DNA  length = 100
FEATURE                Location/Qualifiers
source                 1..100
                       mol_type = genomic DNA
                       organism = Weissella confusa
SEQUENCE: 54
tacgtatgtt ccaagcgtta tccggattta ttgggcgtaa agcgagcgca gacggttatt  60
taagtctgaa gtgaaagccc tcagctcaac tgaggaattg                        100

SEQ ID NO: 55          moltype = DNA  length = 100
FEATURE                Location/Qualifiers
source                 1..100
                       mol_type = genomic DNA
                       organism = Lactobacillus sakei
SEQUENCE: 55
tacgtaggtg gcaagcgtta tccggaatta ttgggcgtaa agcgcgcgta ggcggtttct  60
taagtctgat gtgaaagccc acggctcaac cgtggagggt                        100

SEQ ID NO: 56          moltype = DNA  length = 100
FEATURE                Location/Qualifiers
source                 1..100
                       mol_type = genomic DNA
                       organism = Lactobacillus sanfranciscensis
SEQUENCE: 56
tacgtaggtg gcaaacgttg tccgggttta ttgggcgtaa agggagcgca ggcggtttat  60
taagtctgat gtgaaagcct tcggcttaac cggagaagtg                        100

SEQ ID NO: 57          moltype = DNA  length = 100
FEATURE                Location/Qualifiers
source                 1..100
                       mol_type = genomic DNA
                       organism = Fenollaria massiliensis
SEQUENCE: 57
tacgtaaggg gcgagcgttg tccggaatta ttgggcgtaa agagtgcgta ggcggcaaat  60
taagtcagat gtgaaaacta agggctcaac ccatagattg                        100

SEQ ID NO: 58          moltype = DNA  length = 100
FEATURE                Location/Qualifiers
source                 1..100
                       mol_type = genomic DNA
                       organism = Lactobacillus brevis
SEQUENCE: 58
tacgtaggtg gcaagcgttg tccggattta ttgggcgtaa agcgagcgcg ggcggttttt  60
taagtctgat gtgaaagcct tcggcttaac cggagaagtg                        100

SEQ ID NO: 59          moltype = DNA  length = 100
FEATURE                Location/Qualifiers
source                 1..100
                       mol_type = genomic DNA
                       organism = Peptoniphilus sp.
SEQUENCE: 59
tacgtagggg gctagcgttg tccggaatca ctgggcgtaa agggttcgca ggcggaaatg  60
caagtcaggt gtaaaaggca gtagcttaac tactgtaagc                        100

SEQ ID NO: 60          moltype = DNA  length = 100
FEATURE                Location/Qualifiers
source                 1..100
                       mol_type = genomic DNA
                       organism = Lactobacillus brevis
SEQUENCE: 60
gtgccagcag ccgcggtaat acgtaggtgg caagcgttgt ccggatttat tgggcgtaaa  60
gcgagcgcag gcggtttttt aagtctgatg tgaaagcctt                        100

SEQ ID NO: 61          moltype = DNA  length = 100
FEATURE                Location/Qualifiers
source                 1..100
                       mol_type = genomic DNA
                       organism = Corynebacterium tuberculostearicum
SEQUENCE: 61
tacgtagggt gcgagcgttg tccggaatta ctgggcgtaa agggctcgta ggtggtttgt  60
cgcgtcgtct gtgaaattcc ggggcttaac tccgggcgtg                        100

SEQ ID NO: 62          moltype = DNA  length = 100
FEATURE                Location/Qualifiers
source                 1..100
                       mol_type = genomic DNA
                       organism = Lactobacillus sakei
SEQUENCE: 62
tacgtaggtg gcaagcgttg tccggaatta ttgggcgtaa agcgcgcgca ggcggtcctt  60
```

-continued

```
taagtctgat gtgaaagccc acggctcaac cgtggagggt                      100

SEQ ID NO: 63          moltype = DNA  length = 100
FEATURE                Location/Qualifiers
source                 1..100
                       mol_type = genomic DNA
                       organism = Lactobacillus acetotolerans
SEQUENCE: 63
tacgtaggtg gcaagcgttg tccggattta ttgggcgtaa agcgagcgca ggcggaaaga  60
taagtcagat gtgaaagccc tcggcttaac cgaggaatag                      100

SEQ ID NO: 64          moltype = DNA  length = 100
FEATURE                Location/Qualifiers
source                 1..100
                       mol_type = genomic DNA
                       organism = Lactobacillus brevis
SEQUENCE: 64
tacgtaggtg gcaagcgttg tccggattta ttgggcgtaa agcgagcgca ggcggttttt  60
taagtctgat gtgaaatcct tcggcttaac cggagaagtg                      100

SEQ ID NO: 65          moltype = DNA  length = 100
FEATURE                Location/Qualifiers
source                 1..100
                       mol_type = genomic DNA
                       organism = Leuconostoc mesenteroides
SEQUENCE: 65
gtgccagcag ccgcggtaat acgtatgtcc cgagcgttat ccggatttat tgggcgtaaa  60
gcgagcgcag acggtttatt aagtctgatg tgaaagcccg                      100

SEQ ID NO: 66          moltype = DNA  length = 100
FEATURE                Location/Qualifiers
source                 1..100
                       mol_type = genomic DNA
                       organism = Ezakiella coagulans
SEQUENCE: 66
tacgtatgga gcgagcgttg tccggaatta ttgggcgtaa agggtgcgca ggcggcttta  60
caagttggat gtgaaatatt gtggctcaac cacaaacgtg                      100

SEQ ID NO: 67          moltype = DNA  length = 100
FEATURE                Location/Qualifiers
source                 1..100
                       mol_type = genomic DNA
                       organism = Leuconostoc mesenteroides
SEQUENCE: 67
gtgccagccg ccgcggtaat acgtatgtcc cgagcgttat ccggatttat tgggcgtaaa  60
gcgagcgcag acggtttatt aagtctgatg tgaaagcccg                      100

SEQ ID NO: 68          moltype = DNA  length = 100
FEATURE                Location/Qualifiers
source                 1..100
                       mol_type = genomic DNA
                       organism = Lactobacillus brevis
SEQUENCE: 68
gtgccagccg ccgcggtaat acgtaggtgg caagcgttgt ccggatttat tgggcgtaaa  60
gcgagcgcag gcggtttttt aagtctgatg tgaaagcctt                      100

SEQ ID NO: 69          moltype = DNA  length = 100
FEATURE                Location/Qualifiers
source                 1..100
                       mol_type = genomic DNA
                       organism = Pediococcus parvulus
SEQUENCE: 69
tacgtaggtg gcaagcgtta tccggattta ttgggcgtaa agcgagcgca ggcggccttt  60
taagtctaat gtgaaagcct tcggcttaac cgaagaagtg                      100

SEQ ID NO: 70          moltype = DNA  length = 100
FEATURE                Location/Qualifiers
source                 1..100
                       mol_type = genomic DNA
                       organism = Eubacterium sp.
SEQUENCE: 70
tacgtatggt gcaagcgtta tccggattta ctgggtgtaa agggtgagta ggcggtcatg  60
caagtcatat gtgaaatgtc agggcttaac cttggcgctg                      100

SEQ ID NO: 71          moltype = DNA  length = 100
FEATURE                Location/Qualifiers
source                 1..100
                       mol_type = genomic DNA
                       organism = Pediococcus parvulus
```

```
SEQUENCE: 71
tacgtaggtg gcaagcgtta tccggattta ttgggcgtaa agcgagcgca ggtggtcttt  60
taagtctaat gtgaaagcct tcggcttaac cgaagaagtg                        100

SEQ ID NO: 72          moltype = DNA  length = 100
FEATURE                Location/Qualifiers
source                 1..100
                       mol_type = genomic DNA
                       organism = Corynebacterium sp.
SEQUENCE: 72
tacgtagggt gcgagcgttg tccggaatta ctgggcgtaa agagctcgta ggtggtttgt  60
cgcgtcgttt gtgtaagccc gcagcttaac tgcgggactg                        100

SEQ ID NO: 73          moltype = DNA  length = 100
FEATURE                Location/Qualifiers
source                 1..100
                       mol_type = genomic DNA
                       organism = Lactobacillus plantarum
SEQUENCE: 73
tacgtaggtg gcaagcgttg tccgaattta ttgggcgtaa agcgagcgca ggcggttttt  60
taagtctgat gtgaaagcct tcggctcaac cgaagaagtg                        100

SEQ ID NO: 74          moltype = DNA  length = 100
FEATURE                Location/Qualifiers
source                 1..100
                       mol_type = genomic DNA
                       organism = Lactobacillus pontis
SEQUENCE: 74
tacgtaggtg gcaagcgtta tccggattta ttgggcgtaa agcgagcgca ggcggttact  60
taagtctgat gtgaaagcct tcggcttaac tgaagaagtg                        100

SEQ ID NO: 75          moltype = DNA  length = 100
FEATURE                Location/Qualifiers
source                 1..100
                       mol_type = genomic DNA
                       organism = Micrococcus antarcticus
SEQUENCE: 75
tacgtagggt gcgagcgtta tccggaatta ttgggcgtaa agagctcgta ggcggtttgt  60
cgcgtctgtc gtgaaagtcc ggggcttaac cccggatctg                        100

SEQ ID NO: 76          moltype = DNA  length = 100
FEATURE                Location/Qualifiers
source                 1..100
                       mol_type = genomic DNA
                       organism = Paracoccus marinus
SEQUENCE: 76
tacggagggg gctagcgttg ttcggaatta ctgggcgtaa agcgcacgta ggcggactgg  60
aaagttgggg gtgaaatccc ggggctcaac ctcggaactg                        100

SEQ ID NO: 77          moltype = DNA  length = 100
FEATURE                Location/Qualifiers
source                 1..100
                       mol_type = genomic DNA
                       organism = Lactobacillus brevis
SEQUENCE: 77
tacgtaggtg gcaggcgttg tccggattta ttgggcgtaa agcgagcgca ggcggttttt  60
taagtctgat gtgaaagcct tcggcttaac cggagaagtg                        100

SEQ ID NO: 78          moltype = DNA  length = 100
FEATURE                Location/Qualifiers
source                 1..100
                       mol_type = genomic DNA
                       organism = Anaerococcus nagyae
SEQUENCE: 78
tacgtaagga ccgagcgttg tccggaatca ttgggcgtaa agggtacgta ggcggctaga  60
aaagttagaa gtcaaaggct atagctcaac tatagtaagc                        100

SEQ ID NO: 79          moltype = DNA  length = 100
FEATURE                Location/Qualifiers
source                 1..100
                       mol_type = genomic DNA
                       organism = Lactobacillus manihotivorans
SEQUENCE: 79
tacgtaggtg gcaagcgtta tccggattta ttgggcgtaa agcgagcgca ggcggtttct  60
taagtctgat gtgaaagccc tcggctcaac cgaggaagtg                        100

SEQ ID NO: 80          moltype = DNA  length = 100
FEATURE                Location/Qualifiers
source                 1..100
```

```
                        mol_type = genomic DNA
                        organism = Lactobacillus acidophilus
SEQUENCE: 80
tacgtaggtg gcaagcgttg tccggattta ttgggcgtaa agcgagcgca ggcggctttt  60
taagtctgat gtgaaagcct tcggctcaac cgaagaagtg                        100

SEQ ID NO: 81           moltype = DNA  length = 100
FEATURE                 Location/Qualifiers
source                  1..100
                        mol_type = genomic DNA
                        organism = Lactobacillus sakei
SEQUENCE: 81
tacgtaggtc ccgagcgtta tccggattta ttgggcgtaa agcgagcgca ggcggttaga  60
taagtctgaa gttaaaggct gtggcttaac catagtacgc                        100

SEQ ID NO: 82           moltype = DNA  length = 100
FEATURE                 Location/Qualifiers
source                  1..100
                        mol_type = genomic DNA
                        organism = Lactobacillus sanfranciscensis
SEQUENCE: 82
tacgtaggtg gcaaacgttg tccggattta ttgggcgtaa agggagcgca ggcggtttat  60
taagtctgat gtgaaagcct tcggcttaac cggagaagta                        100

SEQ ID NO: 83           moltype = DNA  length = 100
FEATURE                 Location/Qualifiers
source                  1..100
                        mol_type = genomic DNA
                        organism = Lactobacillus sanfranciscensis
SEQUENCE: 83
tacgtaggtg gcaaacgttg tccggattta ttgggcgtaa agggagcgca ggcagtttat  60
taagtctgat gtgaaagcct tcggcttaac cggagaagtg                        100

SEQ ID NO: 84           moltype = DNA  length = 100
FEATURE                 Location/Qualifiers
source                  1..100
                        mol_type = genomic DNA
                        organism = Lactobacillus helveticus
SEQUENCE: 84
tacgtaggtg gcaagcgttg tccggattta ttgggcgtaa agcgagcgca ggcggaagaa  60
taagtctgat gtgaaagccc tcggcttaac cgaggaactg                        100

SEQ ID NO: 85           moltype = DNA  length = 100
FEATURE                 Location/Qualifiers
source                  1..100
                        mol_type = genomic DNA
                        organism = Gluconobacter albidus
SEQUENCE: 85
tacgaagggg gctagcgttg ctcggaatga ctgggcgtaa agggcgcgta ggcggtttgg  60
acagtcagat gtgaaatccc cgggcttaac ctgggaactg                        100

SEQ ID NO: 86           moltype = DNA  length = 100
FEATURE                 Location/Qualifiers
source                  1..100
                        mol_type = genomic DNA
                        organism = Ezakiella peruensis
SEQUENCE: 86
tacgtatggg gcgagcgttg tccggaatta ttgggcgtaa agggtacgca ggcggtttgc  60
caagttggat gtgaaatctt gtagctcaac tacaaacgtg                        100

SEQ ID NO: 87           moltype = DNA  length = 100
FEATURE                 Location/Qualifiers
source                  1..100
                        mol_type = genomic DNA
                        organism = Lactococcus sp.
SEQUENCE: 87
tacgtaggtc ccaagcgttg tccggattta ttgggcgtaa agcgagcgca ggtggtttct  60
taagtctgat gtaaaaggca gtggctcaac cattgtgtgc                        100

SEQ ID NO: 88           moltype = DNA  length = 100
FEATURE                 Location/Qualifiers
source                  1..100
                        mol_type = genomic DNA
                        organism = Lactobacillus paralimentarius
SEQUENCE: 88
tacgtaggtg gcaagcgttg tccggattta ttgggcgtaa agagaatgta ggcggtttat  60
taagtttgaa gtgaaagccc tcggctcaac cgaggaagta                        100

SEQ ID NO: 89           moltype = DNA  length = 100
```

```
FEATURE                Location/Qualifiers
source                 1..100
                       mol_type = genomic DNA
                       organism = Ruminococcus bicirculans
SEQUENCE: 89
tacgtaggga gcgagcgttg tccggaatta ctgggtgtaa agggagcgta ggcgggatcg  60
caagtcagat gtgaaaacta tgggcttaac ccataaactg                        100

SEQ ID NO: 90          moltype = DNA  length = 100
FEATURE                Location/Qualifiers
source                 1..100
                       mol_type = genomic DNA
                       organism = Corynebacterium macginleyi
SEQUENCE: 90
tacgtagggt gcgagcgttg tccggaatta ctgggcgtaa agggctcgta ggtggtttgt  60
cgcgtcgtct gtgaaattct ggggcttaac tccgggcgtg                        100

SEQ ID NO: 91          moltype = DNA  length = 100
FEATURE                Location/Qualifiers
source                 1..100
                       mol_type = genomic DNA
                       organism = Faecalibacterium sp.
SEQUENCE: 91
aacgtaggtc acaagcgttg tccggaatta ctgggtgtaa agggagcgca ggcgggaaga  60
caagttggaa gtgaaatcca tgggctcaac ccatgaactg                        100

SEQ ID NO: 92          moltype = DNA  length = 100
FEATURE                Location/Qualifiers
source                 1..100
                       mol_type = genomic DNA
                       organism = Lagierella massiliensis
SEQUENCE: 92
tacgtatggt gcgagcgttg tccggaatta ttgggcgtaa agggtacgta ggcggtttga  60
caagtcagat gttaaaactt gaggcttaac ctcatgttgc                        100

SEQ ID NO: 93          moltype = DNA  length = 100
FEATURE                Location/Qualifiers
source                 1..100
                       mol_type = genomic DNA
                       organism = Corynebacterium kroppenstedtii
SEQUENCE: 93
tacgtagggt gcgagcgttg tccggaatta ctgggcgtaa agagctcgta ggtggtctgt  60
cgcgtcattt gtgaaagccc ggggcttaac tccgggttgg                        100

SEQ ID NO: 94          moltype = DNA  length = 100
FEATURE                Location/Qualifiers
source                 1..100
                       mol_type = genomic DNA
                       organism = Rothia sp.
SEQUENCE: 94
tacgtagggc gcgagcgttg tccggaatta ttgggcgtaa agagcttgta ggcggtttgt  60
cgcgtctgct gtgaaaggcc ggggcttaac cccgtgtatt                        100

SEQ ID NO: 95          moltype = DNA  length = 100
FEATURE                Location/Qualifiers
source                 1..100
                       mol_type = genomic DNA
                       organism = Lactobacillus perolens
SEQUENCE: 95
tacgtaggtg gcaagcgttg tccggattta ttgggcgtaa agcgagtgca ggcggttttt  60
taagtctgat gtgaaagcct tcggcttaac cgaagaagtg                        100

SEQ ID NO: 96          moltype = DNA  length = 100
FEATURE                Location/Qualifiers
source                 1..100
                       mol_type = genomic DNA
                       organism = Pediococcus parvulus
SEQUENCE: 96
tacgtaggtg gcaagcgtta tccggattta ttgggcgtaa agcgagcgca ggcggtcttt  60
taagtctaat gtgaaagtct tcggcttaac cgaagaagtg                        100

SEQ ID NO: 97          moltype = DNA  length = 100
FEATURE                Location/Qualifiers
source                 1..100
                       mol_type = genomic DNA
                       organism = Lactobacillus sakei
SEQUENCE: 97
tacgtaggtg acaagcgttg tccggattta ttgggcgtaa agggagcgca ggcggtctgt  60
ttagtctaat gtgaaagccc acggcttaac cgtggaacgg                        100
```

```
SEQ ID NO: 98          moltype = DNA  length = 100
FEATURE                Location/Qualifiers
source                 1..100
                       mol_type = genomic DNA
                       organism = Lactobacillus siliginis
SEQUENCE: 98
tacgtaggtg gcaagcgtta tccggattta ttgggcgtaa agggagtgca ggcggttttt  60
taagtctgat gtgaaagcct tcggcttaac cggagaaggg                        100

SEQ ID NO: 99          moltype = DNA  length = 100
FEATURE                Location/Qualifiers
source                 1..100
                       mol_type = genomic DNA
                       organism = Lactobacillus sakei
SEQUENCE: 99
tacgtaggtc ccgagcgttg tccggattta ttgggcgtaa agcgagcgca ggcggtttaa  60
taagtctgaa gttaaaggca gtggcttaac cattgttcgc                        100

SEQ ID NO: 100         moltype = DNA  length = 100
FEATURE                Location/Qualifiers
source                 1..100
                       mol_type = genomic DNA
                       organism = Corynebacterium pseudodiphtheriticum
SEQUENCE: 100
tacgtagggt gcaagcgttg tccggaatta ctgggcgtaa agagctcgta ggtggtttgt  60
cacgtcgtct gtgaaattcc acagcttaac tgtgggcgtg                        100

SEQ ID NO: 101         moltype = DNA  length = 100
FEATURE                Location/Qualifiers
source                 1..100
                       mol_type = genomic DNA
                       organism = Peptoniphilus sp.
SEQUENCE: 101
tacgtagggg gctagcgttg tccggaatca ctgggcgtaa agggttcgca ggcggaataa  60
caagtcagat gtgaaaggca tgggctcaac ccatgtaagc                        100

SEQ ID NO: 102         moltype = DNA  length = 100
FEATURE                Location/Qualifiers
source                 1..100
                       mol_type = genomic DNA
                       organism = Pediococcus parvulus
SEQUENCE: 102
tacgtagatg gcaagcgtta tccggattta ttgggcgtaa agcgagcgca ggcggtcttt  60
taagtctaat gtgaaagcct tcggcttaac cgaagaagtg                        100

SEQ ID NO: 103         moltype = DNA  length = 100
FEATURE                Location/Qualifiers
source                 1..100
                       mol_type = genomic DNA
                       organism = Lactobacillus hilgardii
SEQUENCE: 103
tacgtaggtg gcaagcgttg tccggattta ttgggcgtaa agcgagcgcg ggcggttttt  60
taggtctgat gtgaaagcct tcggcttaac cggagaagtg                        100

SEQ ID NO: 104         moltype = DNA  length = 100
FEATURE                Location/Qualifiers
source                 1..100
                       mol_type = genomic DNA
                       organism = Lactobacillus sakei
SEQUENCE: 104
tacgtaggtg gcaagcgttg tccggattta ttgggcgtaa agcgagcgca ggcggttcct  60
taagtctgat gtgaaagccc ccggctcaac cggggagggt                        100

SEQ ID NO: 105         moltype = DNA  length = 100
FEATURE                Location/Qualifiers
source                 1..100
                       mol_type = genomic DNA
                       organism = Lactobacillus brevis
SEQUENCE: 105
tacgtaggtg gcaagcgttg tccggattta ttgggcgtaa agcgagcgca ggcggttttt  60
taagtctgat gtgaaagtct tcggcttaac cggagaagtg                        100

SEQ ID NO: 106         moltype = DNA  length = 100
FEATURE                Location/Qualifiers
source                 1..100
                       mol_type = genomic DNA
                       organism = Clostridium sp.
SEQUENCE: 106
```

-continued

```
tacgtaggga gcaagcgttg tccggaatca ctgggcgtaa agggttcgca ggcggcaatg  60
caagtctcgt gtgaaaggca agggctcaac ccttgtaagc                        100

SEQ ID NO: 107         moltype = DNA  length = 100
FEATURE                Location/Qualifiers
source                 1..100
                       mol_type = genomic DNA
                       organism = Lactobacillus sp.
SEQUENCE: 107
tacgtaggtg gcaagcgttg tccggattta ttgggcgtaa agcgagcgca ggcggttttt  60
taagtctaat gtgaaagcct tcggcttaac cgaagaagtg                        100

SEQ ID NO: 108         moltype = DNA  length = 100
FEATURE                Location/Qualifiers
source                 1..100
                       mol_type = genomic DNA
                       organism = Corynebacterium simulans
SEQUENCE: 108
tacgtagggt gcgagcgttg tccggaatta ctgggcgtaa agagctcgta ggtggtttgt  60
cgcgtcgtct gtgaaattcc ggggcttaac tccgggcgtg                        100

SEQ ID NO: 109         moltype = DNA  length = 100
FEATURE                Location/Qualifiers
source                 1..100
                       mol_type = genomic DNA
                       organism = Rothia sp.
SEQUENCE: 109
tacgtagggc gcgagcgttg tccggaatta ttgggcgtaa agagcttgta ggcggtttgt  60
cgcgtctgct gtgaaaggcc ggggcttaac tccgtgtatt                        100

SEQ ID NO: 110         moltype = DNA  length = 100
FEATURE                Location/Qualifiers
source                 1..100
                       mol_type = genomic DNA
                       organism = Brevibacterium luteolum
SEQUENCE: 110
tacgtagggt acaagcgttg tccggaatta ttgggcgtaa agagctcgta ggtggttggt  60
cacgtctgct gtggaaacgc aacgcttaac gttgcgcgtg                        100

SEQ ID NO: 111         moltype = DNA  length = 100
FEATURE                Location/Qualifiers
source                 1..100
                       mol_type = genomic DNA
                       organism = Lactobacillus sakei
SEQUENCE: 111
tacgtaggtg gcaagcgttg tccggaatta ttgggcgtaa agcgcgcgca ggcggttcct  60
taagtctgat gtgaaagccc acggctcaac cgtggagggt                        100

SEQ ID NO: 112         moltype = DNA  length = 100
FEATURE                Location/Qualifiers
source                 1..100
                       mol_type = genomic DNA
                       organism = Acidiphilium organovorum
SEQUENCE: 112
tacgaagggg gctagcgttg ctcggaatga ctgggcgtaa agggcgcgta ggcggaatgc  60
tttgtcgggc gtgaaattcc agggcttaac cttgggactg                        100

SEQ ID NO: 113         moltype = DNA  length = 100
FEATURE                Location/Qualifiers
source                 1..100
                       mol_type = genomic DNA
                       organism = Lactobacillus plantarum
SEQUENCE: 113
tacgtaggtg gcaagcgttg tccggattta ttgggcgtaa agcgagcgca ggcggtcttt  60
taagtctgat gtgaaagcct tcggctcaac cgaagaagtg                        100

SEQ ID NO: 114         moltype = DNA  length = 100
FEATURE                Location/Qualifiers
source                 1..100
                       mol_type = genomic DNA
                       organism = Peptoniphilus senegalensis
SEQUENCE: 114
tacgtagggg gctagcgttg tccggaatca ctgggcgtaa agggttcgca ggcggaaatg  60
caagtcagat gtaaaaggca gtagcttaac tactgtaagc                        100

SEQ ID NO: 115         moltype = DNA  length = 100
FEATURE                Location/Qualifiers
source                 1..100
                       mol_type = genomic DNA
```

```
                         organism = Lactobacillus paralimentarius
SEQUENCE: 115
tacgtaggtg gcaagcgttg tccggattta ttgggcgtaa agagaatgta ggcagtttat  60
taagtttgaa gtgaaagccc tcggctcaac cgaggaagtg                        100

SEQ ID NO: 116           moltype = DNA  length = 100
FEATURE                  Location/Qualifiers
source                   1..100
                         mol_type = genomic DNA
                         organism = Anaerococcus octavius
SEQUENCE: 116
tacgtaagga ccgagcgttg tccggaatca ttgggcgtaa agggtacgta ggcgggtcat  60
taagttagaa gtcaaaggct atagctcaac tatagtaagc                        100

SEQ ID NO: 117           moltype = DNA  length = 100
FEATURE                  Location/Qualifiers
source                   1..100
                         mol_type = genomic DNA
                         organism = Pediococcus parvulus
SEQUENCE: 117
tacgtaggtg gcaagcgtta tccggattta ttgggcgtaa agcgagcgca ggcggtcttt  60
taagtctaat gtgaaagcct tcggcttaac caaagaagtg                        100

SEQ ID NO: 118           moltype = DNA  length = 100
FEATURE                  Location/Qualifiers
source                   1..100
                         mol_type = genomic DNA
                         organism = Lactobacillus plantarum
SEQUENCE: 118
tacgtaggtg gcaagcgttg tccggattta ttgggcgtaa agcgagcgca ggcggttttt  60
taagtctgat gtgaaagcct ttggctcaac cgaagaagtg                        100

SEQ ID NO: 119           moltype = DNA  length = 100
FEATURE                  Location/Qualifiers
source                   1..100
                         mol_type = genomic DNA
                         organism = Rothia dentocariosa
SEQUENCE: 119
tacgtagggc gcgagcgttg tccggaatta ttgggcgtaa agagcttgta ggcggttggt  60
cgcgtctgct gtgaaaggct ggggcttaac cctggttttg                        100

SEQ ID NO: 120           moltype = DNA  length = 100
FEATURE                  Location/Qualifiers
source                   1..100
                         mol_type = genomic DNA
                         organism = Lactobacillus coryniformis
SEQUENCE: 120
tacgtaggtg gcaagcgttg tccggattta ttgggcgtaa agcgagcgca ggcggttttt  60
taagtctgat gtgaaagtct tcggcttaac cgaagaagtg                        100

SEQ ID NO: 121           moltype = DNA  length = 100
FEATURE                  Location/Qualifiers
source                   1..100
                         mol_type = genomic DNA
                         organism = Lactobacillus casei
SEQUENCE: 121
tacgtaggtg gcaagcgtta tccggattta ttgggcgtaa agcgagcgca ggcggttttt  60
taagtctgat gtgaaagccc tcggcttaac cgaggaagtg                        100

SEQ ID NO: 122           moltype = DNA  length = 100
FEATURE                  Location/Qualifiers
source                   1..100
                         mol_type = genomic DNA
                         organism = Corynebacterium sp.
SEQUENCE: 122
tacgtagggt gcgagcgttg tccggaatta ctgggcgtaa agagctcgta ggtggtttgt  60
cgcgtcgttt gtggaatacc gcagcttaac tgcggggttg                        100

SEQ ID NO: 123           moltype = DNA  length = 100
FEATURE                  Location/Qualifiers
source                   1..100
                         mol_type = genomic DNA
                         organism = Leuconostoc carnosum
SEQUENCE: 123
tacgtatgtc ccgagcgtta tccggattta ttgggcgtaa agcgagcgca gacggttggt  60
taagtctgat gtgaaagccc ggagctcaac tccggaaagg                        100

SEQ ID NO: 124           moltype = DNA  length = 100
FEATURE                  Location/Qualifiers
```

```
source                  1..100
                        mol_type = genomic DNA
                        organism = Lactobacillus selangorensis
SEQUENCE: 124
tacgtaggtg gcaagcgttg tccggattta ttgggcgtaa agcgagcgca ggcggttttt  60
taagtctgat gtgaaagccc tcggcttaac cgaggaagtg                        100

SEQ ID NO: 125          moltype = DNA  length = 100
FEATURE                 Location/Qualifiers
source                  1..100
                        mol_type = genomic DNA
                        organism = Lactobacillus sakei
SEQUENCE: 125
tacgtagggg gcaagcgttg tccggaatta ttgggcgtaa agcgcgcgca ggcggtcatt  60
taagtctggt gtttaatccc ggggctcaac cccggatcgc                        100

SEQ ID NO: 126          moltype = DNA  length = 100
FEATURE                 Location/Qualifiers
source                  1..100
                        mol_type = genomic DNA
                        organism = Lactobacillus sakei
SEQUENCE: 126
tacgtaggtg gcaagcgttg tccggaatta ttgggcgtaa agcgcgcgca ggcggtttct  60
taagtctgat gtgaaagccc acggctcaac cgtggagggt                        100

SEQ ID NO: 127          moltype = DNA  length = 100
FEATURE                 Location/Qualifiers
source                  1..100
                        mol_type = genomic DNA
                        organism = Lactobacillus sanfranciscensis
SEQUENCE: 127
tacgtaggtg gcaaacgttg tccggattta ttgggcgtaa agggagcgca ggcggtttat  60
taagtctaat gtgaaagcct tcggcttaac cggagaagtg                        100

SEQ ID NO: 128          moltype = DNA  length = 100
FEATURE                 Location/Qualifiers
source                  1..100
                        mol_type = genomic DNA
                        organism = Weissella cibaria
SEQUENCE: 128
tacgtatgtt ccaagcgtta tccggattta ttgggcgtaa agcgagcgca gacggttatt  60
taagtctgaa gtgaaagccc tcagctcaac tgaggaatgg                        100

SEQ ID NO: 129          moltype = DNA  length = 100
FEATURE                 Location/Qualifiers
source                  1..100
                        mol_type = genomic DNA
                        organism = Pediococcus pentosaceus
SEQUENCE: 129
gtgtcagcag ccgcggtaat acgtaggtgg caagcgttat ccggatttat tgggcgtaaa  60
gcgagcgcag gcggtctttt aagtctaatg tgaaagcctt                        100

SEQ ID NO: 130          moltype = DNA  length = 100
FEATURE                 Location/Qualifiers
source                  1..100
                        mol_type = genomic DNA
                        organism = Lactobacillus sakei
SEQUENCE: 130
tacgtaggtg gcaagcgttg tccggattta ttgggcgtaa agcgagcgca ggcggtcaat  60
taagtctgat gtgaaagccc ccggctcaac cggggagggt                        100

SEQ ID NO: 131          moltype = DNA  length = 100
FEATURE                 Location/Qualifiers
source                  1..100
                        mol_type = genomic DNA
                        organism = Lactobacillus fuchuensis
SEQUENCE: 131
tacgtaggtg gcaagcgttg tccggattta ttgggcgtaa agcgagcgca ggcggttttt  60
taagtctgat gtgaaagtct tcggctcaac cgaagaagtg                        100

SEQ ID NO: 132          moltype = DNA  length = 100
FEATURE                 Location/Qualifiers
source                  1..100
                        mol_type = genomic DNA
                        organism = Corynebacterium casei
SEQUENCE: 132
tacgtagggt gcaagcgttg tccggaatta ctgggcgtaa agagctcgta ggtggtttgt  60
cgcgtcgtct gtgaaatccc ggggcttaac ttcgggcgtg                        100
```

-continued

```
SEQ ID NO: 133         moltype = DNA  length = 100
FEATURE                Location/Qualifiers
source                 1..100
                       mol_type = genomic DNA
                       organism = Pediococcus argentinicus
SEQUENCE: 133
tacgtaggtg gcaagcgttg tccggattta ttgggcgtaa agcgagcgca ggcggttttt  60
taagtctaat gtgaaagcct tcggctcaac cgaagaagtg                        100

SEQ ID NO: 134         moltype = DNA  length = 100
FEATURE                Location/Qualifiers
source                 1..100
                       mol_type = genomic DNA
                       organism = Lactobacillus rossiae
SEQUENCE: 134
tacgtaggtg gcaagcgtta tccggattta ttgggcgtaa agggagtgca ggcggttatt  60
taagtctgat gtgaaagcct tcggctttac cggagaaggg                        100

SEQ ID NO: 135         moltype = DNA  length = 100
FEATURE                Location/Qualifiers
source                 1..100
                       mol_type = genomic DNA
                       organism = Lactobacillus siliginis
SEQUENCE: 135
tacgtaggtg gcaagcgtta tccggattta ttgggcgtaa agggagtgca ggcggttatt  60
taagtctgat gtgaaagcct tcggcttaac cggggaaggg                        100

SEQ ID NO: 136         moltype = DNA  length = 100
FEATURE                Location/Qualifiers
source                 1..100
                       mol_type = genomic DNA
                       organism = Pediococcus pentosaceus
SEQUENCE: 136
gtgtcagccg ccgcggtaat acgtaggtgg caagcgttat ccggatttat tgggcgtaaa  60
gcgagcgcag gcggtctttt aagtctaatg tgaaagcctt                        100

SEQ ID NO: 137         moltype = DNA  length = 100
FEATURE                Location/Qualifiers
source                 1..100
                       mol_type = genomic DNA
                       organism = Corynebacterium efficiens
SEQUENCE: 137
tacgtagggt gcgagcgttg tccggaatta ctgggcgtaa agagctcgta ggtggtttgt  60
cgcgtcgtct gtgaaatccc ggggcttaac ttcgggcgtg                        100

SEQ ID NO: 138         moltype = DNA  length = 100
FEATURE                Location/Qualifiers
source                 1..100
                       mol_type = genomic DNA
                       organism = Anaerococcus sp.
SEQUENCE: 138
tacgtaaggt ccgagcgttg tccggaatca ttgggcgtaa agggtacgta ggcgggtaag  60
caagttagaa gtgaaatcct atagctcaac tatagtaagc                        100

SEQ ID NO: 139         moltype = DNA  length = 100
FEATURE                Location/Qualifiers
source                 1..100
                       mol_type = genomic DNA
                       organism = Dermacoccus profundi
SEQUENCE: 139
tacgtagggt gcgagcgttg tccggaatta ttgggcgtaa agagcttgta ggcggtttgt  60
cgcgtctgct gtgaaagacc ggggcttaac tccggttctg                        100

SEQ ID NO: 140         moltype = DNA  length = 100
FEATURE                Location/Qualifiers
source                 1..100
                       mol_type = genomic DNA
                       organism = Eubacterium yurii
SEQUENCE: 140
tacgtagggg gcaagcgtta tccggaatta ctgggcgtaa agggtgcgta ggcggctagt  60
taagtcgagg ttaaaaggca gtagctcaac tactgttggg                        100

SEQ ID NO: 141         moltype = DNA  length = 100
FEATURE                Location/Qualifiers
source                 1..100
                       mol_type = genomic DNA
                       organism = Cutibacterium acnes
SEQUENCE: 141
tacgtagggt gcgagcgttg tccggattta ttgggcgtaa agggctcgta ggtggttgat  60
```

```
cgcgtcggaa gtgtaatctt ggggcttaac cctgagcgtg                      100

SEQ ID NO: 142         moltype = DNA  length = 100
FEATURE                Location/Qualifiers
source                 1..100
                       mol_type = genomic DNA
                       organism = Corynebacterium glucuronolyticum
SEQUENCE: 142
tacgtagggt gcgagcgttg tccggattta ctgggcgtaa agggctcgta ggtggtgtgt  60
cgcgtcgtct gtgtaatcca ggggcttaac ttttggttgg                      100

SEQ ID NO: 143         moltype = DNA  length = 100
FEATURE                Location/Qualifiers
source                 1..100
                       mol_type = genomic DNA
                       organism = Lactobacillus sanfranciscensis
SEQUENCE: 143
tacgtaggtg gcaaacgttg tccggattta ttgggcgtaa agggagtgca ggcggtttat  60
taagtctgat gtgaaagcct tcggcttaac cggagaagtg                      100

SEQ ID NO: 144         moltype = DNA  length = 100
FEATURE                Location/Qualifiers
source                 1..100
                       mol_type = genomic DNA
                       organism = Collinsella sp.
SEQUENCE: 144
tacgtagggg gcgagcgtta tccggattca ttgggcgtaa agcgcgcgta ggcggcccgg  60
caggccgggg gtcgaagcgg ggggctcaac cccccgaagc                      100

SEQ ID NO: 145         moltype = DNA  length = 100
FEATURE                Location/Qualifiers
source                 1..100
                       mol_type = genomic DNA
                       organism = Stomatobaculum longum
SEQUENCE: 145
tacgtagggg gcaagcgtta tccggattta ctgggtgtaa agggagcgca gacggctctg  60
caagtctgaa gtgaaagccc gcggcttaac cgcgggactg                      100

SEQ ID NO: 146         moltype = DNA  length = 100
FEATURE                Location/Qualifiers
source                 1..100
                       mol_type = genomic DNA
                       organism = Bacteriovorax stolpii
SEQUENCE: 146
tacgaagggt gcaagcgttg ttcggattta ttgggcgtaa agcgcgcgca ggcggacctg  60
taagtcagat gtgaaatctc ggggctcaac tccgaaactg                      100

SEQ ID NO: 147         moltype = DNA  length = 100
FEATURE                Location/Qualifiers
source                 1..100
                       mol_type = genomic DNA
                       organism = Rothia sp.
SEQUENCE: 147
tacgtagggc gcgagcgttg tccggaatta ttgggcgtaa agagcttgta ggcggtttgt  60
cgcgtctgct gtgaaaggcc ggagcttaac tccgtgtatt                      100

SEQ ID NO: 148         moltype = DNA  length = 100
FEATURE                Location/Qualifiers
source                 1..100
                       mol_type = genomic DNA
                       organism = Corynebacterium faecale
SEQUENCE: 148
tacgtagggt gcgagcgttg tccggaatta ctgggcgtaa agagctcgta ggtggtttgt  60
cacgtcgtct gtgaaatccc ggggcttaac ctcgggcgtg                      100

SEQ ID NO: 149         moltype = DNA  length = 100
FEATURE                Location/Qualifiers
source                 1..100
                       mol_type = genomic DNA
                       organism = Lactococcus sp.
SEQUENCE: 149
tacgtaggtc ccgagcgttg tccggattta ttgggcgtaa agcgagcgca ggtggtttaa  60
taagtctgat gtaaaaggca gtggctcaac cattgtgtgc                      100

SEQ ID NO: 150         moltype = DNA  length = 100
FEATURE                Location/Qualifiers
source                 1..100
                       mol_type = genomic DNA
                       organism = Armatimonas rosea
```

```
SEQUENCE: 150
tacgtagggg gcgagcgttg tccgaagtta ctgggcgtaa agcgcgcgta ggcggctttt  60
taagtttgag gtgaaaggtt cagcgctcaa cgtgaacagt                        100

SEQ ID NO: 151         moltype = DNA  length = 100
FEATURE                Location/Qualifiers
source                 1..100
                       mol_type = genomic DNA
                       organism = Lactobacillus sakei
SEQUENCE: 151
tacgtaggtg gcaagcgttg tccggaatta ttgggcgtaa agcgcgcgca ggtggtttaa  60
taagtctgat gtgaaagccc acggctcaac cgtggagggt                        100

SEQ ID NO: 152         moltype = DNA  length = 100
FEATURE                Location/Qualifiers
source                 1..100
                       mol_type = genomic DNA
                       organism = Acidiphilium organovorum
SEQUENCE: 152
tacgaagggg gctagcgttg ctcggaatga ctgggcgtaa agggcgcgta ggcggatcgg  60
acagtcgggc gtgaaattcc tggctcaac ctggggactg                         100

SEQ ID NO: 153         moltype = DNA  length = 100
FEATURE                Location/Qualifiers
source                 1..100
                       mol_type = genomic DNA
                       organism = Lactobacillus sp.
SEQUENCE: 153
tacgtatggt gcaagcgtta tccggattta ctgggtgtaa agggagcgca ggcggtgcgg  60
caagtctgat gtgaaagccc ggggctcaac cccggtactg                        100

SEQ ID NO: 154         moltype = DNA  length = 100
FEATURE                Location/Qualifiers
source                 1..100
                       mol_type = genomic DNA
                       organism = Lactobacillus sakei
SEQUENCE: 154
tacgtaggtc ccgagcgttg tccggattta ttgggcgtaa agcgagcgca ggcggttaga  60
taagtctgaa gttaaaggct gtggcttaac catagtatgc                        100

SEQ ID NO: 155         moltype = DNA  length = 100
FEATURE                Location/Qualifiers
source                 1..100
                       mol_type = genomic DNA
                       organism = Anaerotignum lactatifermentans
SEQUENCE: 155
tacgtagggg gcaagcgtta tccggaatta ctgggtgtaa agggagcgta ggcggcatgg  60
taagccagat gtgaaagcct tgggcttaac ccgaggattg                        100

SEQ ID NO: 156         moltype = DNA  length = 100
FEATURE                Location/Qualifiers
source                 1..100
                       mol_type = genomic DNA
                       organism = Brachybacterium conglomeratum
SEQUENCE: 156
tacgtagggc gcaagcgttg tccggaatta ttgggcgtaa agagcttgta ggtggcttgt  60
cgcgtctgcc gtgaaaaccc gaggctcaac ctcgggcgtg                        100

SEQ ID NO: 157         moltype = DNA  length = 200
FEATURE                Location/Qualifiers
source                 1..200
                       mol_type = genomic DNA
                       organism = Saccharomyces sp.
SEQUENCE: 157
gagaaccaag agatccgttg ttgaaagttt ttaatatttt aaaatttcca gttacgaaaa  60
ttcttgtttt tgacaaaaat ttaatgaata gataaaattg tttgtgtttg ttacctctgg  120
gccccgattg ctcgaatgcc caaagaaaaa gttgcaaaga tatgaaaact ccacagtgtg  180
ttgtattgaa acggttttaa                                              200

SEQ ID NO: 158         moltype = DNA  length = 200
FEATURE                Location/Qualifiers
source                 1..200
                       mol_type = genomic DNA
                       organism = Kazachstania exigua
SEQUENCE: 158
gagaaccaag agatccgttg ttgaaagttt tgaatatttt ggttactgca ataaagcaga  60
ttttgaaatg acaaattaaa ataataaaaa ataattgttt gtgttttgtt ttggcggtat  120
tgctacctcc gatactgtag aaataaaact ccagtgtgtg taaagaatta tcggcgtaac  180
gaaaaagaac aacctcgccg                                              200
```

```
SEQ ID NO: 159          moltype = DNA  length = 200
FEATURE                 Location/Qualifiers
source                  1..200
                        mol_type = genomic DNA
                        organism = Kazachstania humilis
SEQUENCE: 159
gagaaccaag agatccgttg ttgaaagttt tgaatatttt ggttactgcg taagcagatt  60
tgatgacgtt gtataataga aaatagttgt ttgtgtttgg cgagctgagc tttcgcccag  120
cccaagaata aataattact ccactgtgtg taagaggcgg agcgccaccg cgcagctaag  180
cgcaggcagg ctcccccaat                                              200

SEQ ID NO: 160          moltype = DNA  length = 200
FEATURE                 Location/Qualifiers
source                  1..200
                        mol_type = genomic DNA
                        organism = Saccharomyces paradoxus
SEQUENCE: 160
gagaaccaag agatccgttg ttgaaagttt ttaatatttt aaaatttcca gttacgaaaa  60
ttcttgtttt tgacaaaaat ttaatgaata aataaaattg tttgtgtttg ttacctctgg  120
gccccgattg ctcgaatgcc caaagaaaaa gttgcaaaga tatgaaaact ccacagtgtg  180
ttgtattgaa acggttttaa                                              200

SEQ ID NO: 161          moltype = DNA  length = 200
FEATURE                 Location/Qualifiers
source                  1..200
                        mol_type = genomic DNA
                        organism = Saccharomyces sp.
SEQUENCE: 161
gagaaccaag agatccgttg ttgaaagttt ttaatatttt aaaatttcca gttacgaaaa  60
ttcttgtttt tgacaaaaat ttaatgaata gataaaattg tttgtgtttg ttaacctctg  120
ggccccgatt gctcgaatgc ccaaagaaaa agttgcaaag atatgaaaac tccacagtgt  180
gttgtattga aacggtttta                                              200

SEQ ID NO: 162          moltype = DNA  length = 200
FEATURE                 Location/Qualifiers
source                  1..200
                        mol_type = genomic DNA
                        organism = Kazachstania servazzii
SEQUENCE: 162
gagaaccaag agatccgttg ttgaaagttt taatatttgt tttaatatta caaaaagata  60
aatcttcctg gaattctggt tttgactagt tcataaaatt acaaaattgt ttgtgtttgt  120
cactcctggg ccgccgaagc agcccaaaga agcatgcaaa gaattataaa aatctccact  180
gtgtgtaata gtgctactga                                              200

SEQ ID NO: 163          moltype = DNA  length = 200
FEATURE                 Location/Qualifiers
source                  1..200
                        mol_type = genomic DNA
                        organism = Saccharomyces cerevisiae
SEQUENCE: 163
cttggtcatt tagaggaagt aaaagtcgta acaaggtttc cgtaggtgaa cctgcggaag  60
gatcattaaa gaaatttaat aattttgaaa atggattttt ttgttttggc aagagcatga  120
gagcttttac tgggcaagaa gacaagagat ggagagtcca gccgggcctg cgcttaagtg  180
cgcggtcttg ctaggcctgt                                              200

SEQ ID NO: 164          moltype = DNA  length = 200
FEATURE                 Location/Qualifiers
source                  1..200
                        mol_type = genomic DNA
                        organism = Kazachstania humilis
SEQUENCE: 164
gagaaccaag agatccgttg ttgaaagttt tgaatatttt ggttactgcg taagcagatt  60
tgatgacatt gtataataaa aaatagttgt ttgtgtttgg cgagcagagc tttcgctcag  120
cccaagaata agtaattact ccactgtgtg taagaggtgg aacgccaccg cgcagctaag  180
cgcaggcggg ctcccccaat                                              200

SEQ ID NO: 165          moltype = DNA  length = 200
FEATURE                 Location/Qualifiers
source                  1..200
                        mol_type = genomic DNA
                        organism = Pichia fermentans
SEQUENCE: 165
gagaaccaag agatccgttg ttgaaagttt tgtggatttc ttgcttgacg gcgtgcgttc  60
ggtttcggtg tttcgtgtcg cccacgcagt gtggtggata aatcacagta atgatccttc  120
cgcaggttca cctacggaaa ccttgttacg acttttactt cctctaaatg accaagccgt  180
gtagatctcg gtggtcgccg                                              200

SEQ ID NO: 166          moltype = DNA  length = 200
```

```
FEATURE                 Location/Qualifiers
source                  1..200
                        mol_type = genomic DNA
                        organism = Naumovozyma castellii
SEQUENCE: 166
gagaaccaag agatccgttg ttgaaagttt taaattattt gtatttcata acgaaattgg  60
ttttgacttg attataatat aacaaaattg tttgtgtttg tcaactccgg gctcttgcaa  120
gcccaaagaa gaagaagtgt tttaaaagaa aactccagtg tgtgtataat ttttaggcag  180
tgaaccgcag acagagaaac                                              200

SEQ ID NO: 167          moltype = DNA  length = 200
FEATURE                 Location/Qualifiers
source                  1..200
                        mol_type = genomic DNA
                        organism = Candida sake
SEQUENCE: 167
gagaaccaag agatccgttg ttgaaagttt tgatattttt atttgttgac taagtaaatt  60
attagtgttc ttgcaagcaa gttctctaaa aaaacatgtg taatgcaatt aagcaaactt  120
taatgatcct tccgcaggtt cacctacgga aaccttgtta cgacttttac ttcctctaaa  180
tgaccaagcc gtgtagatct                                              200

SEQ ID NO: 168          moltype = DNA  length = 200
FEATURE                 Location/Qualifiers
source                  1..200
                        mol_type = genomic DNA
                        organism = Kazachstania humilis
SEQUENCE: 168
gagaaccaag agatccgttg ttgaaagttt tgaatatttt ggttactgcg taagcagatt  60
tgatgacgtt gtatagtaaa aaatagttgt ttgtgtttgg cgagatggac tttcgtccac  120
cccaagaata agtaattact ccactgtgtg taagaggtgg aacgccaccg cgcagctaag  180
cgcaggcggg ctcccccaat                                              200

SEQ ID NO: 169          moltype = DNA  length = 200
FEATURE                 Location/Qualifiers
source                  1..200
                        mol_type = genomic DNA
                        organism = Kazachstania unispora
SEQUENCE: 169
gagaaccaag agatccgttg ttgaaagttt tgaatatttg ttataatatt acaaaaagat  60
aaatctttct ggaattctgg ttttgactgg gttaaaaata ttacaaagtt gtttgtgttt  120
gttacctctg ggctgccgaa gctgcccaaa gaagcatgca aagaattata aaatctccac  180
agtgtgtaat agtgctactg                                              200

SEQ ID NO: 170          moltype = DNA  length = 200
FEATURE                 Location/Qualifiers
source                  1..200
                        mol_type = genomic DNA
                        organism = Saccharomyces sp.
SEQUENCE: 170
gagaaccaag agatccgttg ttgaaagttt ttaatatttt aaaatttcca gttacgaaaa  60
ttcttgtttt tgacgaaaat ttaatgaata gataaaattg tttgtgtttg ttaacctctg  120
ggccccgatt gctcgaatgc ccaaagaaaa agttgcaaag atatgaaaac tccacagtgt  180
gttgtattga aacggtttta                                              200

SEQ ID NO: 171          moltype = DNA  length = 200
FEATURE                 Location/Qualifiers
source                  1..200
                        mol_type = genomic DNA
                        organism = Kazachstania barnettii
SEQUENCE: 171
gagaaccaag agatccgttg ttgaaagttt tgaatatttt ggttactgtc agagacagat  60
ttgtgttgac gatgtataat aaaaaaggtt gtttgtgttt tgtgtggaca gatgcaaaag  120
caactgcccg ataaagtata aaatactcca cagtgtgtag aataaccagc gtgaaatgga  180
aacgcccgct tgccgcgcac                                              200

SEQ ID NO: 172          moltype = DNA  length = 200
FEATURE                 Location/Qualifiers
source                  1..200
                        mol_type = genomic DNA
                        organism = Kazachstania humilis
SEQUENCE: 172
gagaaccaag agatccgttg ttgaaagttt tgaatatttt ggttactgcg taagcagatt  60
tgatgacact gtataataga aaatagttgt ttgtgtttgg cgagctggac tttcgcccag  120
cccaagaata agtaattact ccactgtgtg taagaggcgg agcgccaccg cgcagctaag  180
cgcaggcggg ctcccccaat                                              200

SEQ ID NO: 173          moltype = DNA  length = 200
FEATURE                 Location/Qualifiers
source                  1..200
```

```
                         mol_type = genomic DNA
                         organism = Pichia fermentans
SEQUENCE: 173
gagaaccaag agatccgttg ttgaaagttt tgtggatttc ttgcttgacg gcgtgcgttc  60
ggtttcggtg tttcgtgtcg cccacgcagt gtggtgtata aatcacagta atgatccttc  120
cgcaggttca cctacggaaa ccttgttacg acttttactt cctctaaatg accaagccgt  180
gtagatctcg gtggtcgccg                                              200

SEQ ID NO: 174           moltype = DNA  length = 200
FEATURE                  Location/Qualifiers
source                   1..200
                         mol_type = genomic DNA
                         organism = Saccharomyces pastorianus
SEQUENCE: 174
gagaaccaag agatccgttg ttgaaagttt ttaattattt ttaaaatttc cagttacgaa  60
aattcttgtt tttgacaaaa atttaatgaa taaataaaat tgtttgtgtt tgttacctct  120
gggctcgatt gctcgaagcc caaagaaaaa gttgcaaaag tataaaaact ccacagtgtg  180
ttgtattgaa acggttttaa                                              200

SEQ ID NO: 175           moltype = DNA  length = 200
FEATURE                  Location/Qualifiers
source                   1..200
                         mol_type = genomic DNA
                         organism = Kazachstania bulderi
SEQUENCE: 175
gagaaccaag agatccgttg ttgaaagttt tgaatatttt ggttactgca ataaagcaga  60
ttttgaaatg actattaaaa taataaaaaa aagaattgtt tgtgttttgt tttgggagta  120
ttgctactcc cgatactcta gaataaaact ccagtgtgtg taagaattat cggtttaaaa  180
cgaagagaac tagcctcacc                                              200

SEQ ID NO: 176           moltype = DNA  length = 200
FEATURE                  Location/Qualifiers
source                   1..200
                         mol_type = genomic DNA
                         organism = Saccharomyces cerevisiae
SEQUENCE: 176
catggtcatt tagaggaagt aaaagtcgta acaaggtttc cgtaggtgaa cctgcggaag  60
gatcattaaa gaaatttaat aattttgata ttggattttt ttgttttggc aagagcgtga  120
gagcttttac tgggcaagaa gacaagagat ggagagtcca gccgggcctg cgcttaagtg  180
cgcggtcttg ctaggcttgc                                              200

SEQ ID NO: 177           moltype = DNA  length = 200
FEATURE                  Location/Qualifiers
source                   1..200
                         mol_type = genomic DNA
                         organism = Wickerhamomyces anomalus
SEQUENCE: 177
gagaaccaag agatccgttg ttgaaagttt tgaagatttt aatttttgtt aaaaattttc  60
atgactattg gttaaaggtt ttaacattaa aaaaaatgtg tttagacctt tgggcagtaa  120
gccaggctca ccacccaaag caaagttcaa aaaaactaga caatgtgtgt aaggtttatc  180
gccgcgcaat taagcgctgg                                              200

SEQ ID NO: 178           moltype = DNA  length = 200
FEATURE                  Location/Qualifiers
source                   1..200
                         mol_type = genomic DNA
                         organism = Wickerhamomyces anomalus
SEQUENCE: 178
gagaaccaag agatccgttg ttgaaagttt tgaagatttt aatttttgtt aaaaattttc  60
atgactattg gttaaaggtt ttaacattaa aaaaaatgtg tttagacctt tgggcgcgca  120
gctaggctga tgcacccaaa gcaaagttca aaaaaactag acaatgtgtg taaggtttat  180
cgccgcgcaa ttaagcgctg                                              200

SEQ ID NO: 179           moltype = DNA  length = 200
FEATURE                  Location/Qualifiers
source                   1..200
                         mol_type = genomic DNA
                         organism = Pichia membranifaciens
SEQUENCE: 179
gagaaccaag agatccgttg ttgaaagttt tattctttta gatcttttgt tgacgtgtgt  60
atactccagg tttaggtgtt ttgtgcgccc acacagtgtg gtgttggtat aatcacagta  120
atgatccttc cgcaggttca cctacggaaa ccttgttacg acttttactt cctctaaatg  180
accaagccgt gtagatctcg                                              200

SEQ ID NO: 180           moltype = DNA  length = 200
FEATURE                  Location/Qualifiers
source                   1..200
                         mol_type = genomic DNA
                         organism = Wickerhamomyces anomalus
```

```
SEQUENCE: 180
gagaaccaag agatccgttg ttgaaagttt tgaagatttt aatttttgtt aaaaattttc  60
atgactattg gttaaaggtt ttaacattaa aaaatgtgtt tagacctttg ggcacgcagc  120
taggctgatg cacccaaagc aaagttcaaa aaaactagac aatgtgtgta aggtttatcg  180
ccgcgcaatt aagcgctggc                                             200

SEQ ID NO: 181         moltype = DNA  length = 200
FEATURE                Location/Qualifiers
source                 1..200
                       mol_type = genomic DNA
                       organism = Candida sake
SEQUENCE: 181
gagaaccaag agatccgttg ttgaaagttt tgatatttat attggttgac taagtaaatt  60
attagtgttc ttgcaagcaa gttctctaaa aaaacatgtg tgatgcaatt aagcaaactt  120
taatgatcct tccgcaggtt cacctacgga aaccttgtta cgacttttac ttcctctaaa  180
tgaccaagcc gtgtagatct                                             200

SEQ ID NO: 182         moltype = DNA  length = 200
FEATURE                Location/Qualifiers
source                 1..200
                       mol_type = genomic DNA
                       organism = Wickerhamomyces anomalus
SEQUENCE: 182
gagaaccaag agatccgttg ttgaaagttt tgaagatttt aatttttgtt aaaaattttc  60
atgactattg gttaaaggtt ttaacattaa aaaaatgtgt ttagaccttt gggcacgcag  120
ctaggctgat gcacccaaag caaagttcaa aaaaactaga caatgtgtgt aaggtttatc  180
gccgcgcaat taagcgctgg                                             200

SEQ ID NO: 183         moltype = DNA  length = 200
FEATURE                Location/Qualifiers
source                 1..200
                       mol_type = genomic DNA
                       organism = Saccharomyces cerevisiae
SEQUENCE: 183
cttggtcatt tagaggaagt aaaagtcgta acaaggtttc cgtaggtgaa cctgcggaag  60
gatcattaaa gaaatttaat aattttgata ttggattttt ttgttttggc aagagcgtga  120
gagcttttac tgggcaagaa gacaagagat ggagagtcca gccgggcctg cgcttaagtg  180
cgcggtcttg ctaggcttgc                                             200

SEQ ID NO: 184         moltype = DNA  length = 200
FEATURE                Location/Qualifiers
source                 1..200
                       mol_type = genomic DNA
                       organism = Pichia kudriavzevii
SEQUENCE: 184
gagaaccaag agatccgttg ttgaaagttt tgtttgtttt tcgtagattt ctcttgtcga  60
ctatatgcta tattccacat tttaggtgtt tttgttttcg ttccgctcac gcagtgtagt  120
actaaatcac agtaatgatc cttccgcagg ttcacctacg gaaaccttgt tacgactttt  180
acttcctcta aatgaccaag                                             200

SEQ ID NO: 185         moltype = DNA  length = 200
FEATURE                Location/Qualifiers
source                 1..200
                       mol_type = genomic DNA
                       organism = Wickerhamomyces anomalus
SEQUENCE: 185
gagaaccaag agatccgttg ttgaaagttt tgaagatttt aatttttgtt aaaaattttc  60
atgactattg gttaaaggtt ttaacattaa aaaaatgtgt ttagaccttt gggcagtaag  120
ccaggctcac cacccaaagc aaagttcaaa aaaactagac aatgtgtgta aggtttatcg  180
ccgcgcaatt aagcgctggc                                             200

SEQ ID NO: 186         moltype = DNA  length = 200
FEATURE                Location/Qualifiers
source                 1..200
                       mol_type = genomic DNA
                       organism = Saccharomyces paradoxus
SEQUENCE: 186
gagaaccaag agatccgttg ttgaaagttt ttaatatttt aaaatttcca gttacgaaaa  60
ttcttgtttt ttgacaaaaa tttaatgaat aaataaaatt gtttgtgttt gttacctctg  120
ggccccgatt gctcgaatgc ccaaagaaaa agttgcaaag atatgaaaac tccacagtgt  180
gttgtattga aacggtttta                                             200

SEQ ID NO: 187         moltype = DNA  length = 200
FEATURE                Location/Qualifiers
source                 1..200
                       mol_type = genomic DNA
                       organism = Hanseniaspora sp.
SEQUENCE: 187
gagaaccaag agatccgttg ttgaaagttt taaattattt taaaatttcc gttaggaatt  60
```

```
ttggtttagt ttaaaaaatt ataataaaat aaaattgttt gtgtttgttt tttgccttga  120
acctttcgat tcaaagcaga aagaattaaa ttaaagtaaa aaactccaat gtgtgtagcg  180
ttgactgaga ttcaagcaag                                              200

SEQ ID NO: 188         moltype = DNA  length = 200
FEATURE                Location/Qualifiers
source                 1..200
                       mol_type = genomic DNA
                       organism = Pichia membranifaciens
SEQUENCE: 188
gagaaccaag agatccgttg ttgaaagttt tattctttta gatcttttgt tgactgctgt  60
tatactatag tttatgtgtt tcgtgcgccc acacagtgtg gtgttaaaaa atcacagtaa  120
tgatccttcc gcaggttcac ctacggaaac cttgttacga cttttacttc ctctaaatga  180
ccaagccgtg tagatctcgg                                              200

SEQ ID NO: 189         moltype = DNA  length = 200
FEATURE                Location/Qualifiers
source                 1..200
                       mol_type = genomic DNA
                       organism = Penicillium sp.
SEQUENCE: 189
gtaggtgaac ctgcggaagg atcattactg agtgagggcc ctctgggtcc aacctcccac  60
ccgtgtttat ttaccttgtt gcttcggcgg gcccgcctta actggccgcc ggggggctta  120
cgcccccggg cccgcgcccg ccgaagacac cctcgaactc tgtctgaaga ttgtagtctg  180
agtgaaaata taaattattt                                              200

SEQ ID NO: 190         moltype = DNA  length = 200
FEATURE                Location/Qualifiers
source                 1..200
                       mol_type = genomic DNA
                       organism = Hanseniaspora sp.
SEQUENCE: 190
gagaaccaag agatccgttg ttgaaagttt taaattattt taaaatttcc gttaggaatt  60
ttggtttagt ttaaaaaatt ataataaaat aaaattgttt gtgtttgttt tttgccttga  120
acctttcgat tcaaagcaga aagaattaaa ttaaagtaaa aaaactccaa tgtgtgtagc  180
gttgactgag attcaagcaa                                              200

SEQ ID NO: 191         moltype = DNA  length = 200
FEATURE                Location/Qualifiers
source                 1..200
                       mol_type = genomic DNA
                       organism = Meyerozyma guilliermondii
SEQUENCE: 191
gagaaccaag agatccgttg ttgaaagttt tgaagattaa ttcaaaattt gactaactgt  60
aaaaataatt aaattgtgtt ttgttaaacc tctggcccaa cctatctcta ggccaaacca  120
aagcaagagt tctgtatcaa aaagacactg tgtgtaaggt ttttcgccgc gcagttaagc  180
gctggcaaaa gaatactgta                                              200

SEQ ID NO: 192         moltype = DNA  length = 200
FEATURE                Location/Qualifiers
source                 1..200
                       mol_type = genomic DNA
                       organism = Saccharomyces sp.
SEQUENCE: 192
gagaaccaag agatccgttg ttgaaagttt ttaatatttt aaaatttcca gttacgaaaa  60
ttcttgtttt tgacaaaaat ttaatgaata gataaaattg tttgtgtttg ttaacctctg  120
ggccccgatt gctcgaatgc ccaaagaaaa agttgcaaag atatgaaaac tccacggtgt  180
gttgtattga aacggtttta                                              200

SEQ ID NO: 193         moltype = DNA  length = 200
FEATURE                Location/Qualifiers
source                 1..200
                       mol_type = genomic DNA
                       organism = Saccharomyces pastorianus
SEQUENCE: 193
gagaaccaag agatccgttg ttgaaagttt ttaattattt ttaaaatttc cagttacgaa  60
aattcttgtt tttgacaaaa atttaatgaa taaataaaat tgtttgtgtt tgttacctct  120
gggctcgatt gctcgaaacc caaagaaaaa gttgcaaaag tataaaaact ccacagtgtg  180
ttgtattgaa acggttttaa                                              200

SEQ ID NO: 194         moltype = DNA  length = 200
FEATURE                Location/Qualifiers
source                 1..200
                       mol_type = genomic DNA
                       organism = Wickerhamomyces anomalus
SEQUENCE: 194
gagaaccaag agatccgttg ttgaaagttt tgaagatttt aatttttgtt aaaaattttc  60
atgactattg gttaaaggtt ttaacattaa aaaaaatgtg tttagacctt tgggcacgca  120
gctaggctga tgcacccaaa gcaaagttca aaaaaactag acaatgtgtg taaggtttat  180
```

```
cgccgcgcaa ttaagcgctg                                                  200

SEQ ID NO: 195         moltype = DNA  length = 200
FEATURE                Location/Qualifiers
source                 1..200
                       mol_type = genomic DNA
                       organism = Candida glabrata
SEQUENCE: 195
gagaaccaag agatccattg ttgaaagttt tgaagttgtt ttctactaaa agaaatcttg  60
tgttgactga attagtttaa aaaaatattt gtttgtgttt gcatccactg ggagaactcc  120
cccccgaaag agagcgttcc cccaacgaac aaaagaatag tagtaaagta aactccactg  180
tgtgtagtaa ttagaaagtg                                                  200

SEQ ID NO: 196         moltype = DNA  length = 200
FEATURE                Location/Qualifiers
source                 1..200
                       mol_type = genomic DNA
                       organism = Debaryomyces delbrueckii
SEQUENCE: 196
gagaaccaag agatccgttg ttgaaagttt taaatatttt taatttcata acgaaattgg  60
ttttgactgg tttataataa taaaaagttg tttgtgtttg tcacctctgg gaagcacgca  120
caagacgtat cttcccaaag aagaaaagtt gtgtagaaaa ctccacagtg ttgtagaagt  180
tgaagtagag ttaacaacga                                                  200

SEQ ID NO: 197         moltype = DNA  length = 200
FEATURE                Location/Qualifiers
source                 1..200
                       mol_type = genomic DNA
                       organism = Kazachstania naganishii
SEQUENCE: 197
gagaaccaag agatccgttg ttgaaagttt taaattttgt tgtttaaaaa gctaaacaga  60
tttctgactg ggtcactgca taattgtttg tgtttgttac ctctgggcgg ctgcccaaag  120
aaaaaagcgt agaaaaaatc tccacagtgt gtgagtttcg ccggggcgcc gcaccgcgca  180
actaagcgca gcactgcctc                                                  200

SEQ ID NO: 198         moltype = DNA  length = 200
FEATURE                Location/Qualifiers
source                 1..200
                       mol_type = genomic DNA
                       organism = Pichia cephalocereana
SEQUENCE: 198
gagaaccaag agatccgttg ttgaaagttt tgttttgtta aaacttagtg actggtatta  60
ttacaatttt aggtgtttgg tgcgctcacg catgtgtata agatataaat cacagtaatg  120
atccttccgc aggttcacct acggaaacct tgttacgact tttacttcct ctaaatgacc  180
aagccgtgta gatctcggtg                                                  200

SEQ ID NO: 199         moltype = DNA  length = 200
FEATURE                Location/Qualifiers
source                 1..200
                       mol_type = genomic DNA
                       organism = Saccharomyces paradoxus
SEQUENCE: 199
gagaaccaag agatccgttg ttgaaagttt ttaatatttt aaaatttcca gttacgaaaa  60
ttcttgtttt tgacaaaaat ttaatgaata gataaaattg tttgtgtttg ttacctctgg  120
gccccccgat tgctcgaatg cccaaagaaa aagttgcaaa gatatgaaaa ctccacagtg  180
tgttgtattg aaacggtttt                                                  200

SEQ ID NO: 200         moltype = DNA  length = 200
FEATURE                Location/Qualifiers
source                 1..200
                       mol_type = genomic DNA
                       organism = Saccharomyces sp.
SEQUENCE: 200
gagaaccaag agatctgttg ttgaaagttt ttaatatttt aaaatttcca gttacgaaaa  60
ttcttgtttt tgacaaaaat ttaatgaata gataaaattg tttgtgtttg ttacctctgg  120
gccccgattg ctcgaatgcc caaagaaaaa gttgcaaaga tatgaaaact ccacagtgtg  180
ttgtattgaa acggttttaa                                                  200

SEQ ID NO: 201         moltype = DNA  length = 200
FEATURE                Location/Qualifiers
source                 1..200
                       mol_type = genomic DNA
                       organism = Pichia kudriavzevii
SEQUENCE: 201
gagaaccaag agatccgttg ttgaaagttt ttcgttttcg tagatttctc ttgtcgacta  60
tatgctatat tccacatttt aggtgttgtt gttttcgttc cgctcacgca gtgtagtagt  120
aaatcacagt aatgatcctt ccgcaggttc acctacggaa accttgttac gacttttact  180
tcctctaaat gaccaagccg                                                  200
```

```
SEQ ID NO: 202         moltype = DNA  length = 200
FEATURE                Location/Qualifiers
source                 1..200
                       mol_type = genomic DNA
                       organism = Pichia kudriavzevii
SEQUENCE: 202
gagaaccaag agatccgttg ttgaaagttt ttcgttttcg tagatttctc tcttgtcgac  60
tatatgttat tccacagttt aggtgttttt gttttcgttc cgctcacgca gtgtagtagt  120
aaatcacagt aatgatcctt ccgcaggttc acctacggaa accttgttac gacttttact  180
tcctctaaat gaccaagccg                                              200

SEQ ID NO: 203         moltype = DNA  length = 200
FEATURE                Location/Qualifiers
source                 1..200
                       mol_type = genomic DNA
                       organism = Kazachstania servazzii
SEQUENCE: 203
gagaaccaag agatccgttg ttgaaagttt taatatttgt tttaatatta caaaaagata  60
aatcttcctg gaattctggt tttgactagt tcataaaatt acaaaattgt ttgtgtttgt  120
cactcctggg ccgccgaagc tgcccaaaga agcatgcaaa gaattataaa aatctccact  180
gtgtgtaata gtgctactga                                              200

SEQ ID NO: 204         moltype = DNA  length = 200
FEATURE                Location/Qualifiers
source                 1..200
                       mol_type = genomic DNA
                       organism = Xeromyces bisporus
SEQUENCE: 204
cggaaccaag agatccgttg ttgaaagttt taaccgattt gtatcgtttc gactcagact  60
gcaattccct tcaaaataaa taagcgttca ggagaaggtc tccggcgccg cctcgtggga  120
cgaggccaac acgccgaagc aacagaggtt cggtagtcac gggtcggagg tagggccccg  180
aagtaagttc gggacccgca                                              200

SEQ ID NO: 205         moltype = DNA  length = 200
FEATURE                Location/Qualifiers
source                 1..200
                       mol_type = genomic DNA
                       organism = Aspergillus sp.
SEQUENCE: 205
gtaggtgaac ctgcggaagg atcattaccg agtgagggcc ctctgggtcc aacctcccac  60
ccgtgtctat cgtaccttgt tgcttcggcg ggcccgccgt ttcgacggcc gccgggggagg  120
ccctgcgccc ccgggcccgc gcccgccgaa gaccccaaca tgaacgctgt tctgaaagta  180
tgcagtctga gttgattatc                                              200

SEQ ID NO: 206         moltype = DNA  length = 200
FEATURE                Location/Qualifiers
source                 1..200
                       mol_type = genomic DNA
                       organism = Xeromyces bisporus
SEQUENCE: 206
cggaaccaag agatccgttg ttgaaagttt taaccgattt gtatcgtttc gactcagact  60
gcaattccct tcaaaataaa caagcgttca ggagaaggtc tccggcgccg cctcgtggga  120
cgaggccaac acgccgaagc aacagaggtt cggtagtcac gggtcggagg tagggccccg  180
aagttgttcg ggacccgcac                                              200

SEQ ID NO: 207         moltype = DNA  length = 200
FEATURE                Location/Qualifiers
source                 1..200
                       mol_type = genomic DNA
                       organism = Saccharomyces cerevisiae
SEQUENCE: 207
cttggtcatt tagaggaagt aaaagtcgta acaaggtttc cgtaggtgaa cctgcggaag  60
gatcattaaa gaaatttaat aattttgaaa atggattttt tttttgtttt ggcaagagca  120
tgagagcttt tactgggcaa gaagacaaga gatggagagt ccagccgggc ctgcgcttaa  180
gtgcgcggtc ttgctaggct                                              200

SEQ ID NO: 208         moltype = DNA  length = 200
FEATURE                Location/Qualifiers
source                 1..200
                       mol_type = genomic DNA
                       organism = Pichia cephalocereana
SEQUENCE: 208
gagaaccaag agatccgttg ttgaaagttt tgttttgtta aaacttactg actggtggta  60
ttacaatttt aggtgtttgg tgcgctcacg catgtgtata agatataaat cacagtaatg  120
atccttccgc aggttcacct acggaaacct tgttacgact tttacttcct ctaaatgacc  180
aagccgtgta gatctcggtg                                              200

SEQ ID NO: 209         moltype = DNA  length = 200
FEATURE                Location/Qualifiers
```

```
source                  1..200
                        mol_type = genomic DNA
                        organism = Kazachstania humilis
SEQUENCE: 209
gagaaccaag agatccgttg ttgaaagttt tgaatatttt ggttactgcg taagcagatt  60
tgatgacatt gtataataga aaatagttgt ttgtgtttgg cgagctgagc ttgcgctcgg  120
cccaagaata agtaattact ccactgtgtg taagaggcgg agcgccaccg cgcagctaag  180
cgcaggcggg ctcccccaat                                              200

SEQ ID NO: 210          moltype = DNA  length = 200
FEATURE                 Location/Qualifiers
source                  1..200
                        mol_type = genomic DNA
                        organism = Saccharomyces cerevisiae
SEQUENCE: 210
cttggtcatt tagaggaagt aaaagtcgta acaaggtttc cgtaggtgaa cctgcggaag  60
gatcattaaa gaaatttaat aattttgaaa atggattttt ttttttgttt tggcaagagc  120
atgagagctt ttactgggca agaagacaag agatggagag tccagccggg cctgcgctta  180
agtgcgcggt cttgctaggc                                              200

SEQ ID NO: 211          moltype = DNA  length = 200
FEATURE                 Location/Qualifiers
source                  1..200
                        mol_type = genomic DNA
                        organism = Saccharomyces paradoxus
SEQUENCE: 211
gagaaccaag agatccgttg ttgaaagttt ttaatatttt aaaatttcca gttacgaaaa  60
ttcttgtttt tgacaaaaat ttaatgaata aataaaattg tttgtgtttg ttacctctgg  120
gccccgattg ctcgaatgcc caaagaaaaa gttgcaaaga taatgaaaac tccacagtgt  180
gttgtattga aacggtttta                                              200

SEQ ID NO: 212          moltype = DNA  length = 200
FEATURE                 Location/Qualifiers
source                  1..200
                        mol_type = genomic DNA
                        organism = Pichia kudriavzevii
SEQUENCE: 212
gagaaccaag agatccgttg ttgaaagttt tgtttgtttt tcgtagattt ctcttgtcga  60
ctatatgcta tattccacat tttaggtgtt gttgttttcg ttccgctcac gcagtgtagt  120
actaaatcac agtaatgatc cttccgcagg ttcacctacg gaaaccttgt tacgactttt  180
acttcctcta aatgaccaag                                              200

SEQ ID NO: 213          moltype = DNA  length = 200
FEATURE                 Location/Qualifiers
source                  1..200
                        mol_type = genomic DNA
                        organism = Kazachstania servazzii
SEQUENCE: 213
gagaaccaag agatccgttg ttgaaagttt taatatttgt tttaatatta caaaaagata  60
aatcttcctg gaattctggt tttgactagt tcataaaatt acaaaattgt ttgtgtttgt  120
cactcctggg ccgccgaagc agcccaaaga attataaaaa tctccactgt gtgtaatagt  180
gctactgagc tacagagacc                                              200

SEQ ID NO: 214          moltype = DNA  length = 200
FEATURE                 Location/Qualifiers
source                  1..200
                        mol_type = genomic DNA
                        organism = Penicillium sp.
SEQUENCE: 214
gtaggtgaac ctgcggaagg atcattaccg agtgcgggcc ctctgggtcc aacctcccat  60
ccgtgtctat ctgtaccctg ttgcttcggc gtggccacgg cccgccggag actaacattt  120
gaacgctgtc tgaagtttgc agtctgagtt tttagttaaa caatcgttaa aactttcaac  180
aacggatctc ttggttccgg                                              200

SEQ ID NO: 215          moltype = DNA  length = 200
FEATURE                 Location/Qualifiers
source                  1..200
                        mol_type = genomic DNA
                        organism = Penicillium sp.
SEQUENCE: 215
gtaggtgaac ctgcggaagg atcattaccg agtgagggcc ctctgggtcc aacctcccac  60
ccgtgtttat tttaccttgt tgcttcggcg ggcccgcctt aactggccgc cggggggctc  120
acgcccccgg gcccgcgccc gccgaagaca ccctcgaact ctgtctgaag attgaagtct  180
gagtgaaaat ataaattatt                                              200

SEQ ID NO: 216          moltype = DNA  length = 200
FEATURE                 Location/Qualifiers
source                  1..200
                        mol_type = genomic DNA
```

```
                          organism = Aspergillus intermedius
SEQUENCE: 216
cggaaccaag agatccgttg ttgaaagttt taacgattgt ttaactaaaa actcagactg  60
caaacttcag acagcgttca aatgttagtc tccggcgggc cgtggccacg ccgaagcaac  120
agggtacaga tagacacgga tgggaggttg gacccagagg gcccgcactc ggtaatgatc  180
cttccgcagg ttcacctacg                                              200

SEQ ID NO: 217            moltype = DNA  length = 200
FEATURE                   Location/Qualifiers
source                    1..200
                          mol_type = genomic DNA
                          organism = Pichia kudriavzevii
SEQUENCE: 217
gagaaccaag agatccgttg ttgaaagttt tgtttgtttt ttcgtagatt tctcttgtcg  60
actatatgct atattccaca ttttaggtgt tgttgttttc gttccgctca cgcagtgtag  120
tagtaaatca cagtaatgat ccttccgcag gttcacctac ggaaaccttg ttacgacttt  180
tacttcctct aaatgaccaa                                              200

SEQ ID NO: 218            moltype = DNA  length = 200
FEATURE                   Location/Qualifiers
source                    1..200
                          mol_type = genomic DNA
                          organism = Penicillium sp.
SEQUENCE: 218
gtaggtgaac ctgcggaagg atcattaccg agtgcgggcc ctctgggtcc aacctcccat  60
ccgtgtctat ctgtaccctg ttgcttcggc gtggccacgg cccgccgaag actaacattt  120
gaacactgtc tgaagtttgc agtctgagtt tttagttaaa caataattaa aactttcaac  180
aacggatctc ttggttccgg                                              200

SEQ ID NO: 219            moltype = DNA  length = 200
FEATURE                   Location/Qualifiers
source                    1..200
                          mol_type = genomic DNA
                          organism = Candida glabrata
SEQUENCE: 219
gagaaccaag agatccattg ttgaaagttt tgaagttgtt ttctactaaa agaaatcttg  60
tgttgactga attattttaa aaaaatattt gtttgtgttt gcatccactg ggagaactcc  120
cccccgaaag agagcgttcc cccaacgaac aaaagaatag tagtaaagta aactccactg  180
tgtgtagtaa ttagaaagtg                                              200

SEQ ID NO: 220            moltype = DNA  length = 200
FEATURE                   Location/Qualifiers
source                    1..200
                          mol_type = genomic DNA
                          organism = Penicillium tarraconense
SEQUENCE: 220
gtaggtgaac ctgcggaagg atcattaccg agtgagggcc ctctgggtcc aacctcccac  60
ccgtgtttat tttaccttgt tgcttcggcg ggcccgcctt tactggccgc cggggggctc  120
acgctcccgg gcccgcgccc gccgaagaca cccccgaact ctgtctgaag attgcagtct  180
gagtgaaaac gaaattattt                                              200

SEQ ID NO: 221            moltype = DNA  length = 200
FEATURE                   Location/Qualifiers
source                    1..200
                          mol_type = genomic DNA
                          organism = Penicillium sp.
SEQUENCE: 221
gtaggtgaac ctgcggaagg atcattaccg agtgagggcc ctctgggtcc aacctcccac  60
ccgtgtttat ttaccttatt gcttcggcgg gcccgcctta actggccgcc ggggggttta  120
cacccccggg cccgcgcccg ccgaagacac cccgaactct gtctgaagaa tgcagtctga  180
gaacaaatat aaattattta                                              200

SEQ ID NO: 222            moltype = DNA  length = 200
FEATURE                   Location/Qualifiers
source                    1..200
                          mol_type = genomic DNA
                          organism = Candida parapsilosis
SEQUENCE: 222
gagaaccaag agatccgttg ttgaaagttt tgactattaa ataatcggtt gacattaaat  60
aaaatttggt tgagtttaat ctctggcagg ccccatatag aaggcctacc aaagcaaagt  120
tttcaaaaaa agaaaaacac atgtgtaaga aaaaatgcag ttaagcactt ttcattctgt  180
aatgatcctt ccgcaggttc                                              200

SEQ ID NO: 223            moltype = DNA  length = 200
FEATURE                   Location/Qualifiers
source                    1..200
                          mol_type = genomic DNA
                          organism = Candida glabrata
SEQUENCE: 223
```

```
gagaaccaag agatccattg ttgaaagttt tgaagttgtt ttctactaaa agaaatcttg  60
tgttgactga attagtttaa aaaaatattt gtttgtgttt gcatccactg ggagaactcc  120
cccccgaaag agagcgttcc cccaacgaac aaaagaatag taaagtaaac tccactgtgt  180
gtagtaatta gaaagtgtcg                                              200

SEQ ID NO: 224         moltype = DNA  length = 200
FEATURE                Location/Qualifiers
source                 1..200
                       mol_type = genomic DNA
                       organism = Aspergillus sp.
SEQUENCE: 224
cggaaccaag agatccgttg ttgaaagttt taacgatttt ttatatcggt actcagactg  60
caaccttcag acagtgttca tggttgaggt ctccggcggg cacgggcccg ggggcaggga  120
agccccccgg cggccacgaa gggcgggccc gccgaagcaa cagggtacaa atagacacgg  180
atgggaggac ggacaccccg                                              200

SEQ ID NO: 225         moltype = DNA  length = 200
FEATURE                Location/Qualifiers
source                 1..200
                       mol_type = genomic DNA
                       organism = Nakazawaea holstii
SEQUENCE: 225
gtaggtgaac ctgcggaagg atcattacag tattctattg ccagcgctta attgcgcggc  60
gataaacctt acacactttg tttttattat taaagacacc attgctttgg tggatgagtg  120
taaaagcttg tccgccagag gttaactaaa ctcaattatt taaaggtaac tttttaaatt  180
gtcaataata atttgtctga                                              200

SEQ ID NO: 226         moltype = DNA  length = 200
FEATURE                Location/Qualifiers
source                 1..200
                       mol_type = genomic DNA
                       organism = Aspergillus sp.
SEQUENCE: 226
cggaaccaag agatccgttg ttgaaagttt taattattgt ttaactaaaa actcagactg  60
caaacttcag acagtgttca aatgttagtc ttcggcgggc cgtggccacg ccgaagcaac  120
agggtacaga tagacacgga tgggaggttg gacccagagg gcccgcactc ggtaatgatc  180
cttccgcagg ttcacctacg                                              200

SEQ ID NO: 227         moltype = DNA  length = 200
FEATURE                Location/Qualifiers
source                 1..200
                       mol_type = genomic DNA
                       organism = Phaeococcomyces sp.
SEQUENCE: 227
gtaggtgaac ctgcggaagg atcattactg agactgggtg cttcggcgcc cgacctccaa  60
ccccctgtct accttaccac tgttgcctcg gcgtctccgt ccgcctcctc ctcgcggggg  120
ggtgcggggg ggtgcgccgg cggccaaaac aacgaaaccc ttcttcaaac caagcaatct  180
gagaaattat tttaataact                                              200

SEQ ID NO: 228         moltype = DNA  length = 200
FEATURE                Location/Qualifiers
source                 1..200
                       mol_type = genomic DNA
                       organism = Pichia kudriavzevii
SEQUENCE: 228
gagaaccaag agatccgttg ttgaaagttt tgtttgtttt ttcgtagatt tctcttgtcg  60
actatatgct atattccaca ttttaggtgt tgttgttttc gttccgctca cgcagtgtag  120
tactaaatca cagtaatgat ccttccgcag gttcacctac ggaaaccttg ttacgacttt  180
tacttcctct aaatgaccaa                                              200

SEQ ID NO: 229         moltype = DNA  length = 200
FEATURE                Location/Qualifiers
source                 1..200
                       mol_type = genomic DNA
                       organism = Debaryomyces sp.
SEQUENCE: 229
gtaggtgaac ctgcggaagg atcattacag tattcttttt gccagcgctt aattgcgcgg  60
cgaaaaaacc ttacacacag tgttttttgt tattacaaga acttttgctt tggtctggac  120
tagaaatagt ttgggccaga ggttactgaa ctaaacttca atatttatat tgaattgtta  180
tttatttaat tgtcaatttg                                              200

SEQ ID NO: 230         moltype = DNA  length = 200
FEATURE                Location/Qualifiers
source                 1..200
                       mol_type = genomic DNA
                       organism = Cephaloascus albidus
SEQUENCE: 230
gtaggtgaac ctgcggaagg atcattacag tattcttttg ccagcgctta attgcgcggc  60
gaaaaacctt acacacagtg ctttttgtta ttacaagaac tattgctttg gcttggccta  120
```

```
gagataggtt gggccagagg tttaactgaa cttcgaaatt tattttgaat tgtttctaat  180
atttaatttg tcaatttgtt                                              200

SEQ ID NO: 231         moltype = DNA  length = 200
FEATURE                Location/Qualifiers
source                 1..200
                       mol_type = genomic DNA
                       organism = Pichia kudriavzevii
SEQUENCE: 231
gagaaccaag agatccgttg ttgaaagttt tgtttgtttt tcgtagattt ctcttgtcga  60
ctatatgcta tattccacat tttaggtgtt tttgttttcg ttccgctcac gcagtgtaat  120
actaaatcac agtaatgatc cttccgcagg ttcacctacg gaaaccttgt tacgactttt  180
acttcctcta aatgaccaag                                              200

SEQ ID NO: 232         moltype = DNA  length = 200
FEATURE                Location/Qualifiers
source                 1..200
                       mol_type = genomic DNA
                       organism = Saccharomyces cerevisiae
SEQUENCE: 232
cttggtcatt tagaggaagt aaaagtcgta acaaggtttc cgtaggtgaa cctgcggaag  60
gatcattaaa gaaatttaat aattttgaaa atggattttt ttgttttggc aagagcatga  120
gagcttttac tgggcaagaa gacaagagat ggagagtcca gccgggcctg cgcttaagtg  180
cgcggtcttg ctaggcttgt                                              200

SEQ ID NO: 233         moltype = DNA  length = 200
FEATURE                Location/Qualifiers
source                 1..200
                       mol_type = genomic DNA
                       organism = Saccharomyces cerevisiae
SEQUENCE: 233
cttggtcatt tagaggaagt aaaagtcgta acaaggtttc cgtaggtgaa cctgcggaag  60
gatcattaaa gaaatttaat aattttgaaa atggattttt tttttttgtt ttggcaagag  120
catgagagct tttactgggc aagaagacaa gagatggaga gtccagccgg gcctgcgctt  180
aagtgcgcgg tcttgctagg                                              200

SEQ ID NO: 234         moltype = DNA  length = 200
FEATURE                Location/Qualifiers
source                 1..200
                       mol_type = genomic DNA
                       organism = Aspergillus sp.
SEQUENCE: 234
cggaaccaag agatccgttg ttgaaagttt taacgatttt ttgtatcggt actcagactg  60
caaccttcag acagtgttca tggttgaggt ctccggcggg cacgggcccg ggggcaggga  120
agccccccgg cggccacgaa gggcgggccc gccgaagcaa cagggtacaa atagacacgg  180
atgggaggac ggacaccccg                                              200

SEQ ID NO: 235         moltype = DNA  length = 200
FEATURE                Location/Qualifiers
source                 1..200
                       mol_type = genomic DNA
                       organism = Saccharomyces cerevisiae
SEQUENCE: 235
cttggtcatt tagaggaagt aaaagtcgta acaaggtttc cgtaggtgaa cctgcggaag  60
gatcattaaa gaaatttaat aattttgaaa atggattttt ttttgttttg gcaagagcat  120
gagagctttt actgggcaag aagacaagag atggagagtc cagccgggcc tgcgcttaag  180
tgcgcggtct tgctaggctt                                              200

SEQ ID NO: 236         moltype = DNA  length = 200
FEATURE                Location/Qualifiers
source                 1..200
                       mol_type = genomic DNA
                       organism = Penicillium sp.
SEQUENCE: 236
gtaggtgaac ctgcggaagg atcattaccg agtgagggcc ctctgggtcc aacctcccac  60
ccgtgtttat tttaccttgt tgcttcggcg ggcccgcctt tactggccgc cggggggctc  120
acgcccccgg gcccgcgccc gccgaagaca ccctcgaact ctgtctgaag attgaagtct  180
gagtgaaaat ataaattatt                                              200

SEQ ID NO: 237         moltype = DNA  length = 200
FEATURE                Location/Qualifiers
source                 1..200
                       mol_type = genomic DNA
                       organism = Eremothecium coryli
SEQUENCE: 237
gagaaccaag agatccattg ttgaaagttt tgaatatttt atttcttatg aaatagaatt  60
gactagtttt caaaattttt gtttgtgttt atccctgggc agttagagcc caggaagaat  120
agcatatagt agaaactaca cgtgtgttgg ttagatagac tgttaacaga tgttcaatac  180
cgccgcgcaa ctaagcgcag                                              200
```

```
SEQ ID NO: 238          moltype = DNA  length = 200
FEATURE                 Location/Qualifiers
source                  1..200
                        mol_type = genomic DNA
                        organism = Hanseniaspora mollemarum
SEQUENCE: 238
gagaaccaag agatccgttg ttgaaagttt taaattattt aaaatttccg ttaggaattt  60
tggtttagct taaaaaatta taataaaaat attgtttgtg tttgttttaa ctctgggcct  120
tgcgacccaa agtagaaaga attaagtaga aaactccact gtgtgtagta gttgactgag  180
attcaattaa aaattacttc                                              200

SEQ ID NO: 239          moltype = DNA  length = 200
FEATURE                 Location/Qualifiers
source                  1..200
                        mol_type = genomic DNA
                        organism = Cyberlindnera fabianii
SEQUENCE: 239
gagaaccaag agatccgttg ttgaaagttt tgaagatttg tttttaataa aacttcttga  60
ctagaatttg taataaaaga tataaaaatc ttgtgttttg ataacctctg cgcagaaaag  120
ctaggcttat tccacgcaaa gcaatgttag aaaaaactaa gcactgtgtg taaggtttta  180
gtcgccgcgc tagttaaagc                                              200

SEQ ID NO: 240          moltype = DNA  length = 200
FEATURE                 Location/Qualifiers
source                  1..200
                        mol_type = genomic DNA
                        organism = Kazachstania humilis
SEQUENCE: 240
gagaaccaag agatccgttg ttgaaagttt tgaatatttt ggttactgcg taagcagatt  60
tgatgacgtt gtataataga aaatagttgt ttgtgtttgg cgagctgagc ttgcgctcgg  120
cccaagaata agtaattact ccactgtgtg taagaggcgg agcgccaccg cgcagctaag  180
cgcaggcggg ctccccccaat                                              200

SEQ ID NO: 241          moltype = DNA  length = 200
FEATURE                 Location/Qualifiers
source                  1..200
                        mol_type = genomic DNA
                        organism = Saccharomyces paradoxus
SEQUENCE: 241
gagaaccaag agatccgttg ttgaaagttt ttaatattct aaaatttcca gttacgaaaa  60
ttcttgtttt tgacaaaaat ttaatgaata aataaaattg tttgtgtttg ttacctctgg  120
gccccgattg ctcgaatgcc caaagaaaaa gttgcaaaga tatgaaaact ccacagtgtg  180
ttgtattgaa acggttttaa                                              200

SEQ ID NO: 242          moltype = DNA  length = 200
FEATURE                 Location/Qualifiers
source                  1..200
                        mol_type = genomic DNA
                        organism = Saccharomyces cerevisiae
SEQUENCE: 242
catggtcatt tagaggaagt aaaagtcgta acaaggtttc cgtaggtgaa cctgcggaag  60
gatcattaaa gaaatttaat aattttgaaa atggattttt ttgttttggc aagagcatga  120
gagcttttac tgggcaagaa gacaagagat ggagagtcca gccgggcctg cgcttaagtg  180
cgcggtcttg ctaggcctgt                                              200

SEQ ID NO: 243          moltype = DNA  length = 200
FEATURE                 Location/Qualifiers
source                  1..200
                        mol_type = genomic DNA
                        organism = Saccharomycetales sp.
SEQUENCE: 243
gagaaccaag agatccgttg ttgaaagttt tgaagatttt tgaatttaat caacaaattg  60
actatggtta aaataacaat tcaataaaaa tattgaagtt taataaatct ttggcccaac  120
ttgcgccaga ccaaagcaat gttttcaaag aaaagaaaat cactgtgtgt aaggtttttc  180
gccgcgcagt taagcgctgg                                              200

SEQ ID NO: 244          moltype = DNA  length = 200
FEATURE                 Location/Qualifiers
source                  1..200
                        mol_type = genomic DNA
                        organism = Saccharomyces sp.
SEQUENCE: 244
gagaaccaag agatccgttg ttgaaagttt ttaatatttt aaaatttcca gttacgaaaa  60
ttcttgtttt ttgacaaaaa tttaatgaat agataaaatt gtttgtgttt gttacctctg  120
ggccccgatt gctcgaatgc ccaaagaaaa agttgcaaag atatgaaaac tccacagtgt  180
gttgtattga aacggtttta                                              200

SEQ ID NO: 245          moltype = DNA  length = 200
```

```
FEATURE                Location/Qualifiers
source                 1..200
                       mol_type = genomic DNA
                       organism = Penicillium sp.
SEQUENCE: 245
gtaggtgaac ctgcggaagg atcattaccg agtgtagggt tcctagcgag cccaacctcc  60
cacccgtgtt tactgtacct tagttgcttc ggcgggcccg ccattcatgg ccgccggggg  120
ctctcagccc cgggcccgcg cccgccggag acaccacgaa ctctgtctga tctagtgaag  180
tctgagttga ttgtatcgca                                              200

SEQ ID NO: 246         moltype = DNA  length = 200
FEATURE                Location/Qualifiers
source                 1..200
                       mol_type = genomic DNA
                       organism = Saccharomyces pastorianus
SEQUENCE: 246
gagaaccaag agatccgttg ttgaaagttt ttaatatttt aaaatttcca gttacgaaaa  60
ttcttgtttt ttgacaaaaa tttaatgaat aaataaaatt gtttgtgttt gttacctctg  120
ggctcgattg ctcgaagccc aaagaaaaag ttgcaaaagt ataaaaactc cacagtgtgt  180
tgtattgaaa cggttttaat                                              200

SEQ ID NO: 247         moltype = DNA  length = 200
FEATURE                Location/Qualifiers
source                 1..200
                       mol_type = genomic DNA
                       organism = Saccharomyces paradoxus
SEQUENCE: 247
gagaaccaag agatccgttg ttgaaagttt ttaatatttt aaaatttcca gttacgaaaa  60
ttcttgtttt tgacaaaaat ttaatgaata aataaaattg tttgtgtttg ttacctctgg  120
gccccgattg ctcgaatgcc caaagaaaaa gttgcaaaga tatgaaaact ccacggtgtg  180
ttgtattgaa acggttttaa                                              200

SEQ ID NO: 248         moltype = DNA  length = 200
FEATURE                Location/Qualifiers
source                 1..200
                       mol_type = genomic DNA
                       organism = Candida sp.
SEQUENCE: 248
gagaaccaag agatccgttg ttgaaagttt tgaagatttt tgaatttaat caacaaattg  60
acaataaatt aaaataacaa ttcaatataa atattgaagt ttggtgtaaa cctttggccc  120
aacttatttc taagacagac caaagcaaga gtttcaaatt agaaaaacat agtgtgtaag  180
gtttttcgcc gcgcaattaa                                              200

SEQ ID NO: 249         moltype = DNA  length = 200
FEATURE                Location/Qualifiers
source                 1..200
                       mol_type = genomic DNA
                       organism = Wickerhamomyces anomalus
SEQUENCE: 249
gagaaccaag agatccgttg ttgaaagttt tgaagatttt aatttttgtt aaaaattttc  60
atgactattg gttaaaggtt ttaacattaa aaaaatgtgt ttagaccttt gggcagtaag  120
ccaggctcac cacccaaagc aaagttcaaa aaaaactaga caatgtgtgt aaggtttatc  180
gccgcgcaat taagcgctgg                                              200

SEQ ID NO: 250         moltype = DNA  length = 200
FEATURE                Location/Qualifiers
source                 1..200
                       mol_type = genomic DNA
                       organism = Aspergillus penicillioides
SEQUENCE: 250
cggaaccaag agatccgttg ttgaaagttt taacaatttt tctttatgaa aactcagact  60
gcaaccttca gacagtgttc agtgttggtg tccccggcgg gcacgggccc gggggcaggg  120
tagccccccg gcggccggcg ccccccagga gggggcagcc agcgggcccg ccgaagcaac  180
agggtatgaa tagacacgga                                              200

SEQ ID NO: 251         moltype = DNA  length = 200
FEATURE                Location/Qualifiers
source                 1..200
                       mol_type = genomic DNA
                       organism = Candida sake
SEQUENCE: 251
gagaaccaag agatccgttg ttgaaagttt tgatattttt atcgtttgac taaactaaat  60
tattagtgtt cttgcaagca agttctctaa aaaaacatgt gtaatgcaat taagcaaact  120
ttaatgatcc ttccgcaggt tcacctacgg aaaccttgtt acgactttta cttcctctaa  180
atgaccaagc cgtgtagatc                                              200

SEQ ID NO: 252         moltype = DNA  length = 200
FEATURE                Location/Qualifiers
source                 1..200
```

```
                        mol_type = genomic DNA
                        organism = Pichia norvegensis
SEQUENCE: 252
gagaaccaag agatccgttg ttgaaagttt tatgtttcta gatttctggt gacgggggta  60
cttcatgttt aggtgttgtg tgcgctcacg cgtgtggaca aaataatcac agtaatgatc  120
cttccgcagg ttcacctacg gaaaccttgt tacgactttt acttcctcta aatgaccaag  180
ccgtgtagat ctcggtggtc                                              200

SEQ ID NO: 253          moltype = DNA  length = 200
FEATURE                 Location/Qualifiers
source                  1..200
                        mol_type = genomic DNA
                        organism = Saccharomyces paradoxus
SEQUENCE: 253
gagaaccaag agatccgttg ttgaaagttt ttaatatttt aaaatttcca gttacgaaaa  60
ttcttttgtt tttgacaaaa atttaatgaa taaataaaat tgtttgtgtt tgttacctct  120
gggccccgat tgctcgaatg cccaaagaaa aagttgcaaa gatatgaaaa ctccacagtg  180
tgttgtattg aaacggtttt                                              200

SEQ ID NO: 254          moltype = DNA  length = 200
FEATURE                 Location/Qualifiers
source                  1..200
                        mol_type = genomic DNA
                        organism = Aspergillus sp.
SEQUENCE: 254
cggaaccaag agatccgttg ttgaaagttt taacgatttt ctatatcggt actcagactg  60
caaccttcag acagtgttca tggttgaggt ctccggcggg cacgggcccg ggggcaggga  120
agccccccgg cggccacgaa gggcgggccc gccgaagcaa cagggtacaa atagacacgg  180
atgggaggac ggacaccccg                                              200

SEQ ID NO: 255          moltype = DNA  length = 200
FEATURE                 Location/Qualifiers
source                  1..200
                        mol_type = genomic DNA
                        organism = Candida sake
SEQUENCE: 255
cttggtcatt tagaggaagt aaaagtcgta acaaggtttc cgtaggtgaa cctgcggaag  60
gatcattaaa gtttgcttaa ttgcattaca catgtttttt tagagaactt gcttgcaaga  120
acactaataa tttacttagt caacaaataa aaatatcaaa actttcaaca acggatctct  180
tggttctcgc atcgatgaag                                              200

SEQ ID NO: 256          moltype = DNA  length = 200
FEATURE                 Location/Qualifiers
source                  1..200
                        mol_type = genomic DNA
                        organism = Candida sp.
SEQUENCE: 256
catggtcatt tagaggaagt aaaagtcgta acaaggtttc cgtaggtgaa cctgcggaag  60
gatcattata gtatcttgct gcctgcgctt aactgcgcgg cggtacacct ttacacactt  120
gtttatcagt gctattgctt tgtcgtttta tgcggcagag attacaaact cctaagtttt  180
actacttatt ttaacctagt                                              200

SEQ ID NO: 257          moltype = DNA  length = 200
FEATURE                 Location/Qualifiers
source                  1..200
                        mol_type = genomic DNA
                        organism = Kazachstania sp.
SEQUENCE: 257
gagaaccaag agatccgttg ttgaaagttt tgaatatttt ggttactgca ataaagcaga  60
tttttaaatg acaaattaaa aataataaaa ataattgttt gtgttttgtg ttgaaggtat  120
tgctaccctc gatactgtag aaataaaact ccagtgtgtg taagaattat cggcgtagcg  180
aaaagaacaa cctcaccgcg                                              200

SEQ ID NO: 258          moltype = DNA  length = 200
FEATURE                 Location/Qualifiers
source                  1..200
                        mol_type = genomic DNA
                        organism = Pichia cephalocereana
SEQUENCE: 258
gagaaccaag agatccgttg ttgaaagttt tgttttgtta aaacttagtg actggtagta  60
ttacaatttt aggtgtttgg tgcgctcacg catgtgtata agatataaat cacagtaatg  120
atccttccgc aggttcacct acggaaacct tgttacgact tttacttcct ctaaatgacc  180
aagccgtgta gatctcggtg                                              200

SEQ ID NO: 259          moltype = DNA  length = 200
FEATURE                 Location/Qualifiers
source                  1..200
                        mol_type = genomic DNA
                        organism = Saccharomyces paradoxus
```

```
SEQUENCE: 259
gagaaccaag agatccgttg ttgaaagttt ttaattattt ttaaaatttc cagttacgaa  60
aattcttgtt tttgacaaaa atttaatgaa taaataaaat tgtttgtgtt tgttacctct  120
gggccccgat tgctcgaatg cccaaagaaa aagttgcaaa gatatgaaaa ctccacagtg  180
tgttgtattg aaacggtttt                                              200

SEQ ID NO: 260         moltype = DNA  length = 200
FEATURE                Location/Qualifiers
source                 1..200
                       mol_type = genomic DNA
                       organism = Candida sake
SEQUENCE: 260
catggtcatt tagaggaagt aaaagtcgta acaaggtttc cgtaggtgaa cctgcggaag  60
gatcattaaa gtttgcttaa ttgcattaca catgtttttt tagagaactt gcttgcaaga  120
acactaataa tttacttagt caacaaataa aaatatcaaa actttcaaca acggatctct  180
tggttctcgc atcgatgaag                                              200

SEQ ID NO: 261         moltype = DNA  length = 200
FEATURE                Location/Qualifiers
source                 1..200
                       mol_type = genomic DNA
                       organism = Pichia kudriavzevii
SEQUENCE: 261
gagaaccaag agatccgttg ttgaaagttt tgtttgtttt tcgtagattt ctcttgtcga  60
ctatgctata ttccacattt taggtgtttt tgttttcgtt ccgctcacgc agtgtagtac  120
taaatcacag taatgatcct tccgcaggtt cacctacgga aaccttgtta cgacttttac  180
ttcctctaaa tgaccaagcc                                              200

SEQ ID NO: 262         moltype = DNA  length = 200
FEATURE                Location/Qualifiers
source                 1..200
                       mol_type = genomic DNA
                       organism = Kazachstania humilis
SEQUENCE: 262
gagaaccaag agatccgttg ttgaaagttt tgaatatttt ggttactgcg taagcagatt  60
tgatgacgtt gtataataga aaatagttgt ttgtgtttgg cgagatggac tttcgtccac  120
cccaagaata agtaattact ccactgtgtg taagaggcgg agcgccaccg cgcagctaag  180
cgcaggcggg ctcccccaat                                              200

SEQ ID NO: 263         moltype = DNA  length = 200
FEATURE                Location/Qualifiers
source                 1..200
                       mol_type = genomic DNA
                       organism = Penicillium sp.
SEQUENCE: 263
gtaggtgaac ctgcggaagg atcattaccg agtgcgggcc ctctgggtcc aacctcccat  60
ccgtgtctat tcataccctg ttgcttcggc gggcccgctg gctgcccccct cctgggggc  120
gccggccgcc ggggggctac cctgcccccg ggcccgtgcc cgccggggac accaacactg  180
aacactgtct gaaggttgca                                              200

SEQ ID NO: 264         moltype = DNA  length = 200
FEATURE                Location/Qualifiers
source                 1..200
                       mol_type = genomic DNA
                       organism = Wickerhamomyces anomalus
SEQUENCE: 264
gagaaccaag agatccgttg ttgaaagttt tgaagatttt aatttttgtt aaaaattttc  60
atgactaatg gttaaaggtt ttaacattaa aaaaatgtgt ttagaccttt gggcacgcag  120
ctaggctgat gcacccaaag caaagttcaa aaaaactaga caatgtgtgt aaggtttatc  180
gccgcgcaat taagcgctgg                                              200

SEQ ID NO: 265         moltype = DNA  length = 200
FEATURE                Location/Qualifiers
source                 1..200
                       mol_type = genomic DNA
                       organism = Penicillium sp.
SEQUENCE: 265
gtaggtgaac ctgcggaagg atcattaccg agtgagggcc ctttgggtcc aacctcccac  60
ccgtgtttat tttaccttgt tgcttcggcg ggcccgcctt tactggccgc cggggggctc  120
acgcccccgg gtccgcgccc gccgaagaca ccctcgaact ctgtctgaag attgaagtct  180
gagtgaaaat ataaattatt                                              200

SEQ ID NO: 266         moltype = DNA  length = 200
FEATURE                Location/Qualifiers
source                 1..200
                       mol_type = genomic DNA
                       organism = Penicillium sp.
SEQUENCE: 266
gtaggtgaac ctgcggaagg atcattaccg agtgagggcc ctttgggtcc aacctcccac  60
```

```
ccgtgtttat tttaccttgt tgcttcggcg ggcccgcctt tactggccgc cggggggctt  120
cacgcccccg ggcccgcgcc cgccgaagac accctcgaac tctgtctgaa gattgaagtc  180
tgagtgaaaa tataaattat                                              200

SEQ ID NO: 267         moltype = DNA  length = 570
FEATURE                Location/Qualifiers
source                 1..570
                       mol_type = genomic DNA
                       organism = Saccharomyces cerevisiae
SEQUENCE: 267
ggattttttt tttgttttgg caagagcatg agagctttta ctgggcaaga agacaagaga  60
tggagagtcc agccgggcct gcgcttaagt gcgcggtctt gctaggcttg taagtttctt  120
tcttgctatt ccaaacggtg agagatttct gtgcttttgt tataggacaa ttaaaaccgt  180
ttcaatacaa cacactgtgg agttttcata tctttgcaac tttttctttg ggcattcgag  240
caatcggggc ccagaggtaa caaacacaaa caattttatc tattcattaa atttttgtca  300
aaaacaagaa ttttcgtaac tggaaatttt aaaatattaa aaactttcaa caacggatct  360
cttggttctc gcatcgatga agaacgcagc gaaatgcgat acgtaatgtg aattgcagaa  420
ttccgtgaat catcgaatct ttgaacgcac attgcgcccc ttggtattcc agggggcatg  480
cctgtttgag cgtcatttcc ttctcaaaca ttctgtttgg tagtgagtga tactctttgg  540
agttaacttg aaattgctgg ccttttcatt                                   570

SEQ ID NO: 268         moltype = DNA  length = 569
FEATURE                Location/Qualifiers
source                 1..569
                       mol_type = genomic DNA
                       organism = Kazachstania humilis
SEQUENCE: 268
gctgcgcggt ggcgctccgc ctcttacaca cagtggagta attatttatt cttgggctgg  60
gcgaaagctc agctcgccaa acacaaacaa ctattttcta ttatacaacg tcatcaaatc  120
tgcttacgca gtaaccaaaa tattcaaaac tttcaacaac ggatctcttg gttctcgcat  180
cgatgaagaa cgcagcgaaa tgcgatacgt aatgtgaatt gcagaattcc gtgaatcatc  240
gaatctttga acgcacattg cgccccttgg tattccaggg ggcatgcctg tttgagcgtc  300
atttccttct caagcacctg tgcttggttg tgggtgacac tctctcgagt tagcttgaaa  360
ttgctggccg cactgcggtg gagcagttgg cttgtctgtc gtgcgcggtg cctcggcgcc  420
gggcgtggct ggcatgcgat tgtcgtacta ggttttacca attcggcagg agcgtgctgg  480
gcagagagac aatacaaccg ccctccctct ggctaacagt actctttaag tttgacctca  540
aatcaggtag gaatacccgc tgaacttaa                                    569

SEQ ID NO: 269         moltype = DNA  length = 200
FEATURE                Location/Qualifiers
source                 1..200
                       mol_type = genomic DNA
                       organism = Kazachstania humilis
SEQUENCE: 269
attgggggag cctgcctgcg cttagctgcg cggtggcgct ccgcctctta cacacagtgg  60
agtaattatt tattcttggg ctgggcgaaa gctcagctcg ccaaacacaa acaactattt  120
tctattatac aacgtcatca aatctgctta cgcagtaacc aaaatattca aaactttcaa  180
caacggatct cttggttctc                                              200

SEQ ID NO: 270         moltype = DNA  length = 1264
FEATURE                Location/Qualifiers
source                 1..1264
                       mol_type = genomic DNA
                       organism = Fructilactobacillus sanfranciscensis
SEQUENCE: 270
tgggcaaggg tttttgcgtg cgaacgccgg aacgcggacg cggattcttg ctgcttgcac  60
taggatgatt ttggatccga ctgagtggcg aactggtgag taacacgtgg gtaacctgcc  120
cagaagaagg ggataacacc tggaaacaga tgctaatacc gtataacaac aagaaccaca  180
tggttcttgt ttgaaagctg gcctttgtgc tagtgcttct ggatggaccc gcggcgtatt  240
agctagttgg tgagataata gctcaccaag gcaatgatac gtagcagacc tgagagggta  300
atctgccaca atgggactga gacacggccc atactcctac gggaggcagc agtagggaat  360
cttccacaat ggacgaaagt ctgatggagc aacgccgcgt gagtgaagaa gggtttcggc  420
tcgtaaaact ctgttgttag agaagaacag ccgtgagagc aactgctcac ggtatgacgg  480
tatctaacca gaaagtcacg gctaactacg tgccgcagcc gcggtaatac gtaggtggca  540
aacgttgtcc ggatttattg ggcgtaaagg gagcgcaggc ggtttattaa gtctgatgtg  600
aaagccttcg gcttaaccgg agaagtgcat cggaaactga taaacttgag tgcagaaaag  660
gatagtggaa cttcatgtgt agcggtgaaa tgcgtagata tatgaaggaa caccagtggc  720
gaaggcggct atctggtctg taactgacgc tgaggctcga aagcatgggt agcaaacagg  780
attagatacc ctggtagtcc atgccgtaac gatgaatgct aggtgttgga aggtttccgc  840
ctttcagtgc cgcagctaac gcattaagca ttccgcctgg ggagtacgac cgcaaggttg  900
aaactcaagg aattgacggg gacccgcaca agcggtggag catgtggttt aattcgatgc  960
tacgcgagaa ccctaccagg acttgacatc ttctgccaat ctaagagatt agacgttccc  1020
ttcggggaca gaatgacagt ggtgcatggt tgtcgtcagc tcgtgtcatg aaatgttggg  1080
ttaagtcccg caacgagcgc aacccttgtc ttagtgccag catagtnggc actcttagag  1140
agactgcgtg ataacgagaa gttgggatga cgtcaatcat catggccnat gtctnnncac  1200
acnntgntaa tnnnatacac ganntgccan cgcanncagc tatctcgtaa gtcttctctc  1260
gatt                                                               1264

SEQ ID NO: 271         moltype = DNA  length = 1173
```

-continued

```
FEATURE                 Location/Qualifiers
source                  1..1173
                        mol_type = genomic DNA
                        organism = Pediococcus pentosaceus
SEQUENCE: 271
ngnttgagct atacatgcaa gtcgaacgaa cttccgttaa ttgattatga cgtacttgta  60
ctgattgaga ttttaacacg aagtgagtgg cgaacgggtg agtaacacgt gggtaacctg  120
cccagaagta ggggataaca cctggaaaca gatgctaata ccgtataaca gagaaaaccg  180
catggttttc ttttaaaaga tggctctgct atcacttctg gatggacccc ggcgtattag  240
ctagttggtg aggtaaaggc tcaccaaggc agtgatacgt agccgacctg agagggtaat  300
cggccacatt gggactgaga cacggcccag actcctacgg gaggcagcag tagggaatct  360
tccacaatgg acgcaagtct gatggagcaa cgccgcgtga gtgaagaagg gtttcggctc  420
gtaaagctct gttgttaaag aagaacgtgg gtaagagtaa ctgtttaccc agtgacggta  480
tttaaccaga aagccacggc taactacgtg ccagcagccg cggtaatacg taggtggcaa  540
gcgttatccg gatttattgg gcgtaaagcg agcgcaggcg gtcttttaag tctaatgtga  600
aagccttcgg ctcaaccgaa gaagtgcatt ggaaactggg agacttgagt gcagaagagg  660
acagtggaac tccatgtgta gcggtgaaat gcgtagatat atggaagaac accagtggcg  720
aaagcggctg tctggtctgc aactgacgct gagctcgaaa gcatggtagc gaacaggatt  780
agataccctg gtagtccatg ccgtaacgat gattactagt gttgggaggg tttccgccct  840
tcagtgctgc agctacgcat tagtaatccg cctggggagt acgaccgcag ttgaaactca  900
aaggattgac ggggccgcac agcgtgagca tgtgtttatt cgagctacgc gagacttaca  960
gtctgacatc ttctgacagt ctagagataa agtccnnngg acgaatgann nggtgcatgn  1020
tgtcncactc tgtcctgaag ttggtanccc cacnnccaac ttttactatt gcacattant  1080
tgnactctat ggaactgcgg gcaacnagag nngnacactc tnnatctcat gcnnactggt  1140
ctanaccgtc tccatgatgg tacacagatt tcg                             1173

SEQ ID NO: 272          moltype = DNA  length = 1166
FEATURE                 Location/Qualifiers
source                  1..1166
                        mol_type = genomic DNA
                        organism = Levilactobacillus brevis
SEQUENCE: 272
agnnnacgat gctaataatg cagtcgaacg agcttccgtt gaatgacgtg cttgcactga  60
tttcaacaat gaagcgagtg gcgaactggt gagtaacacg tggggaatct gcccagaagc  120
aggggataac acttggaaac aggtgctaat accgtataac aacaaaatcc gcatggattt  180
tgtttgaaag gtggcttcgg ctatcacttc tggatgatcc cgcggcgtat tagttagttg  240
gtgaggtaaa ggcccaccaa gacgatgata cgtagccgac ctgagagggt aatcggccac  300
attgggactg agacacggcc caaactccta cgggaggcag cagtagggaa tcttccacaa  360
tggacgaaag tctgatggag caatgccgcg tgagtgaaga agggtttcgg ctcgtaaaac  420
tctgttgtta aagaagaaca cctttgagag taactgttca agggttgacg gtatttaacc  480
agaaagccac ggctaactac gtgccagcag ccgcggtaat acgtaggtgg caagcgttgt  540
ccggatttat tgggcgtaaa gcgagcgcag gcggtttttt aagtctgatg tgaaagcctt  600
cggcttaacc ggagaagtgc atcggaaact gggagacttg agtgcagaag aggacagtgg  660
aactccatgt gtagcggtgg aatgcgtaga tatatggaag agcaccagtg gcgaaggcgg  720
ctgtctagtc tgtaactgac gctgaggctc gaaagcatgg gtagcgaaca ggattagata  780
ccctggtagt ccatgccgta acgatgagtg ctagtgttgg gagggtttcc gcccttcagt  840
gctgcagcta acgcattaag cactccgcct ggggagtacg accgcagttg aagctcaaag  900
gaattgacgg ggccgcacag cgtgagcatg tgttaatcga gctacgcgag gactacagtc  960
tgacatctct gcatctagaa gatagacgtc cctcggacga tgacntggtg catgngcgtc  1020
agctcgtctg gaatgtggta gtcccgcacg agcccactta atatcagtgc agcatcatgn  1080
actctgtgag actgcgttga cannnannng ntactnnnct ctctatgcnt agactgctac  1140
anntctcaat gacgtacaca gatnga                                     1166
```